United States Patent
Chan et al.

(10) Patent No.: US 11,332,530 B2
(45) Date of Patent: May 17, 2022

(54) DETERMINANTS OF CANCER RESPONSE TO IMMUNOTHERAPY

(71) Applicant: MEMORIAL SLOAN KETTERING CANCER CENTER, New York, NY (US)

(72) Inventors: Timothy A. Chan, New York, NY (US); Nadeem Riaz, New York, NY (US)

(73) Assignee: MEMORIAL SLOAN KETTERING CANCER CENTER, New York, NY (US)

(*) Notice: Subject to any disclaimer, the term of this patent is extended or adjusted under 35 U.S.C. 154(b) by 466 days.

(21) Appl. No.: 16/334,721

(22) PCT Filed: Sep. 22, 2017

(86) PCT No.: PCT/US2017/052908
§ 371 (c)(1),
(2) Date: Mar. 19, 2019

(87) PCT Pub. No.: WO2018/057858
PCT Pub. Date: Mar. 29, 2018

(65) Prior Publication Data
US 2019/0263910 A1    Aug. 29, 2019

Related U.S. Application Data

(60) Provisional application No. 62/399,212, filed on Sep. 23, 2016.

(51) Int. Cl.
| | |
|---|---|
| C07K 16/28 | (2006.01) |
| A61K 39/395 | (2006.01) |
| A61P 35/00 | (2006.01) |
| C12Q 1/6886 | (2018.01) |
| G01N 33/68 | (2006.01) |
| C07K 14/81 | (2006.01) |
| A61P 29/00 | (2006.01) |
| A61K 39/00 | (2006.01) |

(52) U.S. Cl.
CPC .......... C07K 16/2818 (2013.01); A61P 29/00 (2018.01); A61P 35/00 (2018.01); C07K 14/8121 (2013.01); C12Q 1/6886 (2013.01); G01N 33/68 (2013.01); A61K 2039/505 (2013.01); C07K 2317/21 (2013.01); C07K 2317/24 (2013.01); C07K 2317/76 (2013.01); C12Q 2600/156 (2013.01)

(58) Field of Classification Search
None
See application file for complete search history.

(56) References Cited

U.S. PATENT DOCUMENTS

| | | |
|---|---|---|
| 2010/0209413 A1 | 8/2010 | Walley et al. |
| 2011/0294673 A1 | 12/2011 | Stacey et al. |
| 2013/0071856 A1 | 3/2013 | Liao et al. |
| 2016/0000893 A1 | 1/2016 | Hunt et al. |
| 2016/0168200 A1 | 6/2016 | Weinschenk et al. |
| 2019/0092864 A1* | 3/2019 | Chan ................. C07K 16/2818 |
| 2020/0232040 A1* | 7/2020 | Luksza ............ G01N 33/56977 |

FOREIGN PATENT DOCUMENTS

| | | |
|---|---|---|
| WO | WO-2007/056604 A2 | 5/2007 |
| WO | WO-2015/103037 A2 | 7/2015 |

OTHER PUBLICATIONS

Balducci L. (2016) Seminars in Oncology Nursing, 32: 314-324.*
Buchbinder et al. (2016) Am J Clin. Oncol, 39: 98-106.*
Demaria et al. (2019) Nature, 574: 45-56.*
Heit et al. (2013) Human Genomics 7: 1-14.*
Prendergast et al. (2019) Int Rev Cell Mol Biol. 336: 175-203.*
Sanchez-Trincado et al. (2017) J Immunol Research, V. 2017, Article ID 2680160, 14 pages.*
Tokunaga et al. (2019) Cancer Treatment Reviews 73: 10-19.*
International Search Report and Written Opinion, PCT/US2017/052908 (dated Jan. 18, 2018).
Pavlikova et al., "Differentially expressed proteins in human breast cancer cells sensitive and resistant to paclitaxel," Int. J. Oncol., 45(2), pp. 822-830 (2014).
Riaz et al., "Recurrent SERPINB3 and SERPINB4 mutations in patients who respond to anti-CTLA4 immunotherapy," Nat. Genet., 46(11), pp. 1327-1329 (Sep. 26, 2016).
Valiente et al., "Serpins promote cancer cell survival and vascular co-option in brain metastasis," Cell, 156(5), pp. 1002-1016 (2014).
Yang et al., "Serpin peptidase inhibitor (SERPINB5) haplotypes are associated with susceptibility to hepatocellular carcinoma," Sci. Rep., 6:26605 (May 25, 2016).
Van Houdt et al., "Expression of the Apoptosis Inhibitor Protease Inhibitor 9 Predicts Clinical Outcome in Vaccinated Patients with Stage III and IV Melanoma," Clin. Can. Res., 11(17), pp. 6400-6407 (Sep. 1, 2005).
Vermeulen et al., "Pediatric Primitive Neuroectodermal Tumors of the Central Nervous System Differentially Express Granzyme Inhibitors," PLOS One, 11:3 (8 pages) (Mar. 10, 2016) DOI: 10.1371/journal.pone.0151465.

* cited by examiner

*Primary Examiner* — Ilia I Ouspenski
(74) *Attorney, Agent, or Firm* — Foley & Lardner LLP

(57) ABSTRACT

Molecular determinants of cancer response to immunotherapy are described, as are systems and tools for identifying and/or characterizing cancers likely to respond to immunotherapy.

7 Claims, 22 Drawing Sheets
Specification includes a Sequence Listing.

```
SerpinB3    1   MNSLSEANTKFMEDIKQQFRKS-KENMIFYSPTSISSALGMVLLGAKDNTAQQIKKVLAF
Ovalbumin   1   MGSIGAASMEFCFDVFKELKVHHANENIFYCPIAIMSALAMVYLGAKDSTRTQINKVVRF
                *.:  **:.* :   :..*::.     ***:..* : *** ***::*::..  *:.*  *

E                         K
                                  E                         K
SerpinB3    60  DQVTENTTGKAATYHVDRSGNVHHQFQKLLTEFNKSTDAYELKIANKLYGEKTYLFLQEY
Ovalbumin   61  DKLPGFG---DSIEAQCGTSVNVHSSLRDILNQITKPNDVYSFSLASRLYAEERYPILPEY
                *::.  .   ::: :: .:..***..: ::*.:.: ..* *.:: :.:**.*:.   **

S
                                               S
                            V   C      L    Q
SerpinB3    120 LDAIKKFYQTSVESVDFANAPEESRKKINSWVESQTNEKIKNLIPEGNIGSNTTLVLVNA
Ovalbumin   119 LQCVKELYRGGLEPINFQTAADQARELINSWVESQTNGIIRNVLQPSSVDSQTAMVLVNA
                *: ::: *: .:*.::*..*.:.:.:: *********..*:*:* ..:.*..* :****
```

Mutation
[Known HLA-pres

FIG. 6 (cont.)

○ + + PCPG (TCGA)
○ + , Ewing Sarcoma (DFCI)
○ + , Liad (Insem 2014)
○ + , PANET (John Hopkins 2011)
○ + , Cholangiocarcinoma (TCGA)
○ + + Cholangiocarcinoma (NUS)
○ + , Head & neck (JHU)
○ + , Cholangiocarcinoma (NCCS)
○ + , ACyC (MSKCC, 2013)
○ + + GBM (TCGA 2008)
○ + + ACyC (MDA 2015)
○ + , Head & neck (MDA)
○ + , NEPC (Trento/Cornell/Broad 2016)
○ + + NBL (Cologne 2015)
○ + , NBL (AMC)
○ + , NPC (Singapore)
○ + , NCI-60
○ + + MDS (Tokyo)
○ + , ccRCC (IRC)
○ + , Stomach (TMUCIH 2015)
○ + , GBC (Shanghai)
○ + , Ewing Sarcoma (Institut Curie)
○ + , Breast (BCCRC Xenograft)
○ + + MBL (PCGP)
○ + , MBL (ICGC)
○ + , MBL (Broad)
○ + , MCL (IDIBIPS 2013)
○ + , PLMESO (NYU 2015)
○ + , MPNST (MSKCC)
○ + + Esophagus sq (ICGC)
○ + , ACyC (FMI 2014)
○ + + Bladder PV (MSKCC)
○ + + Lung adeno (TSP)
○ + , DLBCL (Broad 2012)
○ + , Lung adeno (MSKCC)
○ + , Prostate (TCGA)
○ + + Thyroid (TCGA)

SEQUENCE LISTING

```
<160> NUMBER OF SEQ ID NOS: 177

<210> SEQ ID NO 1
<211> LENGTH: 9
<212> TYPE: PRT
<213> ORGANISM: Homo sapiens

<400> SEQUENCE: 1

Phe Leu Gln Glu Tyr Leu Asp Val Ile
1               5

<210> SEQ ID NO 2
<211> LENGTH: 9
<212> TYPE: PRT
<213> ORGANISM: Homo sapiens

<400> SEQUENCE: 2

Tyr Leu Asp Val Ile Lys Lys Phe Tyr
1               5

<210> SEQ ID NO 3
<211> LENGTH: 9
<212> TYPE: PRT
<213> ORGANISM: Homo sapiens

<400> SEQUENCE: 3

Phe Ala Asn Ala Leu Glu Glu Ser Arg
1               5
```

```
<210> SEQ ID NO 4
<211> LENGTH: 9
<212> TYPE: PRT
<213> ORGANISM: Homo sapiens

<400> SEQUENCE: 4

Pro Thr Ser Thr Asn Glu Glu Phe Tyr
1               5

<210> SEQ ID NO 5
<211> LENGTH: 9
<212> TYPE: PRT
<213> ORGANISM: Homo sapiens

<400> SEQUENCE: 5

Phe Tyr Cys Asn His Pro Phe Leu Phe
1               5

<210> SEQ ID NO 6
<211> LENGTH: 9
<212> TYPE: PRT
<213> ORGANISM: Homo sapiens

<400> SEQUENCE: 6

Phe Tyr Cys Asn His Pro Phe Leu Phe
1               5

<210> SEQ ID NO 7
<211> LENGTH: 9
<212> TYPE: PRT
<213> ORGANISM: Homo sapiens

<400> SEQUENCE: 7

Tyr His Val Asp Arg Ser Glu Asn Val
1               5

<210> SEQ ID NO 8
<211> LENGTH: 9
<212> TYPE: PRT
<213> ORGANISM: Homo sapiens

<400> SEQUENCE: 8

Tyr His Val Asp Arg Ser Glu Asn Val
1               5

<210> SEQ ID NO 9
<211> LENGTH: 9
<212> TYPE: PRT
<213> ORGANISM: Homo sapiens

<400> SEQUENCE: 9

Lys Leu Ile Glu Trp Thr Ser Leu Gln
1               5

<210> SEQ ID NO 10
<211> LENGTH: 9
<212> TYPE: PRT
<213> ORGANISM: Homo sapiens

<400> SEQUENCE: 10

Ile Glu Trp Thr Ser Leu Gln Asn Met
1               5

<210> SEQ ID NO 11
```

<211> LENGTH: 9
<212> TYPE: PRT
<213> ORGANISM: Homo sapiens

<400> SEQUENCE: 11

Leu Thr Ala Glu Lys Leu Ile Glu Trp
1               5

<210> SEQ ID NO 12
<211> LENGTH: 9
<212> TYPE: PRT
<213> ORGANISM: Homo sapiens

<400> SEQUENCE: 12

Arg Gln Tyr Asn Phe Phe Asn Phe Ala
1               5

<210> SEQ ID NO 13
<211> LENGTH: 9
<212> TYPE: PRT
<213> ORGANISM: Homo sapiens

<400> SEQUENCE: 13

Arg Gln Tyr Asn Phe Phe Asn Phe Ala
1               5

<210> SEQ ID NO 14
<211> LENGTH: 9
<212> TYPE: PRT
<213> ORGANISM: Homo sapiens

<400> SEQUENCE: 14

Tyr Asn Phe Phe Asn Phe Ala Leu Leu
1               5

<210> SEQ ID NO 15
<211> LENGTH: 9
<212> TYPE: PRT
<213> ORGANISM: Homo sapiens

<400> SEQUENCE: 15

Phe Thr Asp Ala Tyr Glu Leu Lys Ile
1               5

<210> SEQ ID NO 16
<211> LENGTH: 9
<212> TYPE: PRT
<213> ORGANISM: Homo sapiens

<400> SEQUENCE: 16

Phe Thr Asp Ala Tyr Glu Leu Lys Ile
1               5

<210> SEQ ID NO 17
<211> LENGTH: 9
<212> TYPE: PRT
<213> ORGANISM: Homo sapiens

<400> SEQUENCE: 17

Leu Leu Glu Asn Val Gln Ala Lys Val
1               5

<210> SEQ ID NO 18
<211> LENGTH: 9
<212> TYPE: PRT

<213> ORGANISM: Homo sapiens

<400> SEQUENCE: 18

Ala Leu Leu Glu Asn Val Gln Ala Lys
1               5

<210> SEQ ID NO 19
<211> LENGTH: 10
<212> TYPE: PRT
<213> ORGANISM: Homo sapiens

<400> SEQUENCE: 19

Ile Leu Phe Tyr Gly Arg Phe Ser Thr Pro
1               5                   10

<210> SEQ ID NO 20
<211> LENGTH: 9
<212> TYPE: PRT
<213> ORGANISM: Homo sapiens

<400> SEQUENCE: 20

Lys Tyr Leu Asp Ala Ile Lys Lys Phe
1               5

<210> SEQ ID NO 21
<211> LENGTH: 9
<212> TYPE: PRT
<213> ORGANISM: Homo sapiens

<400> SEQUENCE: 21

Phe Leu Gln Lys Tyr Leu Asp Ala Ile
1               5

<210> SEQ ID NO 22
<211> LENGTH: 9
<212> TYPE: PRT
<213> ORGANISM: Homo sapiens

<400> SEQUENCE: 22

Thr Tyr Leu Phe Leu Gln Lys Tyr Leu
1               5

<210> SEQ ID NO 23
<211> LENGTH: 9
<212> TYPE: PRT
<213> ORGANISM: Homo sapiens

<400> SEQUENCE: 23

Ser Met Ile Val Leu Leu Pro Asn Lys
1               5

<210> SEQ ID NO 24
<211> LENGTH: 9
<212> TYPE: PRT
<213> ORGANISM: Homo sapiens

<400> SEQUENCE: 24

Gln Val Thr Glu Asn Thr Thr Lys Lys
1               5

<210> SEQ ID NO 25
<211> LENGTH: 9
<212> TYPE: PRT
<213> ORGANISM: Homo sapiens

<400> SEQUENCE: 25

Met Glu Ala Ala Ala Ala Thr Ala Val
1               5

<210> SEQ ID NO 26
<211> LENGTH: 9
<212> TYPE: PRT
<213> ORGANISM: Homo sapiens

<400> SEQUENCE: 26

Tyr His Val Asp Arg Ser Arg Asn Val
1               5

<210> SEQ ID NO 27
<211> LENGTH: 15
<212> TYPE: PRT
<213> ORGANISM: Homo sapiens

<400> SEQUENCE: 27

Phe Gly Glu Lys Thr Tyr Leu Phe Leu Gln Glu Tyr Leu Asp Val
1               5                   10                  15

<210> SEQ ID NO 28
<211> LENGTH: 15
<212> TYPE: PRT
<213> ORGANISM: Homo sapiens

<400> SEQUENCE: 28

Gly Glu Lys Thr Tyr Leu Phe Leu Gln Glu Tyr Leu Asp Val Ile
1               5                   10                  15

<210> SEQ ID NO 29
<211> LENGTH: 15
<212> TYPE: PRT
<213> ORGANISM: Homo sapiens

<400> SEQUENCE: 29

Glu Lys Thr Tyr Leu Phe Leu Gln Glu Tyr Leu Asp Val Ile Lys
1               5                   10                  15

<210> SEQ ID NO 30
<211> LENGTH: 15
<212> TYPE: PRT
<213> ORGANISM: Homo sapiens

<400> SEQUENCE: 30

Lys Thr Tyr Leu Phe Leu Gln Glu Tyr Leu Asp Val Ile Lys Lys
1               5                   10                  15

<210> SEQ ID NO 31
<211> LENGTH: 15
<212> TYPE: PRT
<213> ORGANISM: Homo sapiens

<400> SEQUENCE: 31

Thr Tyr Leu Phe Leu Gln Glu Tyr Leu Asp Val Ile Lys Lys Phe
1               5                   10                  15

<210> SEQ ID NO 32
<211> LENGTH: 15
<212> TYPE: PRT
<213> ORGANISM: Homo sapiens

<400> SEQUENCE: 32

Tyr Leu Phe Leu Gln Glu Tyr Leu Asp Val Ile Lys Lys Phe Tyr
1               5                   10                  15

<210> SEQ ID NO 33
<211> LENGTH: 15
<212> TYPE: PRT
<213> ORGANISM: Homo sapiens

<400> SEQUENCE: 33

Phe Gly Glu Lys Thr Tyr Leu Phe Leu Gln Glu Tyr Leu Asp Val
1               5                   10                  15

<210> SEQ ID NO 34
<211> LENGTH: 15
<212> TYPE: PRT
<213> ORGANISM: Homo sapiens

<400> SEQUENCE: 34

Gly Glu Lys Thr Tyr Leu Phe Leu Gln Glu Tyr Leu Asp Val Ile
1               5                   10                  15

<210> SEQ ID NO 35
<211> LENGTH: 15
<212> TYPE: PRT
<213> ORGANISM: Homo sapiens

<400> SEQUENCE: 35

Glu Lys Thr Tyr Leu Phe Leu Gln Glu Tyr Leu Asp Val Ile Lys
1               5                   10                  15

<210> SEQ ID NO 36
<211> LENGTH: 15
<212> TYPE: PRT
<213> ORGANISM: Homo sapiens

<400> SEQUENCE: 36

Lys Thr Tyr Leu Phe Leu Gln Glu Tyr Leu Asp Val Ile Lys Lys
1               5                   10                  15

<210> SEQ ID NO 37
<211> LENGTH: 15
<212> TYPE: PRT
<213> ORGANISM: Homo sapiens

<400> SEQUENCE: 37

Thr Tyr Leu Phe Leu Gln Glu Tyr Leu Asp Val Ile Lys Lys Phe
1               5                   10                  15

<210> SEQ ID NO 38
<211> LENGTH: 15
<212> TYPE: PRT
<213> ORGANISM: Homo sapiens

<400> SEQUENCE: 38

Tyr Leu Phe Leu Gln Glu Tyr Leu Asp Val Ile Lys Lys Phe Tyr
1               5                   10                  15

<210> SEQ ID NO 39
<211> LENGTH: 15
<212> TYPE: PRT
<213> ORGANISM: Homo sapiens

<400> SEQUENCE: 39

Leu Phe Leu Gln Glu Tyr Leu Asp Val Ile Lys Lys Phe Tyr Gln
1               5                   10                  15

<210> SEQ ID NO 40
<211> LENGTH: 15
<212> TYPE: PRT
<213> ORGANISM: Homo sapiens

<400> SEQUENCE: 40

Phe Gly Glu Lys Thr Tyr Leu Phe Leu Gln Glu Tyr Leu Asp Val
1               5                   10                  15

<210> SEQ ID NO 41
<211> LENGTH: 15
<212> TYPE: PRT
<213> ORGANISM: Homo sapiens

<400> SEQUENCE: 41

Gly Glu Lys Thr Tyr Leu Phe Leu Gln Glu Tyr Leu Asp Val Ile
1               5                   10                  15

<210> SEQ ID NO 42
<211> LENGTH: 15
<212> TYPE: PRT
<213> ORGANISM: Homo sapiens

<400> SEQUENCE: 42

Glu Lys Thr Tyr Leu Phe Leu Gln Glu Tyr Leu Asp Val Ile Lys
1               5                   10                  15

<210> SEQ ID NO 43
<211> LENGTH: 15
<212> TYPE: PRT
<213> ORGANISM: Homo sapiens

<400> SEQUENCE: 43

Lys Thr Tyr Leu Phe Leu Gln Glu Tyr Leu Asp Val Ile Lys Lys
1               5                   10                  15

<210> SEQ ID NO 44
<211> LENGTH: 15
<212> TYPE: PRT
<213> ORGANISM: Homo sapiens

<400> SEQUENCE: 44

Thr Tyr Leu Phe Leu Gln Glu Tyr Leu Asp Val Ile Lys Lys Phe
1               5                   10                  15

<210> SEQ ID NO 45
<211> LENGTH: 15
<212> TYPE: PRT
<213> ORGANISM: Homo sapiens

<400> SEQUENCE: 45

Phe Gly Glu Lys Thr Tyr Leu Phe Leu Gln Glu Tyr Leu Asp Val
1               5                   10                  15

<210> SEQ ID NO 46
<211> LENGTH: 15
<212> TYPE: PRT
<213> ORGANISM: Homo sapiens

<400> SEQUENCE: 46

Gly Glu Lys Thr Tyr Leu Phe Leu Gln Glu Tyr Leu Asp Val Ile
1               5                   10                  15

```
<210> SEQ ID NO 47
<211> LENGTH: 15
<212> TYPE: PRT
<213> ORGANISM: Homo sapiens

<400> SEQUENCE: 47

Glu Lys Thr Tyr Leu Phe Leu Gln Glu Tyr Leu Asp Val Ile Lys
1               5                   10                  15

<210> SEQ ID NO 48
<211> LENGTH: 15
<212> TYPE: PRT
<213> ORGANISM: Homo sapiens

<400> SEQUENCE: 48

Lys Thr Tyr Leu Phe Leu Gln Glu Tyr Leu Asp Val Ile Lys Lys
1               5                   10                  15

<210> SEQ ID NO 49
<211> LENGTH: 15
<212> TYPE: PRT
<213> ORGANISM: Homo sapiens

<400> SEQUENCE: 49

Thr Tyr Leu Phe Leu Gln Glu Tyr Leu Asp Val Ile Lys Lys Phe
1               5                   10                  15

<210> SEQ ID NO 50
<211> LENGTH: 15
<212> TYPE: PRT
<213> ORGANISM: Homo sapiens

<400> SEQUENCE: 50

Glu Gly Ala Glu Ala Ala Ala Thr Ala Val Val Gly Phe Arg
1               5                   10                  15

<210> SEQ ID NO 51
<211> LENGTH: 15
<212> TYPE: PRT
<213> ORGANISM: Homo sapiens

<400> SEQUENCE: 51

Gly Ala Glu Ala Ala Ala Ala Thr Ala Val Val Gly Phe Arg Ser
1               5                   10                  15

<210> SEQ ID NO 52
<211> LENGTH: 15
<212> TYPE: PRT
<213> ORGANISM: Homo sapiens

<400> SEQUENCE: 52

Ala Glu Ala Ala Ala Ala Thr Ala Val Val Gly Phe Arg Ser Ser
1               5                   10                  15

<210> SEQ ID NO 53
<211> LENGTH: 15
<212> TYPE: PRT
<213> ORGANISM: Homo sapiens

<400> SEQUENCE: 53

Glu Ala Ala Ala Ala Thr Ala Val Val Gly Phe Arg Ser Ser Pro
1               5                   10                  15

<210> SEQ ID NO 54
<211> LENGTH: 15
```

```
<212> TYPE: PRT
<213> ORGANISM: Homo sapiens

<400> SEQUENCE: 54

Lys Phe Ile Gln Met Met Arg Gln Tyr Thr Ser Phe His Phe Ala
1               5                   10                  15

<210> SEQ ID NO 55
<211> LENGTH: 15
<212> TYPE: PRT
<213> ORGANISM: Homo sapiens

<400> SEQUENCE: 55

Asn Glu Glu Phe Tyr Cys Asn His Pro Phe Leu Phe Phe Ile Arg
1               5                   10                  15

<210> SEQ ID NO 56
<211> LENGTH: 15
<212> TYPE: PRT
<213> ORGANISM: Homo sapiens

<400> SEQUENCE: 56

Glu Glu Phe Tyr Cys Asn His Pro Phe Leu Phe Phe Ile Arg Gln
1               5                   10                  15

<210> SEQ ID NO 57
<211> LENGTH: 15
<212> TYPE: PRT
<213> ORGANISM: Homo sapiens

<400> SEQUENCE: 57

Thr Asn Glu Glu Phe Tyr Cys Asn His Pro Phe Leu Phe Phe Ile
1               5                   10                  15

<210> SEQ ID NO 58
<211> LENGTH: 15
<212> TYPE: PRT
<213> ORGANISM: Homo sapiens

<400> SEQUENCE: 58

Asn Glu Glu Phe Tyr Cys Asn His Pro Phe Leu Phe Phe Ile Arg
1               5                   10                  15

<210> SEQ ID NO 59
<211> LENGTH: 15
<212> TYPE: PRT
<213> ORGANISM: Homo sapiens

<400> SEQUENCE: 59

Glu Glu Phe Tyr Cys Asn His Pro Phe Leu Phe Phe Ile Arg Gln
1               5                   10                  15

<210> SEQ ID NO 60
<211> LENGTH: 15
<212> TYPE: PRT
<213> ORGANISM: Homo sapiens

<400> SEQUENCE: 60

Glu Phe Tyr Cys Asn His Pro Phe Leu Phe Phe Ile Arg Gln Asn
1               5                   10                  15

<210> SEQ ID NO 61
<211> LENGTH: 15
<212> TYPE: PRT
<213> ORGANISM: Homo sapiens
```

<400> SEQUENCE: 61

Thr Glu Glu Gly Ala Glu Ala Ala Ala Thr Ala Val Val Ala
1               5                   10                  15

<210> SEQ ID NO 62
<211> LENGTH: 15
<212> TYPE: PRT
<213> ORGANISM: Homo sapiens

<400> SEQUENCE: 62

Glu Glu Gly Ala Glu Ala Ala Ala Thr Ala Val Val Ala Phe
1               5                   10                  15

<210> SEQ ID NO 63
<211> LENGTH: 15
<212> TYPE: PRT
<213> ORGANISM: Homo sapiens

<400> SEQUENCE: 63

Glu Gly Ala Glu Ala Ala Ala Thr Ala Val Val Ala Phe Gly
1               5                   10                  15

<210> SEQ ID NO 64
<211> LENGTH: 15
<212> TYPE: PRT
<213> ORGANISM: Homo sapiens

<400> SEQUENCE: 64

Gly Ala Glu Ala Ala Ala Ala Thr Ala Val Val Ala Phe Gly Ser
1               5                   10                  15

<210> SEQ ID NO 65
<211> LENGTH: 15
<212> TYPE: PRT
<213> ORGANISM: Homo sapiens

<400> SEQUENCE: 65

Ala Glu Ala Ala Ala Ala Thr Ala Val Val Ala Phe Gly Ser Ser
1               5                   10                  15

<210> SEQ ID NO 66
<211> LENGTH: 15
<212> TYPE: PRT
<213> ORGANISM: Homo sapiens

<400> SEQUENCE: 66

Glu Ala Ala Ala Ala Thr Ala Val Val Ala Phe Gly Ser Ser Pro
1               5                   10                  15

<210> SEQ ID NO 67
<211> LENGTH: 15
<212> TYPE: PRT
<213> ORGANISM: Homo sapiens

<400> SEQUENCE: 67

Ala Ala Ala Ala Thr Ala Val Val Ala Phe Gly Ser Ser Pro Thr
1               5                   10                  15

<210> SEQ ID NO 68
<211> LENGTH: 15
<212> TYPE: PRT
<213> ORGANISM: Homo sapiens

<400> SEQUENCE: 68

Thr Glu Glu Gly Ala Glu Ala Ala Ala Thr Ala Val Val Ala
1               5                   10                  15

<210> SEQ ID NO 69
<211> LENGTH: 15
<212> TYPE: PRT
<213> ORGANISM: Homo sapiens

<400> SEQUENCE: 69

Glu Glu Gly Ala Glu Ala Ala Ala Thr Ala Val Val Ala Phe
1               5                   10                  15

<210> SEQ ID NO 70
<211> LENGTH: 15
<212> TYPE: PRT
<213> ORGANISM: Homo sapiens

<400> SEQUENCE: 70

Glu Gly Ala Glu Ala Ala Ala Thr Ala Val Val Ala Phe Gly
1               5                   10                  15

<210> SEQ ID NO 71
<211> LENGTH: 15
<212> TYPE: PRT
<213> ORGANISM: Homo sapiens

<400> SEQUENCE: 71

Gly Ala Glu Ala Ala Ala Thr Ala Val Val Ala Phe Gly Ser
1               5                   10                  15

<210> SEQ ID NO 72
<211> LENGTH: 15
<212> TYPE: PRT
<213> ORGANISM: Homo sapiens

<400> SEQUENCE: 72

Ala Glu Ala Ala Ala Thr Ala Val Val Ala Phe Gly Ser Ser
1               5                   10                  15

<210> SEQ ID NO 73
<211> LENGTH: 15
<212> TYPE: PRT
<213> ORGANISM: Homo sapiens

<400> SEQUENCE: 73

Glu Ala Ala Ala Ala Thr Ala Val Val Ala Phe Gly Ser Ser Pro
1               5                   10                  15

<210> SEQ ID NO 74
<211> LENGTH: 15
<212> TYPE: PRT
<213> ORGANISM: Homo sapiens

<400> SEQUENCE: 74

Ala Ala Ala Ala Thr Ala Val Val Ala Phe Gly Ser Ser Pro Thr
1               5                   10                  15

<210> SEQ ID NO 75
<211> LENGTH: 15
<212> TYPE: PRT
<213> ORGANISM: Homo sapiens

<400> SEQUENCE: 75

Val Gln Met Met Arg Gln Tyr Asn Phe Phe Asn Phe Ala Leu Leu

-continued

```
1               5                   10                  15

<210> SEQ ID NO 76
<211> LENGTH: 15
<212> TYPE: PRT
<213> ORGANISM: Homo sapiens

<400> SEQUENCE: 76

Gln Met Met Arg Gln Tyr Asn Phe Phe Asn Phe Ala Leu Leu Glu
1               5                   10                  15

<210> SEQ ID NO 77
<211> LENGTH: 15
<212> TYPE: PRT
<213> ORGANISM: Homo sapiens

<400> SEQUENCE: 77

Met Met Arg Gln Tyr Asn Phe Phe Asn Phe Ala Leu Leu Glu Asp
1               5                   10                  15

<210> SEQ ID NO 78
<211> LENGTH: 15
<212> TYPE: PRT
<213> ORGANISM: Homo sapiens

<400> SEQUENCE: 78

Met Arg Gln Tyr Asn Phe Phe Asn Phe Ala Leu Leu Glu Asp Val
1               5                   10                  15

<210> SEQ ID NO 79
<211> LENGTH: 15
<212> TYPE: PRT
<213> ORGANISM: Homo sapiens

<400> SEQUENCE: 79

Arg Gln Tyr Asn Phe Phe Asn Phe Ala Leu Leu Glu Asp Val Gln
1               5                   10                  15

<210> SEQ ID NO 80
<211> LENGTH: 15
<212> TYPE: PRT
<213> ORGANISM: Homo sapiens

<400> SEQUENCE: 80

Gln Tyr Asn Phe Phe Asn Phe Ala Leu Leu Glu Asp Val Gln Ala
1               5                   10                  15

<210> SEQ ID NO 81
<211> LENGTH: 15
<212> TYPE: PRT
<213> ORGANISM: Homo sapiens

<400> SEQUENCE: 81

Tyr Asn Phe Phe Asn Phe Ala Leu Leu Glu Asp Val Gln Ala Lys
1               5                   10                  15

<210> SEQ ID NO 82
<211> LENGTH: 15
<212> TYPE: PRT
<213> ORGANISM: Homo sapiens

<400> SEQUENCE: 82

Asn Phe Phe Asn Phe Ala Leu Leu Glu Asp Val Gln Ala Lys Val
1               5                   10                  15
```

<210> SEQ ID NO 83
<211> LENGTH: 15
<212> TYPE: PRT
<213> ORGANISM: Homo sapiens

<400> SEQUENCE: 83

Gln Met Met Arg Gln Tyr Asn Phe Phe Asn Phe Ala Leu Leu Glu
1               5                   10                  15

<210> SEQ ID NO 84
<211> LENGTH: 15
<212> TYPE: PRT
<213> ORGANISM: Homo sapiens

<400> SEQUENCE: 84

Met Met Arg Gln Tyr Asn Phe Phe Asn Phe Ala Leu Leu Glu Asp
1               5                   10                  15

<210> SEQ ID NO 85
<211> LENGTH: 15
<212> TYPE: PRT
<213> ORGANISM: Homo sapiens

<400> SEQUENCE: 85

Met Arg Gln Tyr Asn Phe Phe Asn Phe Ala Leu Leu Glu Asp Val
1               5                   10                  15

<210> SEQ ID NO 86
<211> LENGTH: 15
<212> TYPE: PRT
<213> ORGANISM: Homo sapiens

<400> SEQUENCE: 86

Arg Gln Tyr Asn Phe Phe Asn Phe Ala Leu Leu Glu Asp Val Gln
1               5                   10                  15

<210> SEQ ID NO 87
<211> LENGTH: 15
<212> TYPE: PRT
<213> ORGANISM: Homo sapiens

<400> SEQUENCE: 87

Gln Tyr Asn Phe Phe Asn Phe Ala Leu Leu Glu Asp Val Gln Ala
1               5                   10                  15

<210> SEQ ID NO 88
<211> LENGTH: 15
<212> TYPE: PRT
<213> ORGANISM: Homo sapiens

<400> SEQUENCE: 88

Tyr Asn Phe Phe Asn Phe Ala Leu Leu Glu Asp Val Gln Ala Lys
1               5                   10                  15

<210> SEQ ID NO 89
<211> LENGTH: 15
<212> TYPE: PRT
<213> ORGANISM: Homo sapiens

<400> SEQUENCE: 89

Asn Phe Phe Asn Phe Ala Leu Leu Glu Asp Val Gln Ala Lys Val
1               5                   10                  15

<210> SEQ ID NO 90

```
<211> LENGTH: 15
<212> TYPE: PRT
<213> ORGANISM: Homo sapiens

<400> SEQUENCE: 90

Gln Tyr Asn Ser Phe Asn Phe Ala Leu Leu Glu Asn Val Gln Ala
1               5                   10                  15

<210> SEQ ID NO 91
<211> LENGTH: 15
<212> TYPE: PRT
<213> ORGANISM: Homo sapiens

<400> SEQUENCE: 91

Tyr Asn Ser Phe Asn Phe Ala Leu Leu Glu Asn Val Gln Ala Lys
1               5                   10                  15

<210> SEQ ID NO 92
<211> LENGTH: 15
<212> TYPE: PRT
<213> ORGANISM: Homo sapiens

<400> SEQUENCE: 92

Asn Ser Phe Asn Phe Ala Leu Leu Glu Asn Val Gln Ala Lys Val
1               5                   10                  15

<210> SEQ ID NO 93
<211> LENGTH: 15
<212> TYPE: PRT
<213> ORGANISM: Homo sapiens

<400> SEQUENCE: 93

Ser Phe Asn Phe Ala Leu Leu Glu Asn Val Gln Ala Lys Val Leu
1               5                   10                  15

<210> SEQ ID NO 94
<211> LENGTH: 15
<212> TYPE: PRT
<213> ORGANISM: Homo sapiens

<400> SEQUENCE: 94

Phe Asn Phe Ala Leu Leu Glu Asn Val Gln Ala Lys Val Leu Glu
1               5                   10                  15

<210> SEQ ID NO 95
<211> LENGTH: 15
<212> TYPE: PRT
<213> ORGANISM: Homo sapiens

<400> SEQUENCE: 95

Asn Phe Ala Leu Leu Glu Asn Val Gln Ala Lys Val Leu Glu Ile
1               5                   10                  15

<210> SEQ ID NO 96
<211> LENGTH: 15
<212> TYPE: PRT
<213> ORGANISM: Homo sapiens

<400> SEQUENCE: 96

Met Met Arg Gln Tyr Asn Ser Phe Asn Phe Ala Leu Leu Glu Asn
1               5                   10                  15

<210> SEQ ID NO 97
<211> LENGTH: 15
<212> TYPE: PRT
```

<213> ORGANISM: Homo sapiens

<400> SEQUENCE: 97

Met Arg Gln Tyr Asn Ser Phe Asn Phe Ala Leu Leu Glu Asn Val
1               5                   10                  15

<210> SEQ ID NO 98
<211> LENGTH: 15
<212> TYPE: PRT
<213> ORGANISM: Homo sapiens

<400> SEQUENCE: 98

Arg Gln Tyr Asn Ser Phe Asn Phe Ala Leu Leu Glu Asn Val Gln
1               5                   10                  15

<210> SEQ ID NO 99
<211> LENGTH: 15
<212> TYPE: PRT
<213> ORGANISM: Homo sapiens

<400> SEQUENCE: 99

Gln Tyr Asn Ser Phe Asn Phe Ala Leu Leu Glu Asn Val Gln Ala
1               5                   10                  15

<210> SEQ ID NO 100
<211> LENGTH: 15
<212> TYPE: PRT
<213> ORGANISM: Homo sapiens

<400> SEQUENCE: 100

Tyr Asn Ser Phe Asn Phe Ala Leu Leu Glu Asn Val Gln Ala Lys
1               5                   10                  15

<210> SEQ ID NO 101
<211> LENGTH: 15
<212> TYPE: PRT
<213> ORGANISM: Homo sapiens

<400> SEQUENCE: 101

Met Arg Gln Tyr Asn Ser Phe Asn Phe Ala Leu Leu Glu Asn Val
1               5                   10                  15

<210> SEQ ID NO 102
<211> LENGTH: 15
<212> TYPE: PRT
<213> ORGANISM: Homo sapiens

<400> SEQUENCE: 102

Arg Gln Tyr Asn Ser Phe Asn Phe Ala Leu Leu Glu Asn Val Gln
1               5                   10                  15

<210> SEQ ID NO 103
<211> LENGTH: 15
<212> TYPE: PRT
<213> ORGANISM: Homo sapiens

<400> SEQUENCE: 103

Gln Tyr Asn Ser Phe Asn Phe Ala Leu Leu Glu Asn Val Gln Ala
1               5                   10                  15

<210> SEQ ID NO 104
<211> LENGTH: 15
<212> TYPE: PRT
<213> ORGANISM: Homo sapiens

```
<400> SEQUENCE: 104

Tyr Asn Ser Phe Asn Phe Ala Leu Leu Glu Asn Val Gln Ala Lys
1               5                   10                  15

<210> SEQ ID NO 105
<211> LENGTH: 15
<212> TYPE: PRT
<213> ORGANISM: Homo sapiens

<400> SEQUENCE: 105

Asn Ser Phe Asn Phe Ala Leu Leu Glu Asn Val Gln Ala Lys Val
1               5                   10                  15

<210> SEQ ID NO 106
<211> LENGTH: 15
<212> TYPE: PRT
<213> ORGANISM: Homo sapiens

<400> SEQUENCE: 106

Phe Asn Phe Ala Leu Leu Glu Asp Val Gln Ala Lys Val Leu Lys
1               5                   10                  15

<210> SEQ ID NO 107
<211> LENGTH: 15
<212> TYPE: PRT
<213> ORGANISM: Homo sapiens

<400> SEQUENCE: 107

Phe Asn Phe Ala Leu Leu Glu Asp Val Gln Ala Lys Val Leu Lys
1               5                   10                  15

<210> SEQ ID NO 108
<211> LENGTH: 15
<212> TYPE: PRT
<213> ORGANISM: Homo sapiens

<400> SEQUENCE: 108

Thr Tyr Leu Phe Leu Gln Glu Tyr Leu Asp Ala Ile Lys Lys Cys
1               5                   10                  15

<210> SEQ ID NO 109
<211> LENGTH: 15
<212> TYPE: PRT
<213> ORGANISM: Homo sapiens

<400> SEQUENCE: 109

Tyr Leu Phe Leu Gln Glu Tyr Leu Asp Ala Ile Lys Lys Cys Tyr
1               5                   10                  15

<210> SEQ ID NO 110
<211> LENGTH: 15
<212> TYPE: PRT
<213> ORGANISM: Homo sapiens

<400> SEQUENCE: 110

Thr Tyr Leu Phe Leu Gln Glu Tyr Leu Asp Ala Ile Lys Lys Cys
1               5                   10                  15

<210> SEQ ID NO 111
<211> LENGTH: 15
<212> TYPE: PRT
<213> ORGANISM: Homo sapiens

<400> SEQUENCE: 111
```

Thr Tyr Leu Phe Leu Gln Glu Tyr Leu Asp Ala Ile Lys Lys Cys
1               5                   10                  15

<210> SEQ ID NO 112
<211> LENGTH: 15
<212> TYPE: PRT
<213> ORGANISM: Homo sapiens

<400> SEQUENCE: 112

Ala Glu Ala Ala Ala Ala Thr Ala Val Val Gly Phe Gly Ser Leu
1               5                   10                  15

<210> SEQ ID NO 113
<211> LENGTH: 15
<212> TYPE: PRT
<213> ORGANISM: Homo sapiens

<400> SEQUENCE: 113

Ala Glu Ala Ala Ala Ala Thr Ala Val Val Gly Phe Gly Ser Leu
1               5                   10                  15

<210> SEQ ID NO 114
<211> LENGTH: 15
<212> TYPE: PRT
<213> ORGANISM: Homo sapiens

<400> SEQUENCE: 114

Glu Ala Ala Ala Ala Thr Ala Val Val Gly Phe Gly Ser Leu Pro
1               5                   10                  15

<210> SEQ ID NO 115
<211> LENGTH: 15
<212> TYPE: PRT
<213> ORGANISM: Homo sapiens

<400> SEQUENCE: 115

Ala Asn Lys Leu Phe Gly Glu Lys Thr Tyr Leu Phe Leu Gln Lys
1               5                   10                  15

<210> SEQ ID NO 116
<211> LENGTH: 15
<212> TYPE: PRT
<213> ORGANISM: Homo sapiens

<400> SEQUENCE: 116

Asn Lys Leu Phe Gly Glu Lys Thr Tyr Leu Phe Leu Gln Lys Tyr
1               5                   10                  15

<210> SEQ ID NO 117
<211> LENGTH: 15
<212> TYPE: PRT
<213> ORGANISM: Homo sapiens

<400> SEQUENCE: 117

Lys Leu Phe Gly Glu Lys Thr Tyr Leu Phe Leu Gln Lys Tyr Leu
1               5                   10                  15

<210> SEQ ID NO 118
<211> LENGTH: 15
<212> TYPE: PRT
<213> ORGANISM: Homo sapiens

<400> SEQUENCE: 118

Leu Phe Gly Glu Lys Thr Tyr Leu Phe Leu Gln Lys Tyr Leu Asp
1               5                   10                  15

```
<210> SEQ ID NO 119
<211> LENGTH: 15
<212> TYPE: PRT
<213> ORGANISM: Homo sapiens

<400> SEQUENCE: 119

Phe Gly Glu Lys Thr Tyr Leu Phe Leu Gln Lys Tyr Leu Asp Ala
1               5                   10                  15

<210> SEQ ID NO 120
<211> LENGTH: 15
<212> TYPE: PRT
<213> ORGANISM: Homo sapiens

<400> SEQUENCE: 120

Gly Glu Lys Thr Tyr Leu Phe Leu Gln Lys Tyr Leu Asp Ala Ile
1               5                   10                  15

<210> SEQ ID NO 121
<211> LENGTH: 15
<212> TYPE: PRT
<213> ORGANISM: Homo sapiens

<400> SEQUENCE: 121

Glu Lys Thr Tyr Leu Phe Leu Gln Lys Tyr Leu Asp Ala Ile Lys
1               5                   10                  15

<210> SEQ ID NO 122
<211> LENGTH: 15
<212> TYPE: PRT
<213> ORGANISM: Homo sapiens

<400> SEQUENCE: 122

Lys Thr Tyr Leu Phe Leu Gln Lys Tyr Leu Asp Ala Ile Lys Lys
1               5                   10                  15

<210> SEQ ID NO 123
<211> LENGTH: 15
<212> TYPE: PRT
<213> ORGANISM: Homo sapiens

<400> SEQUENCE: 123

Thr Tyr Leu Phe Leu Gln Lys Tyr Leu Asp Ala Ile Lys Lys Phe
1               5                   10                  15

<210> SEQ ID NO 124
<211> LENGTH: 15
<212> TYPE: PRT
<213> ORGANISM: Homo sapiens

<400> SEQUENCE: 124

Leu Ser Met Ile Val Leu Leu Pro Asn Lys Ile Asp Gly Leu Gln
1               5                   10                  15

<210> SEQ ID NO 125
<211> LENGTH: 15
<212> TYPE: PRT
<213> ORGANISM: Homo sapiens

<400> SEQUENCE: 125

Val Thr Glu Glu Gly Val Glu Ala Ala Ala Thr Val Val Val
1               5                   10                  15
```

```
<210> SEQ ID NO 126
<211> LENGTH: 15
<212> TYPE: PRT
<213> ORGANISM: Homo sapiens

<400> SEQUENCE: 126

Thr Glu Glu Gly Val Glu Ala Ala Ala Ala Thr Val Val Val Val
1               5                   10                  15

<210> SEQ ID NO 127
<211> LENGTH: 15
<212> TYPE: PRT
<213> ORGANISM: Homo sapiens

<400> SEQUENCE: 127

Glu Glu Gly Val Glu Ala Ala Ala Ala Thr Val Val Val Val Val
1               5                   10                  15

<210> SEQ ID NO 128
<211> LENGTH: 15
<212> TYPE: PRT
<213> ORGANISM: Homo sapiens

<400> SEQUENCE: 128

Val Thr Glu Glu Gly Val Glu Ala Ala Ala Ala Thr Val Val Val
1               5                   10                  15

<210> SEQ ID NO 129
<211> LENGTH: 15
<212> TYPE: PRT
<213> ORGANISM: Homo sapiens

<400> SEQUENCE: 129

Thr Glu Glu Gly Val Glu Ala Ala Ala Ala Thr Val Val Val Val
1               5                   10                  15

<210> SEQ ID NO 130
<211> LENGTH: 15
<212> TYPE: PRT
<213> ORGANISM: Homo sapiens

<400> SEQUENCE: 130

Glu Glu Gly Val Glu Ala Ala Ala Ala Thr Val Val Val Val Val
1               5                   10                  15

<210> SEQ ID NO 131
<211> LENGTH: 15
<212> TYPE: PRT
<213> ORGANISM: Homo sapiens

<400> SEQUENCE: 131

Glu Gly Val Glu Ala Ala Ala Ala Thr Val Val Val Val Val Glu
1               5                   10                  15

<210> SEQ ID NO 132
<211> LENGTH: 15
<212> TYPE: PRT
<213> ORGANISM: Homo sapiens

<400> SEQUENCE: 132

Gly Val Glu Ala Ala Ala Ala Thr Val Val Val Val Val Glu Leu
1               5                   10                  15

<210> SEQ ID NO 133
<211> LENGTH: 15
```

```
<212> TYPE: PRT
<213> ORGANISM: Homo sapiens

<400> SEQUENCE: 133

Val Thr Glu Glu Gly Val Glu Ala Ala Ala Ala Thr Val Val Val
1               5                   10                  15

<210> SEQ ID NO 134
<211> LENGTH: 15
<212> TYPE: PRT
<213> ORGANISM: Homo sapiens

<400> SEQUENCE: 134

Thr Glu Glu Gly Val Glu Ala Ala Ala Ala Thr Val Val Val Val
1               5                   10                  15

<210> SEQ ID NO 135
<211> LENGTH: 15
<212> TYPE: PRT
<213> ORGANISM: Homo sapiens

<400> SEQUENCE: 135

Val Thr Glu Glu Gly Val Glu Ala Ala Ala Ala Thr Val Val Val
1               5                   10                  15

<210> SEQ ID NO 136
<211> LENGTH: 15
<212> TYPE: PRT
<213> ORGANISM: Homo sapiens

<400> SEQUENCE: 136

Thr Glu Glu Gly Val Glu Ala Ala Ala Ala Thr Val Val Val Val
1               5                   10                  15

<210> SEQ ID NO 137
<211> LENGTH: 15
<212> TYPE: PRT
<213> ORGANISM: Homo sapiens

<400> SEQUENCE: 137

Glu Glu Gly Val Glu Ala Ala Ala Ala Thr Val Val Val Val Val
1               5                   10                  15

<210> SEQ ID NO 138
<211> LENGTH: 15
<212> TYPE: PRT
<213> ORGANISM: Homo sapiens

<400> SEQUENCE: 138

Glu Gly Val Glu Ala Ala Ala Ala Thr Val Val Val Val Val Glu
1               5                   10                  15

<210> SEQ ID NO 139
<211> LENGTH: 15
<212> TYPE: PRT
<213> ORGANISM: Homo sapiens

<400> SEQUENCE: 139

Gly Val Glu Ala Ala Ala Ala Thr Val Val Val Val Val Glu Leu
1               5                   10                  15

<210> SEQ ID NO 140
<211> LENGTH: 15
<212> TYPE: PRT
<213> ORGANISM: Homo sapiens
```

<400> SEQUENCE: 140

Val Glu Val Thr Glu Glu Gly Met Glu Ala Ala Ala Ala Thr Ala
1               5                   10                  15

<210> SEQ ID NO 141
<211> LENGTH: 15
<212> TYPE: PRT
<213> ORGANISM: Homo sapiens

<400> SEQUENCE: 141

Glu Val Thr Glu Glu Gly Met Glu Ala Ala Ala Ala Thr Ala Val
1               5                   10                  15

<210> SEQ ID NO 142
<211> LENGTH: 15
<212> TYPE: PRT
<213> ORGANISM: Homo sapiens

<400> SEQUENCE: 142

Val Thr Glu Glu Gly Met Glu Ala Ala Ala Ala Thr Ala Val Val
1               5                   10                  15

<210> SEQ ID NO 143
<211> LENGTH: 15
<212> TYPE: PRT
<213> ORGANISM: Homo sapiens

<400> SEQUENCE: 143

Thr Glu Glu Gly Met Glu Ala Ala Ala Ala Thr Ala Val Val Val
1               5                   10                  15

<210> SEQ ID NO 144
<211> LENGTH: 15
<212> TYPE: PRT
<213> ORGANISM: Homo sapiens

<400> SEQUENCE: 144

Glu Glu Gly Met Glu Ala Ala Ala Ala Thr Ala Val Val Val Val
1               5                   10                  15

<210> SEQ ID NO 145
<211> LENGTH: 15
<212> TYPE: PRT
<213> ORGANISM: Homo sapiens

<400> SEQUENCE: 145

Glu Gly Met Glu Ala Ala Ala Ala Thr Ala Val Val Val Val Glu
1               5                   10                  15

<210> SEQ ID NO 146
<211> LENGTH: 15
<212> TYPE: PRT
<213> ORGANISM: Homo sapiens

<400> SEQUENCE: 146

Gly Met Glu Ala Ala Ala Ala Thr Ala Val Val Val Val Glu Leu
1               5                   10                  15

<210> SEQ ID NO 147
<211> LENGTH: 15
<212> TYPE: PRT
<213> ORGANISM: Homo sapiens

<400> SEQUENCE: 147

Met Glu Ala Ala Ala Thr Ala Val Val Val Glu Leu Ser
1               5                   10                  15

<210> SEQ ID NO 148
<211> LENGTH: 15
<212> TYPE: PRT
<213> ORGANISM: Homo sapiens

<400> SEQUENCE: 148

Val Glu Val Thr Glu Glu Gly Met Glu Ala Ala Ala Thr Ala
1               5                   10                  15

<210> SEQ ID NO 149
<211> LENGTH: 15
<212> TYPE: PRT
<213> ORGANISM: Homo sapiens

<400> SEQUENCE: 149

Glu Val Thr Glu Glu Gly Met Glu Ala Ala Ala Thr Ala Val
1               5                   10                  15

<210> SEQ ID NO 150
<211> LENGTH: 15
<212> TYPE: PRT
<213> ORGANISM: Homo sapiens

<400> SEQUENCE: 150

Val Thr Glu Glu Gly Met Glu Ala Ala Ala Thr Ala Val Val
1               5                   10                  15

<210> SEQ ID NO 151
<211> LENGTH: 15
<212> TYPE: PRT
<213> ORGANISM: Homo sapiens

<400> SEQUENCE: 151

Thr Glu Glu Gly Met Glu Ala Ala Ala Thr Ala Val Val Val
1               5                   10                  15

<210> SEQ ID NO 152
<211> LENGTH: 15
<212> TYPE: PRT
<213> ORGANISM: Homo sapiens

<400> SEQUENCE: 152

Glu Glu Gly Met Glu Ala Ala Ala Thr Ala Val Val Val Val
1               5                   10                  15

<210> SEQ ID NO 153
<211> LENGTH: 15
<212> TYPE: PRT
<213> ORGANISM: Homo sapiens

<400> SEQUENCE: 153

Glu Gly Met Glu Ala Ala Ala Ala Thr Ala Val Val Val Glu
1               5                   10                  15

<210> SEQ ID NO 154
<211> LENGTH: 15
<212> TYPE: PRT
<213> ORGANISM: Homo sapiens

<400> SEQUENCE: 154

Gly Met Glu Ala Ala Ala Ala Thr Ala Val Val Val Val Glu Leu

```
                1               5                  10                 15
```

<210> SEQ ID NO 155
<211> LENGTH: 15
<212> TYPE: PRT
<213> ORGANISM: Homo sapiens

<400> SEQUENCE: 155

```
Met Glu Ala Ala Ala Ala Thr Ala Val Val Val Glu Leu Ser
1               5                  10                 15
```

<210> SEQ ID NO 156
<211> LENGTH: 15
<212> TYPE: PRT
<213> ORGANISM: Homo sapiens

<400> SEQUENCE: 156

```
Glu Ala Asn Thr Lys Phe Met Phe Asp Leu Phe Gln Gln Phe Lys
1               5                  10                 15
```

<210> SEQ ID NO 157
<211> LENGTH: 15
<212> TYPE: PRT
<213> ORGANISM: Homo sapiens

<400> SEQUENCE: 157

```
Ala Asn Thr Lys Phe Met Phe Asp Leu Phe Gln Gln Phe Lys Lys
1               5                  10                 15
```

<210> SEQ ID NO 158
<211> LENGTH: 15
<212> TYPE: PRT
<213> ORGANISM: Homo sapiens

<400> SEQUENCE: 158

```
Asn Thr Lys Phe Met Phe Asp Leu Phe Gln Gln Phe Lys Lys Ser
1               5                  10                 15
```

<210> SEQ ID NO 159
<211> LENGTH: 15
<212> TYPE: PRT
<213> ORGANISM: Homo sapiens

<400> SEQUENCE: 159

```
Thr Lys Phe Met Phe Asp Leu Phe Gln Gln Phe Lys Lys Ser Lys
1               5                  10                 15
```

<210> SEQ ID NO 160
<211> LENGTH: 15
<212> TYPE: PRT
<213> ORGANISM: Homo sapiens

<400> SEQUENCE: 160

```
Lys Phe Met Phe Asp Leu Phe Gln Gln Phe Lys Lys Ser Lys Glu
1               5                  10                 15
```

<210> SEQ ID NO 161
<211> LENGTH: 15
<212> TYPE: PRT
<213> ORGANISM: Homo sapiens

<400> SEQUENCE: 161

```
Phe Met Phe Asp Leu Phe Gln Gln Phe Lys Lys Ser Lys Glu Asn
1               5                  10                 15
```

<210> SEQ ID NO 162
<211> LENGTH: 15
<212> TYPE: PRT
<213> ORGANISM: Homo sapiens

<400> SEQUENCE: 162

Glu Ala Asn Thr Lys Phe Met Phe Asp Leu Phe Gln Gln Phe Lys
1               5                   10                  15

<210> SEQ ID NO 163
<211> LENGTH: 15
<212> TYPE: PRT
<213> ORGANISM: Homo sapiens

<400> SEQUENCE: 163

Ala Asn Thr Lys Phe Met Phe Asp Leu Phe Gln Gln Phe Lys Lys
1               5                   10                  15

<210> SEQ ID NO 164
<211> LENGTH: 15
<212> TYPE: PRT
<213> ORGANISM: Homo sapiens

<400> SEQUENCE: 164

Asn Thr Lys Phe Met Phe Asp Leu Phe Gln Gln Phe Lys Lys Ser
1               5                   10                  15

<210> SEQ ID NO 165
<211> LENGTH: 15
<212> TYPE: PRT
<213> ORGANISM: Homo sapiens

<400> SEQUENCE: 165

Thr Lys Phe Met Phe Asp Leu Phe Gln Gln Phe Lys Lys Ser Lys
1               5                   10                  15

<210> SEQ ID NO 166
<211> LENGTH: 15
<212> TYPE: PRT
<213> ORGANISM: Homo sapiens

<400> SEQUENCE: 166

Lys Phe Met Phe Asp Leu Phe Gln Gln Phe Lys Lys Ser Lys Glu
1               5                   10                  15

<210> SEQ ID NO 167
<211> LENGTH: 15
<212> TYPE: PRT
<213> ORGANISM: Homo sapiens

<400> SEQUENCE: 167

Phe Met Phe Asp Leu Phe Gln Gln Phe Lys Lys Ser Lys Glu Asn
1               5                   10                  15

<210> SEQ ID NO 168
<211> LENGTH: 41
<212> TYPE: DNA
<213> ORGANISM: Homo sapiens

<400> SEQUENCE: 168
tcttctttcg actttcttct ggagcatttg caaaatcaac a                        41

<210> SEQ ID NO 169
<211> LENGTH: 13

```
<212> TYPE: PRT
<213> ORGANISM: Homo sapiens

<400> SEQUENCE: 169

Lys Lys Arg Ser Glu Glu Pro Ala Asn Ala Phe Asp Val
1               5                   10

<210> SEQ ID NO 170
<211> LENGTH: 40
<212> TYPE: DNA
<213> ORGANISM: Homo sapiens

<400> SEQUENCE: 170
aggtgatgat ccgaatccta ctacagcggt ggcagctgca                            40

<210> SEQ ID NO 171
<211> LENGTH: 13
<212> TYPE: PRT
<213> ORGANISM: Homo sapiens

<400> SEQUENCE: 171

Pro Ser Ser Gly Phe Gly Val Val Ala Thr Ala Ala Ala
1               5                   10

<210> SEQ ID NO 172
<211> LENGTH: 41
<212> TYPE: DNA
<213> ORGANISM: Homo sapiens

<400> SEQUENCE: 172
aggtgatgat ccgaatccta ctacagcggt ggcagctgca g                          41

<210> SEQ ID NO 173
<211> LENGTH: 14
<212> TYPE: PRT
<213> ORGANISM: Homo sapiens

<400> SEQUENCE: 173

Pro Ser Ser Gly Phe Gly Val Val Ala Thr Ala Ala Ala Ala
1               5                   10

<210> SEQ ID NO 174
<211> LENGTH: 41
<212> TYPE: DNA
<213> ORGANISM: Homo sapiens

<400> SEQUENCE: 174
gctgccaata ttaccttcag gaattaggtt tttaattttt t                          41

<210> SEQ ID NO 175
<211> LENGTH: 14
<212> TYPE: PRT
<213> ORGANISM: Homo sapiens

<400> SEQUENCE: 175

Ser Gly Ile Asn Gly Glu Pro Ile Leu Asn Lys Ile Lys Glu
1               5                   10

<210> SEQ ID NO 176
<211> LENGTH: 179
<212> TYPE: PRT
<213> ORGANISM: Homo sapiens

<400> SEQUENCE: 176
```

```
Met Asn Ser Leu Ser Glu Ala Asn Thr Lys Phe Met Phe Asp Leu Phe
1               5                   10                  15

Gln Gln Phe Arg Lys Ser Lys Glu Asn Asn Ile Phe Tyr Ser Pro Ile
                20                  25                  30

Ser Ile Thr Ser Ala Leu Gly Met Val Leu Leu Gly Ala Lys Asp Asn
            35                  40                  45

Thr Ala Gln Gln Ile Lys Lys Val Leu His Phe Asp Gln Val Thr Glu
    50                  55                  60

Asn Thr Thr Gly Lys Ala Ala Thr Tyr His Val Asp Arg Ser Gly Asn
65                  70                  75                  80

Val His His Gln Phe Gln Lys Leu Leu Thr Glu Phe Asn Lys Ser Thr
                85                  90                  95

Asp Ala Tyr Glu Leu Lys Ile Ala Asn Lys Leu Phe Gly Glu Lys Thr
            100                 105                 110

Tyr Leu Phe Leu Gln Glu Tyr Leu Asp Ala Ile Lys Lys Phe Tyr Gln
        115                 120                 125

Thr Ser Val Glu Ser Val Asp Phe Ala Asn Ala Pro Glu Glu Ser Arg
    130                 135                 140

Lys Lys Ile Asn Ser Trp Val Glu Ser Gln Thr Asn Glu Lys Ile Lys
145                 150                 155                 160

Asn Leu Ile Pro Glu Gly Asn Ile Gly Ser Asn Thr Thr Leu Val Leu
                165                 170                 175

Val Asn Ala

<210> SEQ ID NO 177
<211> LENGTH: 178
<212> TYPE: PRT
<213> ORGANISM: Gallus gallus

<400> SEQUENCE: 177

Met Gly Ser Ile Gly Ala Ala Ser Met Glu Phe Cys Phe Asp Val Phe
1               5                   10                  15

Lys Glu Leu Lys Val His His Ala Asn Glu Asn Ile Phe Tyr Cys Pro
                20                  25                  30

Ile Ala Ile Met Ser Ala Leu Ala Met Val Tyr Leu Gly Ala Lys Asp
            35                  40                  45

Ser Thr Arg Thr Gln Ile Asn Lys Val Val Arg Phe Asp Lys Leu Pro
    50                  55                  60

Gly Phe Gly Asp Ser Ile Glu Ala Gln Cys Gly Thr Ser Val Asn Val
65                  70                  75                  80

His Ser Ser Leu Arg Asp Ile Leu Asn Gln Ile Thr Lys Pro Asn Asp
                85                  90                  95

Val Tyr Ser Phe Ser Leu Ala Ser Arg Leu Tyr Ala Glu Glu Arg Tyr
            100                 105                 110

Pro Ile Leu Pro Glu Tyr Leu Gln Cys Val Lys Glu Leu Tyr Arg Gly
        115                 120                 125

Gly Leu Glu Pro Ile Asn Phe Gln Thr Ala Ala Asp Gln Ala Arg Glu
    130                 135                 140

Leu Ile Asn Ser Trp Val Glu Ser Gln Thr Asn Gly Ile Ile Arg Asn
145                 150                 155                 160

Val Leu Gln Pro Ser Ser Val Asp Ser Gln Thr Ala Met Val Leu Val
                165                 170                 175

Asn Ala
```

DETERMINANTS OF CANCER RESPONSE TO IMMUNOTHERAPY

CROSS-REFERENCE TO RELATED APPLICATIONS

This application is a National Stage Application of PCT/US2017/052908, filed Sep. 22, 2017, which claims the benefit of and priority to U.S. Provisional Patent Application No. 62/399,212, filed Sep. 23, 2016, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Oct. 18, 2017, is named 2003080-1473_ST25.txt and is 35,544 byes in size.

BACKGROUND

Cancer immunotherapy involves supporting or stimulating a patient's immune system to attack cancer cells. Such attack is typically mediated, at least in part by the subject's T lymphocytes, or T cells. T cell activity is regulated by a T cell receptor also in concert with one or more cosignaling receptors that deliver positive or negative signals for activation. Thus, immune responses by T cells are controlled by a balance of costimulatory and inhibitory signals. These inhibitory signals, which are often referred to as "immune checkpoints" play an important role in, for example, protecting individuals from autoimmune reactions and in controlling the extent and modulating the intensity of immune reactions so that "collateral damage" can be minimized. However, research has also revealed that cancer cells can sometimes hijack these immune checkpoints to effectively suppress immune reactions that might otherwise attack the cancer. Therapeutic strategies for the treatment of cancer are therefore being developed that utilize immune checkpoint inhibition (e.g., therapy with one or more immune checkpoint inhibitors) to block the cancer's ability to avoid the patient's immune system.

Immunotherapy with immune checkpoint inhibitors is revolutionizing cancer therapy. For example, in certain melanoma patients, anti-CTLA4 therapy has provided a therapeutic for potential long-term disease control, particularly in the metastatic setting.

SUMMARY

The present invention encompasses the discovery that likelihood of a favorable response to cancer immunotherapy can be predicted. The present invention encompasses the discovery that likelihood of a favorable response to checkpoint inhibition therapy can be predicted. The present invention further comprises the discovery that a subject suffering from or susceptible to a cancer and determined to carry a serpin mutation is likely to respond favorably to immunotherapy, in particular, to treatment with an immune checkpoint modulation therapy.

In some embodiments, the invention provides methods for identifying a subject as likely to respond to treatment with immune checkpoint modulation therapy. In some embodiments, the invention provides methods of treatment for subjects suffering from or susceptible to cancer. In some embodiments, provided methods comprise a step of detecting a genetic mutation in a sample from a subject and/or of identifying a subject as a candidate for treatment with an immune checkpoint modulation therapy. In some embodiments, a genetic mutation is detected by exome sequencing.

In some embodiments, teachings of the present disclosure relate to mutation(s) in a serpin (e.g., SERPINB3, SERPINB4).

In some particular embodiments, teachings of the present disclosure relate to immune checkpoint modulation therapy modulation that targets CTLA4. In some embodiments, an immune checkpoint modulation therapy is or comprises an antibody agent. In some embodiments, an immune checkpoint modulation therapy is or comprises ipilumimab. In some embodiments, an immune checkpoint modulation therapy is or comprises tremelimumab.

BRIEF DESCRIPTION OF THE DRAWING

The following figures are presented for the purpose of illustration only, and are not intended to be limiting.

FIG. 1a shows overall survival of patients with SERPINB3 mutations in cohort 1 (n=64, p=0.005) and cohort 2 (n=110, p=0.05). FIG. 1b shows overall survival of patients with either SERPINB3 or SERPINB4 mutations in cohort 1 (p=0.01) and cohort 2 (p=0.005). FIG. 1c shows survival by SERPINB3/4 mutations in the TCGA melanoma cohort. All statistical tests are log-rank. (n=262; p=NS). FIG. 1d demonstrates the proportion of patients with SERPINB3 or SERPINB4 mutations with clinical benefit or response in cohort 1 (p=0.04) and cohort 2 (p=0.001) (Fisher's exact test). FIG. 1e shows mutation load as a function of SERPINB3 or SERPINB4 mutations in cohort 1 (p=0.002) and cohort 2 (p=0.003) (Wilcox rank-sum test).

FIG. 2a shows oncoprints of SERPINB3 and SERPINB4 mutations in Cohort 1 and Cohort 2. FIG. 2b provides diagrams showing location of mutations in SERPINB3 and SERPINB4 (data from both cohorts combined). Blue bar represents putative reactive center loop (RCL) domain. FIG. 2c shows the location of mutations on the 3-dimensional protein structure of SERPINB3. Red: mutated amino acid; blue represents the putative RCL domain. FIG. 2d shows the location of mutations on the 3-dimensional protein structure of SERPINB4.

FIG. 3(a) shows patient CR1509 (Tcov=119, TAF=0.30). FIG. 3(b) shows patient CR3665 (Tcov=246; TAF=0.20). FIG. 3(c) shows patient NR2137 (Tcov=191, TAF=0.24).

FIG. 4 shows regions of homology between human SERPINB3 and chicken egg protein ovalbumin (OVA). Residues in red represent SERPINB3 mutations identified in the presently studied patient cohorts. SERPINB3 regions highlighted in gray represent experimentally validated human HLA-binding peptides.[35] Ovalbumin regions highlighted in yellow represent functionally validated immunogenic epitopes of human T cells.[24] (An asterisk [*] indicates an exact amino acid match; a colon [:] indicates alignment of amino acid residues with strongly similar properties; a period [.] indicates alignment of amino acid residues with weakly similar properties, as described in www.ebi.ac.uk/Tools/msa/clustalo/help/faq.html#23, accessed 28 Mar. 2016.)

FIG. 5a shows expression of SERPINB3 in primary melanoma vs. regional or distant metastatic samples ($p=1.16\times10^{-13}$; Wilcoxon-rank sum test). FIG. 5b shows expression of SERPINB4 in primary melanoma vs. regional or distant metastatic samples ($p=2.99\times10^{-15}$; Wilcoxon-rank sum test).

DEFINITIONS

Figure 1A:
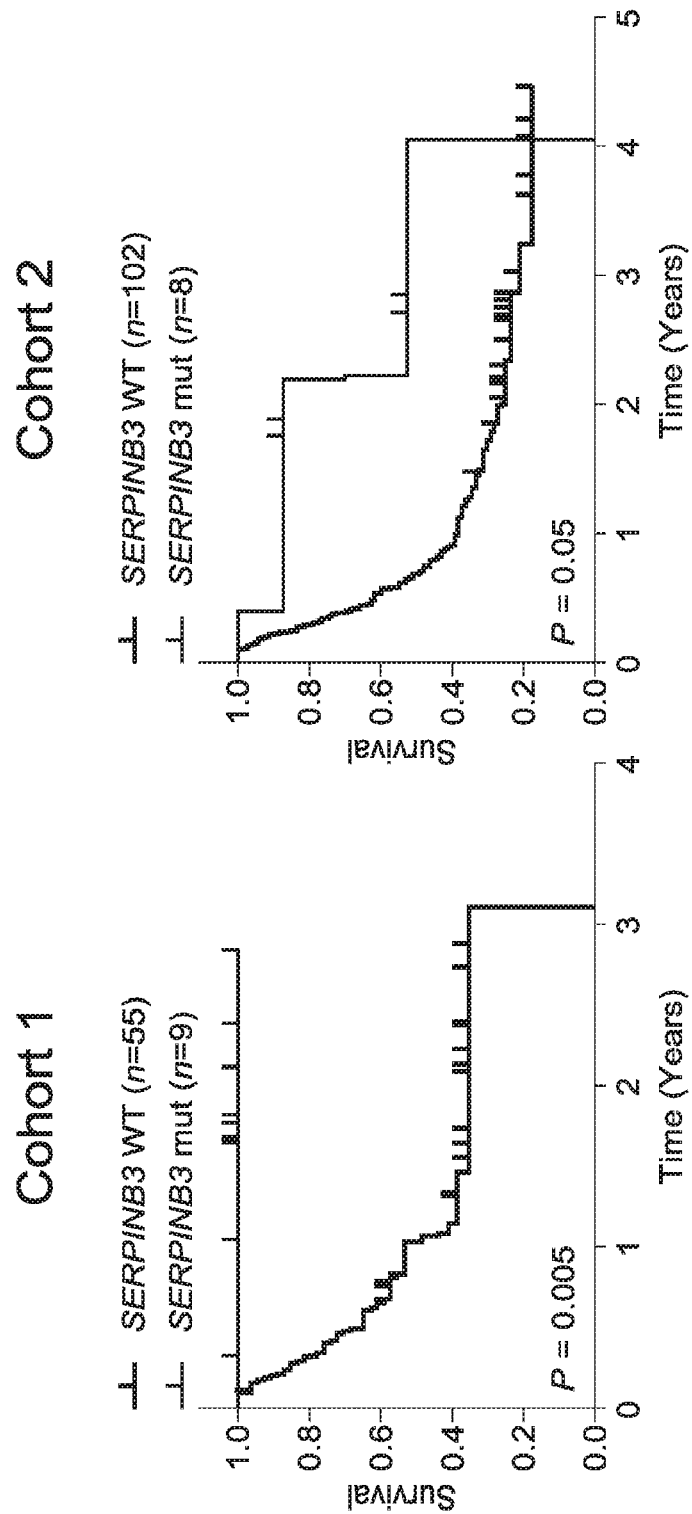
FIG. 1a-1e show that somatic mutations of SERPINB3 and SERPINB4 predict improved survival following treatment with anti-CTLA4 therapy.

Administration: As used herein, the term "administration" refers to the delivery of a composition to a subject. Administration may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal and vitreal.

Agent: In general, the term "agent", as used herein, may be used to refer to a compound or entity of any chemical class including, for example, a polypeptide, nucleic acid, saccharide, lipid, small molecule, metal, or combination or complex thereof. In appropriate circumstances, as will be clear from context to those skilled in the art, the term may be utilized to refer to an entity that is or comprises a cell or organism, or a fraction, extract, or component thereof. Alternatively or additionally, as context will make clear, the term may be used to refer to a natural product in that it is found in and/or is obtained from nature. In some instances, again as will be clear from context, the term may be used to refer to one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents may be provided as collections or libraries, for example that may be screened to identify or characterize active agents within them. In some cases, the term "agent" may refer to a compound or entity that is or comprises a polymer; in some cases, the term may refer to a compound or entity that comprises one or more polymeric moieties. In some embodiments, the term "agent" may refer to a compound or entity that is not a polymer and/or is substantially free of any polymer and/or of one or more particular polymeric moieties. In some embodiments, the term may refer to a compound or entity that lacks or is substantially free of any polymeric moiety.

Amino acid: As used herein, term "amino acid," in its broadest sense, refers to any compound and/or substance that can be incorporated into a polypeptide chain. In some embodiments, an amino acid has the general structure H2N—C(H)(R)—COOH. In some embodiments, an amino acid is a naturally occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Antibody agent: As used herein, the term "antibody agent" refers to an agent that specifically binds to a particular antigen. In some embodiments, the term encompasses any polypeptide with immunoglobulin structural elements sufficient to confer specific binding. Suitable antibody agents include, but are not limited to, human antibodies, primatized antibodies, chimeric antibodies, bi-specific antibodies, humanized antibodies, conjugated antibodies (i.e., antibodies conjugated or fused to other proteins, radiolabels, cytotoxins), Small Modular ImmunoPharmaceuticals ("SMIPs™"), single chain antibodies (a scFv, a scFv-Fc, a scFab, a scFv-zipper), cameloid antibodies, and antigen-binding portions thereof (e.g., antibody fragments, a Fab). An antibody agent may be provided and/or utilized in any appropriate format, including, for example, as an intact monoclonal antibody, a polyclonal antibody, a single domain antibody (e.g., an sdAb, shark single domain antibody {e.g., IgNAR or a fragment thereof}, a multispecific antibody (e.g., a bi-specific antibody, a bssAb, a BiTE, a bsDb, a csBsDb, a DNL-F(ab)$_2$, a scDs TaFv, a Zybody). In some embodiments, an antibody agent may be or comprise a stapled peptide, a peptidomimetic, a scaffold protein, a minibody, a monobody, a diabody, a triabody, a tetrabody, etc., an adnectin. In many embodiments, an antibody agent is or comprises a polypeptide whose amino acid sequence includes one or more structural elements recognized by those skilled in the art as a complementarity determining region (CDR); in some embodiments an antibody agent is or comprises a polypeptide whose amino acid sequence includes at least one CDR (e.g., at least one heavy chain CDR and/or at least one light chain CDR) that is substantially identical to one found in a reference antibody. In some embodiments an antibody agent is or comprises a polypeptide whose amino acid sequence includes three CDRs from at least one chain of a reference antibody (e.g., three heavy chain CDR and/or three light chain CDR) that are substantially identical to one found in a reference antibody. In some embodiments an included CDR is substantially identical to a reference CDR in that it is either identical in sequence or contains between 1-5 amino acid substitutions as compared with the reference CDR. In some embodiments an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments an included CDR is substantially identical to a reference CDR in that it shows at least 96%, 96%, 97%, 98%, 99%, or 100% sequence identity with the reference CDR. In some embodiments an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments an included CDR is substantially identical to a reference CDR in that at least one amino acid within the included CDR is substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain which is homologous or largely homologous to an immunoglobulin-binding domain. Antibody agents in accordance with the present invention may be prepared by any available means including, for example, isolation from a natural source or antibody library, recombinant production in or with a host system, chemical synthesis, etc., or combinations thereof. An antibody agent may be a member of any immunoglobulin class, including any of the human classes: IgG, IgM, IgA, IgD, and IgE. In certain embodiments, an antibody may be a member of the IgG immunoglobulin class.

Antigen: An "antigen" is a molecule or entity to which an antibody binds. In some embodiments, an antigen is or comprises a polypeptide or portion thereof. In some embodiments, an antigen is a portion of an infectious agent that is recognized by antibodies. In some embodiments, an antigen is an agent that elicits an immune response; and/or (ii) an agent that is bound by a T cell receptor (e.g., when presented by an MHC molecule) or to an antibody (e.g., produced by a B cell) when exposed or administered to an organism. In some embodiments, an antigen elicits a humoral response (e.g., including production of antigen-specific antibodies) in an organism; alternatively or additionally, in some embodiments, an antigen elicits a cellular response (e.g., involving T-cells whose receptors specifically interact with the antigen) in an organism. It will be appreciated by those skilled in the art that a particular antigen may elicit an immune response in one or several members of a target organism (e.g., mice, rabbits, primates, humans), but not in all members of the target organism species. In some embodiments, an antigen elicits an immune response in at least about 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the members of a target organism species. In some embodiments, an antigen binds to an antibody and/or T cell receptor, and may or may not induce a particular physiological response in an organism. In some embodiments, for example, an antigen may bind to an antibody and/or to a T cell receptor in vitro, whether or not such an interaction occurs in vivo. In general, an antigen may be or include any chemical entity such as, for example, a small molecule, a nucleic acid, a polypeptide, a carbohydrate, a lipid, a polymer [in some embodiments other than a biologic polymer (e.g., other than a nucleic acid or amino acid polymer)] etc. In some embodiments, an antigen is or comprises a polypeptide. In some embodiments, an antigen is or comprises a glycan. Those of ordinary skill in the art will appreciate that, in general, an antigen may be provided in isolated or pure form, or alternatively may be provided in crude form (e.g., together with other materials, for example in an extract such as a cellular extract or other relatively crude preparation of an antigen-containing source). In some embodiments, antigens utilized in accordance with the present invention are provided in a crude form. In some embodiments, an antigen is or comprises a recombinant antigen.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Combination therapy: The term "combination therapy", as used herein, refers to those situations in which two or more different pharmaceutical agents are administered in overlapping regimens so that the subject is simultaneously exposed to both agents. When used in combination therapy, two or more different agents may be administered simultaneously or separately. This administration in combination can include simultaneous administration of the two or more agents in the same dosage form, simultaneous administration in separate dosage forms, and separate administration. That is, two or more agents can be formulated together in the same dosage form and administered simultaneously. Alternatively, two or more agents can be simultaneously administered, wherein the agents are present in separate formulations. In another alternative, a first agent can be administered just followed by one or more additional agents. In the separate administration protocol, two or more agents may be administered a few minutes apart, or a few hours apart, or a few days apart.

Comparable: The term "comparable" is used herein to describe two (or more) sets of conditions, circumstances, individuals, or populations that are sufficiently similar to one another to permit comparison of results obtained or phenomena observed. In some embodiments, comparable sets of conditions, circumstances, individuals, or populations are characterized by a plurality of substantially identical features and one or a small number of varied features. Those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied. Those skilled in the art will appreciate that relative language used herein (e.g., enhanced, activated, reduced, inhibited, etc) will typically refer to comparisons made under comparable conditions.

Dosing regimen: A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, a dosing regimen is or has been correlated with a desired therapeutic outcome, when administered across a population of patients.

Epitope: as used herein, includes any moiety that is specifically recognized by an immunoglobulin (e.g., antibody or receptor) binding component. In some embodiments, an epitope is comprised of a plurality of chemical atoms or groups on an antigen. In some embodiments, such chemical atoms or groups are surface-exposed when the antigen adopts a relevant three-dimensional conformation. In some embodiments, such chemical atoms or groups are physically near to each other in space when the antigen adopts such a conformation. In some embodiments, at least some such chemical atoms are groups are physically separated from one another when the antigen adopts an alternative conformation (e.g., is linearized).

Favorable response: As used herein, the term favorable response refers to a reduction of symptoms, full or partial remission, or other improvement in disease pathophysiology. Symptoms are reduced when one or more symptoms of a particular disease, disorder or condition is reduced in magnitude (e.g., intensity, severity, etc.) and/or frequency. For purposes of clarity, a delay in the onset of a particular symptom is considered one form of reducing the frequency of that symptom. Many cancer patients with smaller tumors have no symptoms. It is not intended that the present invention be limited only to cases where the symptoms are eliminated. The present invention specifically contemplates treatment such that one or more symptoms is/are reduced (and the condition of the subject is thereby "improved"), albeit not completely eliminated. In some embodiments, a favorable response is established when a particular therapeutic regimen shows a statistically significant effect when administered across a relevant population; demonstration of a particular result in a specific individual may not be required. Thus, in some embodiments, a particular therapeutic regimen is determined to have a favorable response when its administration is correlated with a relevant desired effect.

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar.

Identity: As used herein, the term "identity" refers to the overall relatedness between polymeric molecules, e.g., between nucleic acid molecules (e.g., DNA molecules and/or RNA molecules) and/or between polypeptide molecules. Calculation of the percent identity of two nucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix.

Immune checkpoint modulation therapy: As used herein, the term "immune checkpoint modulation therapy" refers to treatment with an agent that interacts directly or indirectly with an immune checkpoint. In some embodiments, an immune checkpoint modulation therapy increases an immune effector response (e.g., cytotoxic T cell response), for example by stimulating a positive signal for T cell activation. In some embodiments, an immune checkpoint modulation therapy increases an immune effector response (e.g., cytotoxic T cell response), for example by inhibiting a negative signal for T cell activation (e.g., disinhibition). In some embodiments, an immune checkpoint modulation therapy interferes with a signal for T cell anergy. In some embodiments, an immune checkpoint modulation therapy reduces, removes, or prevents immune tolerance to one or more antigens.

Long term benefit: In general, the term "long term benefit" refers to a desirable clinical outcome, e.g., observed after administration of a particular treatment or therapy of interest, that is maintained for a clinically relevant period of time. To give but one example, in some embodiments, a long term benefit of cancer therapy is or comprises (1) no evidence of disease ("NED", for example upon radiographic assessment) and/or (2) stable or decreased volume of diseases. In some embodiments, a clinically relevant period of time is at least 1 month, at least 2 months, at least 3 months, at least 4 months, at least 5 months or more. In some embodiments, a clinically relevant period of time is at least six months. In some embodiments, a clinically relevant period of time is at least 1 year.

Marker: The term "marker", as used herein, refers to an agent whose presence or level is a characteristic of a particular tumor or metastatic disease thereof. For example, in some embodiments, the term refers to a gene expression product that is characteristic of a particular tumor, tumor subclass, stage of tumor, etc. Alternatively or additionally, in some embodiments, a presence or level of a particular marker correlates with activity (or activity level) of a particular signaling pathway, for example that may be characteristic of a particular class of tumors. The statistical significance of the presence or absence of a marker may vary depending upon the particular marker. In some embodiments, detection of a marker is highly specific in that it reflects a high probability that the tumor is of a particular subclass. Such specificity may come at the cost of sensitivity (i.e., a negative result may occur even if the tumor is a tumor that would be expected to express the marker). Conversely, markers with a high degree of sensitivity may be less specific that those with lower sensitivity. According to the present invention a useful marker need not distinguish tumors of a particular subclass with 100% accuracy.

Modulator: The term "modulator" is used to refer to an entity whose presence in a system in which an activity of interest is observed correlates with a change in level and/or nature of that activity as compared with that observed under otherwise comparable conditions when the modulator is absent. In some embodiments, a modulator is an activator, in that activity is increased in its presence as compared with that observed under otherwise comparable conditions when the modulator is absent. In some embodiments, a modulator is an inhibitor, in that activity is reduced in its presence as compared with otherwise comparable conditions when the modulator is absent. In some embodiments, a modulator interacts directly with a target entity whose activity is of interest. In some embodiments, a modulator interacts indirectly (i.e., directly with an intermediate agent that interacts with the target entity) with a target entity whose activity is of interest. In some embodiments, a modulator affects level of a target entity of interest; alternatively or additionally, in some embodiments, a modulator affects activity of a target entity of interest without affecting level of the target entity. In some embodiments, a modulator affects both level and activity of a target entity of interest, so that an observed difference in activity is not entirely explained by or commensurate with an observed difference in level.

Neoepitope: As used herein the term "neoepitope" or "neo antigen" is understood in the art to refer to an epitope that emerges or develops in a subject after exposure to or occurrence of a particular event (e.g., development or progression of a particular disease, disorder or condition, e.g., infection, cancer, stage of cancer, etc). As used herein, a neoepitope is one whose presence and/or level is correlated with exposure to or occurrence of the event. In some embodiments, a neoepitope is one that triggers an immune response against cells that express it (e.g., at a relevant level). In some embodiments, a neopepitope is one that triggers an immune response that kills or otherwise destroys cells that express it (e.g., at a relevant level). In some embodiments, a relevant event that triggers a neoepitope is or comprises somatic mutation in a cell. In some embodiments, a neoepitope is not expressed in non-cancer cells to a level and/or in a manner that triggers and/or supports an immune response (e.g., an immune response sufficient to target cancer cells expressing the neoepitope).

No benefit: As used herein, the phrase "no benefit" is used to refer to absence of detectable clinical benefit (e.g., in response to administration of a particular therapy or treatment of interest). In some embodiments, absence of clinical benefit refers to absence of statistically significant change in any particular symptom or characteristic of a particular disease, disorder, or condition. In some embodiments, absence of clinical benefit refers to a change in one or more symptoms or characteristics of a disease, disorder, or condition, that lasts for only a short period of time such as, for example, less than about 6 months, less than about 5 months, less than about 4 months, less than about 3 months, less than about 2 months, less than about 1 month.

Patient: As used herein, the term "patient" or "subject" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. In some embodiments, a patient is suffering from or susceptible to one or more disorders or conditions. In some embodiments, a patient displays one or more symptoms of a disorder or condition. In some embodiments, a patient has been diagnosed with one or more disorders or conditions. In some embodiments, the disorder or condition is or includes cancer, or presence of one or more tumors. In some embodiments, the disorder or condition is metastatic cancer.

Polypeptide: As used herein, a "polypeptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally.

Prognostic and predictive information: As used herein, the terms prognostic and predictive information are used interchangeably to refer to any information that may be used to indicate any aspect of the course of a disease or condition either in the absence or presence of treatment. Such information may include, but is not limited to, the average life expectancy of a patient, the likelihood that a patient will survive for a given amount of time (e.g., 6 months, 1 year, 5 years, etc.), the likelihood that a patient will be cured of a disease, the likelihood that a patient's disease will respond to a particular therapy (wherein response may be defined in any of a variety of ways). Prognostic and predictive information are included within the broad category of diagnostic information.

Protein: As used herein, the term "protein" refers to a polypeptide (i.e., a string of at least two amino acids linked to one another by a peptide bond(s)). Proteins may include moieties other than amino acids (e.g., may be glycoproteins, proteoglycans, lipidated polypeptides, PEGylated polypeptides, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids (e.g., synthetic amino acids), and combinations thereof. The term "peptide" is generally used to refer to a polypeptide having a length of less than about 100 amino acids, less than about 50 amino acids, less than 20 amino acids, or less than 10 amino acids.

Reference: As used herein describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Response: As used herein, a response to treatment may refer to any beneficial alteration in a subject's condition that occurs as a result of or correlates with treatment. Such alteration may include stabilization of the condition (e.g., prevention of deterioration that would have taken place in the absence of the treatment), amelioration of symptoms of the condition, and/or improvement in the prospects for cure of the condition, etc. It may refer to a subject's response or to a tumor's response. Tumor or subject response may be measured according to a wide variety of criteria, including clinical criteria and objective criteria. Techniques for assessing response include, but are not limited to, clinical examination, positron emission tomography, chest X-ray, CT scan, MRI, ultrasound, endoscopy, laparoscopy, presence or level of tumor markers in a sample obtained from a subject, cytology, and/or histology. Many of these techniques attempt to determine the size of a tumor or otherwise determine the total tumor burden. Methods and guidelines for assessing response to treatment are discussed in Therasse et. al., "New guidelines to evaluate the response to treatment in solid tumors", European Organization for Research and Treatment of Cancer, National Cancer Institute of the United States, National Cancer Institute of Canada, *J. Nat'l. Cancer Inst.*, 2000, 92(3):205-216. The exact response criteria can be selected in any appropriate manner, provided that when comparing groups of tumors and/or patients, the groups to be compared are assessed based on the same or comparable criteria for determining response rate. One of ordinary skill in the art will be able to select appropriate criteria.

Sample: As used herein, the term "sample" refers to a substance obtained from a subject and may include, but is not limited to, any or all of the following: a cell or cells, a portion of tissue, blood, serum, ascites, urine, saliva, and other body fluids, secretions, or excretions. The term "sample" also includes any material derived by processing such a sample. Derived samples may include serum derived from whole blood samples. nucleotide molecules or polypeptides extracted from the sample or obtained by subjecting the sample to techniques such as amplification or reverse transcription of mRNA, etc.

Stage of cancer: As used herein, the term "stage of cancer" refers to a qualitative or quantitative assessment of the level of advancement of a cancer. Criteria used to determine the stage of a cancer include, but are not limited to, the size of the tumor and the extent of metastases (e.g., localized or distant).

Subject: As used herein, the term "subject" or "patient" refers to any organism upon which embodiments of the invention may be used or administered, e.g., for experimental, diagnostic, prophylactic, and/or therapeutic purposes. Typical subjects include animals (e.g., mammals such as mice, rats, rabbits, non-human primates, and humans, insects, worms, etc.).

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, or condition (e.g., a cancer) has been diagnosed with and/or exhibits one or more symptoms of the disease, disorder, or condition. In some embodiments, an individual who is suffering from cancer has cancer, but does not display any symptoms of cancer and/or has not been diagnosed with a cancer.

Susceptible to: An individual who is "susceptible to" a disease, disorder, or condition (e.g., cancer) is at risk for developing the disease, disorder, or condition. In some embodiments, an individual who is susceptible to a disease, disorder, or condition does not display any symptoms of the disease, disorder, or condition. In some embodiments, an individual who is susceptible to a disease, disorder, or condition has not been diagnosed with the disease, disorder, and/or condition. In some embodiments, an individual who is susceptible to a disease, disorder, or condition is an individual who displays conditions associated with development of the disease, disorder, or condition. In some embodiments, a risk of developing a disease, disorder, and/or condition is a population-based risk.

Target cell or target tissue: As used herein, the terms "target cell" or "target tissue" refer to any cell, tissue, or organism that is affected by a condition described herein and to be treated, or any cell, tissue, or organism in which a protein involved in a condition described herein is expressed. In some embodiments, target cells, target tissues, or target organisms include those cells, tissues, or organisms in which there is a detectable amount of immune checkpoint signaling and/or activity. In some embodiments, target cells, target tissues, or target organisms include those cells, tissues or organisms that display a disease-associated pathology, symptom, or feature.

Therapeutic regimen: As used herein, the term "therapeutic regimen" refers to any method used to partially or completely alleviate, ameliorate, relieve, inhibit, prevent, delay onset of, reduce severity of and/or reduce incidence of one or more symptoms or features of a particular disease, disorder, and/or condition. It may include a treatment or series of treatments designed to achieve a particular effect, e.g., reduction or elimination of a detrimental condition or disease such as cancer. The treatment may include administration of one or more compounds either simultaneously, sequentially or at different times, for the same or different amounts of time. Alternatively, or additionally, the treatment may include exposure to radiation, chemotherapeutic agents, hormone therapy, or surgery. In addition, a "treatment regimen" may include genetic methods such as gene therapy, gene ablation or other methods known to reduce expression of a particular gene or translation of a gene-derived mRNA.

Therapeutic agent: As used herein, the phrase "therapeutic agent" refers to any agent that, when administered to a subject, has a therapeutic effect and/or elicits a desired biological and/or pharmacological effect.

Therapeutically effective amount: As used herein, the term "therapeutically effective amount" refers to an amount of an agent (e.g., an immune checkpoint modulation therapy) that confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic agent or composition effective to treat, ameliorate, or prevent a desired disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount is commonly administered in a dosing regimen that may comprise multiple unit doses. For any particular therapeutic agent, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the subject; the time of administration, route of administration, and/or rate of excretion or metabolism of the specific fusion protein employed; the duration of the treatment; and like factors as is well known in the medical arts.

Treatment: As used herein, the term "treatment" (also "treat" or "treating") refers to any administration of a substance (e.g., provided compositions) that partially or completely alleviates, ameliorates, relieves, inhibits, delays onset of, reduces severity of, and/or reduces incidence of one or more symptoms, features, and/or causes of a particular disease, disorder, and/or condition (e.g., cancer). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Wild-type: As used herein, the term "wild-type" has its art-understood meaning that refers to an entity having a structure and/or activity as found in nature in a "normal" (in contrasted with mutant, diseased, altered, etc.) state or context. Those of ordinary skill in the art will appreciate that wild-type genes and polypeptides often exist in multiple different forms (e.g., alleles).

DETAILED DESCRIPTION OF CERTAIN EMBODIMENTS

The present disclosure encompasses the discovery that mutations in serpins contribute to the anti-tumor immune response of immune checkpoint modulation therapies. The present disclosure, among other things, provides methods of treating patients that have been identified to have cancer harboring a serpin mutation with immune checkpoint modulation therapy. The present disclosure, among other things, provides technologies for establishing and/or detecting responsiveness of particular subjects (e.g., subjects carrying a particular serpin mutation) to particular immune checkpoint blockage therapy.

Serpins

In some embodiments the present disclosure relates to serine protease inhibitors also known as serpins. Serpins are a superfamily of proteins typically identified by their protease inhibition activity and/or by certain characteristic sequence elements. Most serpins are protease inhibitors, targeting extracellular, chymotrypsin-like serine proteases. Serpin proteases possess a nucleophilic serine residue in a catalytic triad in their active site. Examples include thrombin, trypsin, and human neutrophil elastase. Serpins act as irreversible, suicide inhibitors by trapping an intermediate of the protease's catalytic mechanism. Through their protease inhibition activity serpins regulate a wide array of biological processes including coagulation and inflammation.

Although most serpins control proteolytic cascades, some proteins with a serpin structure are not enzyme inhibitors, but instead perform diverse functions such as storage (e.g., ovalbumin), transport as in hormone carriage proteins (thyroxine-binding globulin, cortisol-binding globulin) and molecular chaperoning (HSP47). The term serpin is used to describe these members as well, despite their non-inhibitory function, since they are evolutionarily related.

The human genome encodes 16 serpin clades, termed serpinA through serpinP, including 29 inhibitory and 7 non-inhibitory serpin proteins. Clade B serpins have shorter C and N termini than typical A members and also lack the secretory signal peptide sequence. There are 13 human genes in clade B (SERPINB1-SERPINB13) and one pseudogene. Serpins in clade B are important in inflammation and immune system function as well as mucous production. SERPINB1, B6, B7, and B9 are involved in immune system function with roles in neutrophil and megakaryocyte development, as well as in the inhibition of the cytotoxic granule protease granzyme B.[43]

In some embodiments, the present disclosure relates to clade B serpins. In some embodiments, the present disclosure relates to SERPINB3 and or SERPINB4. SERPINB3 and its close homolog SERPINB4 have roles in mucous production and are expressed in epithelial tissues, such as tongue, tonsils, uterus, cervix, and vagina as well as in the upper respiratory tract and thymus.[43] SERPINB3 is a serine protease inhibitor that functions in apoptosis and autoimmunity.[11-14] SERPINB3 is a human homologue of chicken ovalbumin protein (OVA), which is a classic model antigen. SERPIN B4 is a close human homologue of SERPINB3 with which it shares 92% protein sequence identity. SERPINB3 and SERPINB4 have overlapping functions and are involved in both oncogenesis and immunity.[14-16]

Serpin Mutations

In some embodiments, the present disclosure relates to serpin mutations. In some embodiments, the present disclosure relates to germ line mutations in a serpin gene. A germ line mutation is a mutation found in sperm or ova. In some embodiments the present disclosure relates to somatic mutations in a serpin gene. Somatic mutations comprise DNA alterations in non-germline cells and commonly occur in cancer cells. In some embodiments, a mutation encompassed by the present disclosure may be or comprise a frame shift mutation, a splice variant, a missense mutation, a nonsense mutation, an insertion, a deletion, or a combination thereof. In some embodiments, a serpin mutation may affect the level, activity, and/or form (e.g., post translational modification) of a serpin. In some embodiments, a serpin mutation encompassed by the present disclosure may be a mutation in a regulatory element associated with serpin (e.g., promoter, enhancer, etc.).

In some embodiments the present disclosure relates to mutations in SERPINB3 and/or SERPINB4. SERPINB3 has been identified as a significantly and recurrently mutated gene in melanoma by the Cancer Genome Atlas (TCGA) and other groups, suggesting it as a driver of oncogenesis.[11-17] Serpins are known to exhibit anti-apoptotic functions,[13] including suppression of ultraviolet light-induced apoptosis in human keratinocytes.[18] There are also a number of possible mechanisms by which mutations in SERPINB3/B4 may influence tumor immunogenicity. Mutations in various serpin family proteins are known to cause misfolding and self-polymerization, leading to the formation of inflammatory aggregates or plaques. These, in turn, may function as targets in various autoimmune diseases, including systemic lupus erythematosus and psoriasis.[13,14,19,20] Serpin polymers can also induce autophagy, thereby potentially enhancing auto-antigen presentation.[13,21] Therefore, mutant SERPINB3/4 may act as both a driver of tumorigenesis and/or also as an immunodeterminant, similar to mutant IDH1 in glioma.[22] In some embodiments, the present disclosure relates to SERPINB3 and SERPIN B4 mutations listed in Table 1.

In some embodiments, serpin mutations can be detected in a biological sample from a subject. In some embodiments a biological sample can be a cell or cells, a portion of tissue, blood, serum, ascites, urine, saliva, and other body fluids, secretions, or excretions. In some embodiments, mutations may be detected in a nucleic acid (e.g., DNA, RNA). In some embodiments, mutations may be detected in circulating tumor DNA (ctDNA). In some embodiments, mutations may be detected in a polypeptide. In some embodiments, mutations may be detected in post translational modifications made to a polypeptide (e.g., phosphorylation, ubiquitiniation, SUMOylation, acetylation etc.). In some embodiments, mutations may be detected by means known to one of skill in the art. In some embodiments, mutations can be detected by, for example, PCR, sequencing, (e.g exome sequencing, ultra deep sequencing, RNA-seq, whole genome sequencing, etc.) blotting (e.g., Western, Northern, Southern, mass spectrometry.

TABLE 1

| Dataset | Gene | Sample | Genomic Position | Base Pair Change | Amino Acid Change | SIFT Prediction | Polyphen2 HVAR prediction |
| --- | --- | --- | --- | --- | --- | --- | --- |
| Cohort 1 | SERPINB3 | CR3665 | 18; 61323016 | C-->T | V350K | tolerated | benign |
| Cohort 1 | SERPINB3 | CRNR4941 | 18; 61325851 | G-->A | A122V | tolerated | benign |
| Cohort 1 | SERPINB3 | CR1509 | 18; 61325797 | G-->A | P140L | damaging | benign |
| Cohort 1 | SERPINB3 | LSDNR1120 | 18; 61323007 | C-->T | G353R | tolerated | benign |
| Cohort 1 | SERPINB3 | CR22640 | 18; 61324207 | G-->A | S209F | damaging | possibly damaging |
| Cohort 1 | SERPINB3 | NR2137 | 18; 61324626 | G-->A | P164S | tolerated | probably damaging |
| Cohort 1 | SERPINB3 | PR4077 | 18; 61322974 | G-->A | H364Y | tolerated | benign |
| Cohort 1 | SERPINB3 | PR4035 | 18; 61326748 | C-->T | G79E | tolerated | benign |
| Cohort 1 | SERPINB3 | CR4880 | 18; 61323012 | C-->G | G351A | tolerated | benign |
| Cohort 1 | SERPINB3 | CR6161 | 18; 61305325 | C-->T | M267I | tolerated | benign |
| Cohort 1 | SERPINB4 | CR6161 | 18; 61306534 | G-->A | S218F | tolerated | benign |
| Cohort 1 | SERPINB4 | SD1494 | 18; 61309109 | C-->T | G79E | tolerated | benign |
| Cohort 1 | SERPINB4 | SD7357 | 18; 61309061 | G-->A | S95F | tolerated | benign |
| Cohort 1 | SERPINB4 | NR9521 | 18; 61304963 | G-->A | S388L | damaging | probably damaging |
| Cohort 1 | SERPINB4 | CR9699 | 18; 61310397 | G-->A | H74Y | damaging | possibly damaging |
| Cohort 1 | SERPINB4 | NR9449 | 18; 61306511 | C-->T | D226N | tolerated | possibly damaging |
| Cohort 1 | SERPINB4 | LSD4744 | 18; 61305285 | C-->T | D281N | tolerated | benign |
| Cohort 1 | SERPINB4 | CR04885 | 18; 61306490 | C-->T | E233K | damaging | probably damaging |
| Cohort 2 | SERPINB3 | Pat124 | 18; 61322899 | A-->T | S389T | damaging | benign |
| Cohort 2 | SERPINB3 | Pat126 | 18; 61325839 | A-->C | F126C | damaging | benign |
| Cohort 2 | SERPINB3 | Pat138 | 18; 61323000 | G-->A | S355L | tolerated | possibly damaging |
| Cohort 2 | SERPINB3 | Pat16 | 18; 61322986 | T-->C | N360D | tolerated | benign |
| Cohort 2 | SERPINB3 | Pat174 | 18; 61324136 | C-->T | E233K | tolerated | probably damaging |
| Cohort 2 | SERPINB3 | Pat63 | 18; 61325785 | C-->T | R144Q | damaging | benign |
| Cohort 2 | SERPINB3 | Pat79 | 18; 61325864 | C-->T | E118K | tolerated | possibly damaging |
| Cohort 2 | SERPINB3 | Pat88 | 18; 61324085 | C-->T | E250K | damaging | probably damaging |
| Cohort 2 | SERPINB3 | Pat88 | 18; 61324626 | G-->A | P164S | tolerated | probably damaging |
| Cohort 2 | SERPINB4 | Pat02 | 18; 61306903 | C-->T | E193K | tolerated | benign |
| Cohort 2 | SERPINB4 | Pat117 | 18; 61310415 | C-->T | E68K | tolerated | benign |
| Cohort 2 | SERPINB4 | Pat11 | 18; 61305083 | G-->A | A348V | damaging | benign |
| Cohort 2 | SERPINB4 | Pat11 | 18; 61309005 | G-->A | Q114* | | |
| Cohort 2 | SERPINB4 | Pat138 | 18; 61305105 | C-->T | V341M | damaging | benign |
| Cohort 2 | SERPINB4 | Pat159 | 18; 61310753 | C-->T | R20K | tolerated | benign |
| Cohort 2 | SERPINB4 | Pat71 | 18; 61309110 | C-->T | G79R | damaging | probably damaging |
| Cohort 2 | SERPINB4 | Pat74 | 18; 61310646 | C-->T | SPLICE_SITE_DONOR | | |
| Cohort 2 | SERPINB4 | Pat88 | 18; 61310448 | G-->A | L57F | tolerated | probably damaging |

TABLE 1-continued

| Dataset | Gene | Sample | GERP RS | Mutation Assessor | MetaSVM | MetaLR |
|---|---|---|---|---|---|---|
| Cohort 1 | SERPINB3 | CR3665 | 0.109 | neutral | tolerated | tolerated |
| Cohort 1 | SERPINB3 | CRNR4941 | 1.81 | neutral | tolerated | tolerated |
| Cohort 1 | SERPINB3 | CR1509 | 2.97 | low | tolerated | tolerated |
| Cohort 1 | SERPINB3 | LSDNR1120 | −5.34 | neutral | tolerated | tolerated |
| Cohort 1 | SERPINB3 | CR22640 | 2.64 | low | damaging | damaging |
| Cohort 1 | SERPINB3 | NR2137 | 2.74 | low | tolerated | damaging |
| Cohort 1 | SERPINB3 | PR4077 | −2.43 | low | tolerated | tolerated |
| Cohort 1 | SERPINB3 | PR4035 | −3.83 | neutral | tolerated | tolerated |
| Cohort 1 | SERPINB3 | CR4880 | −5.99 | neutral | tolerated | tolerated |
| Cohort 1 | SERPINB3 | CR6161 | −3.77 | neutral | tolerated | tolerated |
| Cohort 1 | SERPINB4 | CR6161 | −6.51 | neutral | tolerated | tolerated |
| Cohort 1 | SERPINB4 | SD1494 | −2.26 | neutral | tolerated | tolerated |
| Cohort 1 | SERPINB4 | SD7357 | 2.88 | medium | tolerated | damaging |
| Cohort 1 | SERPINB4 | NR9521 | 4.51 | medium | damaging | damaging |
| Cohort 1 | SERPINB4 | CR9699 | 0.672 | neutral | tolerated | tolerated |
| Cohort 1 | SERPINB4 | NR9449 | 4.17 | low | tolerated | damaging |
| Cohort 1 | SERPINB4 | LSD4744 | −8.49 | neutral | tolerated | tolerated |
| Cohort 1 | SERPINB4 | CR04885 | 4.17 | medium | tolerated | tolerated |
| Cohort 2 | SERPINB3 | Pat124 | 1.71 | medium | tolerated | tolerated |
| Cohort 2 | SERPINB3 | Pat126 | −5.95 | medium | tolerated | damaging |
| Cohort 2 | SERPINB3 | Pat138 | −3.06 | medium | tolerated | tolerated |
| Cohort 2 | SERPINB3 | Pat16 | −5.92 | neutral | tolerated | tolerated |
| Cohort 2 | SERPINB3 | Pat174 | 2.64 | medium | damaging | damaging |
| Cohort 2 | SERPINB3 | Pat63 | 0.091 | low | tolerated | tolerated |
| Cohort 2 | SERPINB3 | Pat79 | −1.12 | low | tolerated | damaging |
| Cohort 2 | SERPINB3 | Pat88 | 2.64 | medium | damaging | damaging |
| Cohort 2 | SERPINB3 | Pat88 | 2.74 | low | tolerated | damaging |
| Cohort 2 | SERPINB4 | Pat02 | −0.112 | neutral | tolerated | tolerated |
| Cohort 2 | SERPINB4 | Pat117 | −1.44 | neutral | tolerated | tolerated |
| Cohort 2 | SERPINB4 | Pat11 | 0.349 | neutral | tolerated | tolerated |
| Cohort 2 | SERPINB4 | Pat11 | 1.62 | | | |
| Cohort 2 | SERPINB4 | Pat138 | 3.38 | neutral | tolerated | tolerated |
| Cohort 2 | SERPINB4 | Pat159 | 0.424 | neutral | tolerated | tolerated |
| Cohort 2 | SERPINB4 | Pat71 | 3.39 | low | tolerated | damaging |
| Cohort 2 | SERPINB4 | Pat74 | 3.76 | | | |
| Cohort 2 | SERPINB4 | Pat88 | 1.07 | medium | tolerated | damaging |

Subjects

In some embodiments, the present disclosure relates to the screening and/or treatment of particular subjects. In some embodiments, a subject of the present disclosure may be an animal. In some embodiments, a subject of the present disclosure may be a human. In some embodiments, a subject of the present disclosure may be suffering from or susceptible to cancer. In some embodiments, a subject of the present disclosure may be characterized by particular somatic and/or germ line mutations. In some embodiments, a subject of the present disclosure may be characterized by one or more mutations in a serpin. In some embodiments, a subject of the present disclosure may be characterized by one or more mutations in SERPINB3 and or SERPINB4. In some embodiments, a subject may not display symptoms of the cancer.

Cancers

Figure 6:
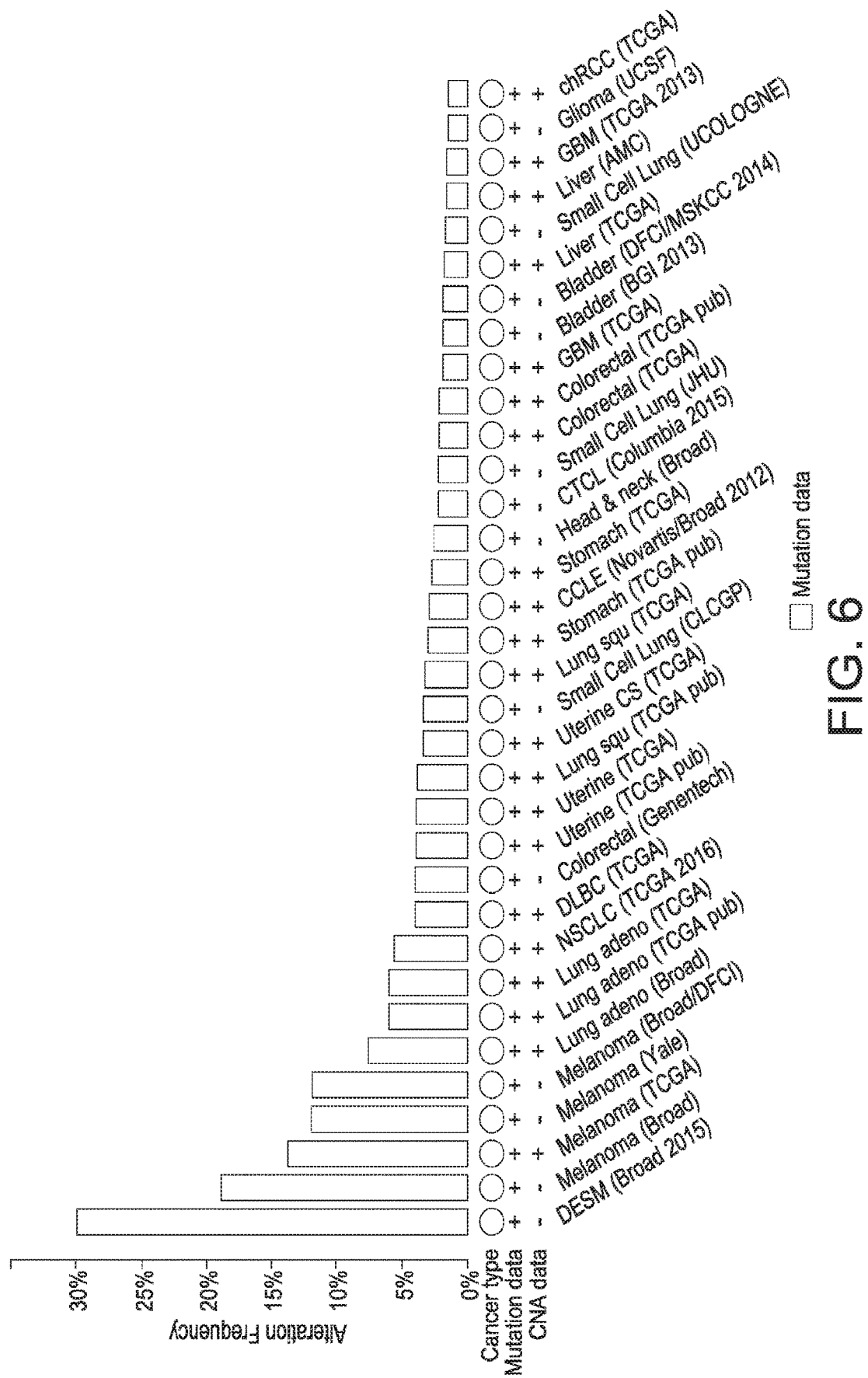
FIG. 6 shows the serpin alteration frequency across various cancer types.
Figure 6:
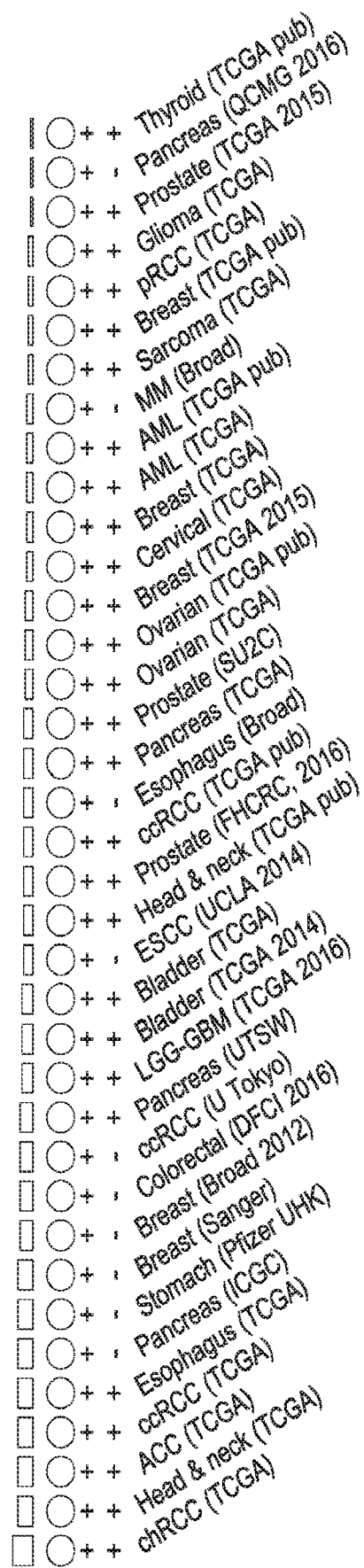
Figure 6:
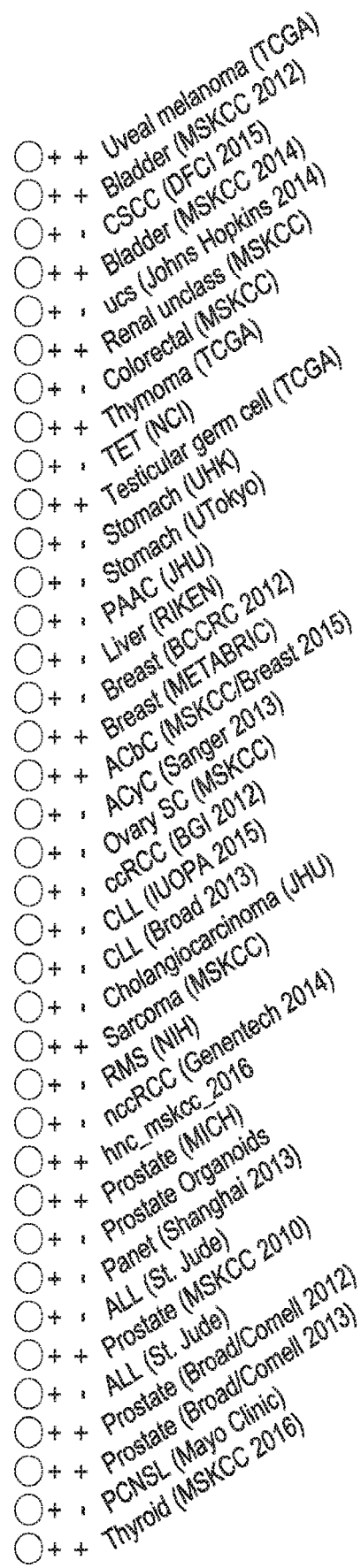

In some embodiments, the present disclosure relates to treatment of cancer. In some embodiment, the present disclosure relates to the treatment of any cancer characterized by a sensitivity to immune checkpoint modulation therapy. In some embodiments, the present disclosure relates to the treatment of any cancer characterized by a serpin mutation. In some embodiments, the present disclosure relates to the treatment of any cancer characterized by In some embodiments, the present disclosure relates to the treatment of cancers described in FIG. 6. In some embodiments, the present disclosure relates to the treatment of adenoid cystic carcinoma, bladder cancer, breast cancer, colorectal cancer, esophageal cancer, glioma, glioblastoma (GBM), head and neck cancer, leukemia (e.g., myeloid and lymphoid), liver cancer, lung cancer, lymphoma, multiple myeloma, ovarian cancer, pancreatic cancer, prostate cancer, renal cancer (e.g., clear cell renal cell carcinoma (ccRCC); chromophobe renal cell carcinoma (chRCC), papillary renal cell carcinoma (pRCC)), sarcoma, stomach cancer, thyroid cancer, and uterine cancer.

Melanoma

In some embodiments, the present disclosure relates particularly to the treatment of melanoma. Melanoma, also known as malignant melanoma, is a type of cancer that develops from pigment-containing cells known as melanocytes. Melanomas occur commonly in the skin but may occur in the mouth, intestines, or eye.

The primary cause of melanoma is ultraviolet light (UV) exposure. The UV light may be from either the sun or from other sources, such as tanning devices. Subjects with many moles, a history of affected family members, and who have poor immune function are at greater relative risk for developing melanoma. A number of rare genetic defects such as xeroderma pigmentosum also increase risk. Diagnosis is by biopsy of any concerning skin lesion.

As used herein, the term melanoma may include Lentigo maligna, Lentigo maligna melanoma, Superficial spreading melanoma, Acral lentiginous melanoma, Mucosal melanoma, Nodular melanoma, Polypoid melanoma, Desmoplastic melanoma, Amelanotic melanoma, Soft-tissue melanoma, Melanoma with small nevus-like cells, Melanoma with features of a Spitz nevus, and Uveal melanoma. As used herein, the term melanoma may include any stage, level, thickness or depth of cancer.

Immune Checkpoint Modulation

In some embodiments, the present disclosures relates to the use of agents for modulation of immune checkpoints. Immune checkpoints refer to inhibitory pathways of the immune system that are responsible for maintaining self-tolerance and modulating the duration and amplitude of physiological immune responses.

Certain cancer cells thrive by taking advantage of immune checkpoint pathways as a major mechanism of immune resistance, particularly with respect to T cells that are specific for tumor antigens. For example, certain cancer cells may overexpress one or more immune checkpoint proteins responsible for inhibiting a cytotoxic T cell response. Thus, immune checkpoint modulation therapy may be administered to overcome the inhibitory signals and permit and/or augment an immune attack against cancer cells. Immune checkpoint modulation therapy may facilitate immune cell responses against cancer cells by decreasing, inhibiting, or abrogating signaling by negative immune response regulators (e.g., CTLA4), or may stimulate or enhance signaling of positive regulators of immune response (e.g., CD28).

Immunotherapy agents targeted to immune checkpoint modulation therapy may be administered to encourage immune attack targeting cancer cells. In some embodiments, immunotherapy agents may be or include nucleic acid agents (e.g., siRNA or antisense oligonucleotides. In some embodiments, immunotherapy agents may be or include antibody agents that target (e.g., are specific for) immune checkpoint modulation therapies. Examples of immunotherapy agents targeted to immune checkpoint modulation therapy include agents targeting one or more of A2AR, B7-H4, BTLA, CTLA-4, CD28, CD40, CD137, GITR, IDO, KIR, LAG-3, PD-1, PD-L1, OX40, TIM-3, VISTA.

Specific examples of antibody agents may include monoclonal antibodies. Certain monoclonal antibodies targeting immune checkpoint modulation therapies are available. For instance, ipilimumab targets CTLA-4; tremelimumab targets CTLA-4; pembrolizumab targets PD-1, nivolumab targets PD-1; etc.

In some embodiments, ipilimumab is indicated for treatment of unresectable or metastatic melanoma as well as adjuvant treatment of patients with cutaneous melanoma with pathologic involvement of regional lymph nodes of more than 1 mm who have undergone complete resection, including total lymphadenectomy. For treatment of unresectable or metastatic melanoma 3 mg/kg of ipilimumab can be administered intravenously over 90 minutes every 3 weeks for a total of 4 doses. For treatment of melanoma as adjuvant treatment 10 mg/kg of ipilimumab can be administered intravenously over 90 minutes every 3 weeks for 4 doses, followed by 10 mg/kg every 12 weeks for up to 3 years or until documented disease recurrence or unacceptable toxicity of 4 doses.

In some embodiments, tremelimumab can be used to treat melanoma through intravenous administration at a dose of 15 mg/kg once every 90 days. A subject may receive up to 8 doses (8 cycles) in a 24-month period until progression of disease or intolerable toxicity.

In some embodiments, pembrolizumab can be used to treat patients with unresectable or metastatic melanoma, metastatic non-small cell lung cancer (NSCLC) whose tumors express PD-L1 and who have disease progression on or after platinum-containing chemotherapy, patients with recurrent or metastatic head and neck squamous cell carcinoma (HNSCC) with disease progression on or after platinum-containing chemotherapy. Pembrolizumab, when used to treat melanoma and NSCLC, can be administered at 2 mg/kg every 3 weeks. Pembrolizumab, when used to treat HNSCC, can be administered at 200 mg every 3 weeks. Pembrolizumab is administered as an intravenous solution over 30 minutes.

In some embodiments, nivolumab can be used to treat patients with unresectable or metastatic melanoma, metastatic non-small cell lung cancer (NSCLC), advanced renal cell carcinoma, or classical Hodgkin lymphoma. Nivolumab can be administered as an intravenous infusion of 240 mg over 60 minutes every 2 weeks until disease progression or unacceptable toxicity.

Epitopes

In some embodiments, the present disclosure relates to use of agents for modulation of an immune response to a particular epitope or antigen. In some embodiments, the particular epitope or antigen may be or comprise a neoepitope (i.e., an epitope that arises during tumor development and/or proliferation, so that its presence is correlated with a stage of or event in cancer progression). In some embodiments, an epitope (e.g., a neoepitope) contemplated by the present disclosure in a serpin protein. In some embodiments, an epitope or neoepitope in a serpin protein comprises a mutation in the serpin protein. In some embodiments, an epitope or neoepitope contemplated by the present disclosure is or comprises a mutation listed in Table 1. In some embodiments, an epitope or neoepitope contemplated by the present disclosure is or comprises an epitope listed in Table 4 or Table 5.

In some embodiments, the present disclosure provides compositions comprising or encoding an epitope or neoepitope. In some embodiments, such a composition can include, but are not limited to, nucleic acids (e.g., DNA, RNA) and polypeptides. In some embodiments such a composition may be or encode an immunogenic peptide. In some embodiments, an immunogenic peptide is a peptide that, when administered to a subject results in an increased level of immune response relative to a level of immune response absent administration of the immunogenic peptide.

In some embodiments, a relevant epitope or neoepitope is detected in a patient suffering from or susceptible to cancer. In some embodiments, a composition comprising an epitope or neoepitope as described herein is administered to a subject in whom the epitope or neoepitope has been detected.

Detection of Neoepitopes

In some embodiments, cancers may be screened to detect neoepitopes using any of a variety of known technologies. In some embodiments, neoepitopes, or expression thereof, is detected at the nucleic acid level (e.g., in DNA or RNA, by PCR or qPCR). In some embodiments, a neoepitope, or expression thereof, is detected at the protein level (e.g., in a sample comprising polypeptides from cancer cells, which sample may be or comprise polypeptide complexes or other higher order structures including but not limited to cells, tissues, or organs).

In some particular embodiments, one or more neoepitopes are detected by whole exome sequencing. In some embodiments, one or more neoepitopes are detected by immunoassay. In some embodiments, one or more neoepitopes are detected by microarray. In some embodiments, one or more neoepitopes may be detected using massively parallel exome sequencing. In some embodiments, one or more neoepitopes may be detected by genome sequencing. In some embodiments, one or more neoepitopes may be detected by RNA sequencing. In some embodiments, one or more neoepitopes may be detected by standard DNA or RNA sequencing. In some embodiments, one or more neoepitopes may be detected by mass spectrometry. In some embodiments, one or more neoepitopes may be detected in circulating tumor DNA (ctDNA).

In some embodiments, one or more neoepitopes may be detected at the nucleic acid level using next generation sequencing (DNA and/or RNA). In some embodiments, neoepitopes, or expression thereof may be detected using genome resequencing, targeted sequencing panels, transcriptome profiling (RNA-Seq), DNA-protein interactions (ChIP-sequencing), and/or epigenome characterization. In some embodiments, re-sequencing of a patient's genome may be utilized, for example to detect genomic variations.

In some embodiments, one or more neoepitopes may be detected using a technique such as ELISA, Western Transfer, immunoassay, mass spectrometry, microarray analysis, etc.

Formulation

In some embodiments, the present disclosure provides compositions formulated for administration to a subject as described herein. In some embodiments, provided compositions include an active pharmaceutical ingredient and one or more pharmaceutically acceptable carriers or excipients. In some embodiments, provided compositions include an immunological adjuvant. A variety of adjuvant agents are known in the art. Appropriate adjuvants may be selected based on, for example, their ability to induce or enhance a particular type of immune response (e.g., a Th1 vs Th2 vs Th0 response, or a response particularly characterized by ADCC activity, by NK activity, by B cell activity, by CD8+ T cell activity, by Treg activity, etc).

In some embodiments, a pharmaceutically active ingredient may be or comprise a chemotherapeutic agent (e.g., a small molecule drug). In some embodiments, a pharmaceutically active ingredient may be or comprise a biologic agent (e.g., an antibody agent). In some embodiments, a pharmaceutically active ingredient may be or comprise an epitope (e.g., a serpin epitope, including for example a neoepitope, such as a neoepitope that may arise from and/or may comprise a serpin mutation, e.g., as described herein). In some embodiments, a pharmaceutically active ingredient may be or comprise a nucleic acid, for example that encodes an epitope. In some embodiments, a pharmaceutically active ingredient may be or comprise a cell (such as for example an immune cell [e.g., a T cell, a B cell, an NK cell] that targets (including that has been engineered to target) a cancer such as, for example, a cancer that expresses a serpin mutation e.g., as described herein.

Administration

Provided herein are methods of treating cancers, the course of which can be influenced by modulating immune checkpoints (e.g., negative immune response regulators) and/or administration of compositions comprising neoepitope(s). In some embodiments, the method comprises the step of administering to a subject suffering from or susceptible to a cancer an immune checkpoint modulation therapy agent and/or a compositions comprising neoepitope(s) e.g., in the form of a pharmaceutical composition, at a therapeutically effective amount. In some embodiments, the subject is determined to carry a serpin mutation. In some embodiments, the subject may not have developed symptoms of the cancer. Thus, in some embodiments, the present disclosure provides methods of prophylactic treatment.

In some embodiments, an active agent for use in accordance with the present disclosure is formulated, dosed, and/or administered in a therapeutically effective amount using pharmaceutical compositions and dosing regimens that are consistent with good medical practice and appropriate for the relevant agent(s) and subject(s). In principle, therapeutic compositions can be administered by any appropriate method known in the art, including, without limitation, oral, mucosal, by-inhalation, topical, buccal, nasal, rectal, or parenteral (e.g., intravenous, infusion, intratumoral, intranodal, subcutaneous, intraperitoneal, intramuscular, intradermal, transdermal, or other kinds of administration involving physical breaching of a tissue of a subject and administration of the therapeutic composition through the breach in the tissue).

In some embodiments, a dosing regimen for a particular active agent may involve intermittent or continuous (e.g., by perfusion or other slow release system) administration, for example to achieve a particular desired pharmacokinetic profile or other pattern of exposure in one or more tissues or fluids of interest in the subject receiving therapy.

In some embodiments, different agents administered in combination may be administered via different routes of delivery and/or according to different schedules. Alternatively or additionally, in some embodiments, one or more doses of a first active agent is administered substantially simultaneously with, and in some embodiments via a common route and/or as part of a single composition with, one or more other active agents.

Factors to be considered when optimizing routes and/or dosing schedule for a given therapeutic regimen may include, for example, the particular indication being treated, the clinical condition of a subject (e.g., age, overall health, prior therapy received and/or response thereto) the site of delivery of the agent, the nature of the agent (e.g., an antibody or other polypeptide-based compound), the mode and/or route of administration of the agent, the presence or absence of combination therapy, and other factors known to medical practitioners. For example, in the treatment of cancer, relevant features of the indication being treated may include, for example, one or more of cancer type, stage, location.

In some embodiments, one or more features of a particular pharmaceutical composition and/or of a utilized dosing regimen may be modified over time (e.g., increasing or decreasing the amount of active agent in any individual dose, increasing or decreasing time intervals between doses), for example in order to optimize a desired therapeutic effect or response (e.g., inhibition of a CTLA-4, increase of immune response to neoepitope).

In general, type, amount, and frequency of dosing of active agents in accordance with the present invention are governed by safety and efficacy requirements that apply when one or more relevant agent(s) is/are administered to a mammal, preferably a human. In general, such features of dosing are selected to provide a particular, and typically detectable, therapeutic response as compared to what is observed absent therapy.

In the context of the present invention, an exemplary desirable therapeutic response may involve, but is not limited to, inhibition of and/or decreased tumor growth, tumor size, metastasis, one or more of the symptoms and side effects that are associated with a tumor, as well as increased apoptosis of cancer cells, therapeutically relevant decrease or increase of one or more cell marker or circulating markers. Such criteria can be readily assessed by any of a variety of immunological, cytological, and other methods that are known to those skilled in the art.

In some embodiments, an effective dose (and/or a unit dose) of an active agent, may be at least about 0.01 µg/kg body weight, at least about 0.05 µg/kg body weight; at least about 0.1 µg/kg body weight, at least about 1 µg/kg body weight, at least about 2.5 µg/kg body weight, at least about 5 µg/kg body weight, and not more than about 100 µg/kg body weight. It will be understood by one of skill in the art that in some embodiments such guidelines may be adjusted for the molecular weight of the active agent. The dosage may also be varied for route of administration, the cycle of treatment, or consequently to dose escalation protocol that can be used to determine the maximum tolerated dose and dose limiting toxicity (if any) in connection to the administration of immune checkpoint modulation therapy. and/or an additional therapeutic agent at increasing doses. Consequently, the relative amounts of the each agent within a pharmaceutical composition may also vary, for example, each composition may comprise between 0.001% and 100% (w/w) of the corresponding agent.

In some embodiments, a "therapeutically effective amount" or "therapeutically effective dose" is an amount of an active agent, or a combination of two or more active agents, or a combination of an active agent with one or more additional therapeutic agent(s), which inhibits, totally or partially, the progression of the condition or alleviates, at least partially, one or more symptoms of the condition. In some embodiments, an amount which is therapeutically effective may depend upon a patient's size and/or gender, the condition to be treated, severity of the condition and/or the result sought. In some embodiments, a therapeutically effective amount refers to that amount of an immune checkpoint modulation therapy that results in amelioration of at least one symptom in a patient. In some embodiments, for a given patient, a therapeutically effective amount may be determined by methods known to those of skill in the art.

In some embodiments, immune checkpoint modulation therapy can be administered as a cycle. In some embodiments, a cycle is administration of immune checkpoint modulation therapy followed by a resting period. In some embodiments, a cycle is administration of immune checkpoint modulation therapy once during a first specified amount of time and repeated over a second period of time. In some embodiments, for example, immune checkpoint modulation therapy can be administered once daily, once, weekly, or once monthly for a period of days, months, or years. In some embodiments, for example, immune checkpoint modulation therapy can be administered once every three weeks for a year.

Combination Therapy

In some embodiments, an immune checkpoint modulation therapy can be used in combination with another therapeutic agent to treat diseases such as cancer. In some embodiments, an immune checkpoint modulation therapy, or a pharmaceutical composition comprising an immune checkpoint modulation therapy agent as described herein can optionally contain, and/or be administered in combination with, one or more additional therapeutic agents, such as a cancer therapeutic agent, e.g., a chemotherapeutic agent or a biological agent. An additional agent can be, for example, a therapeutic agent that is art-recognized as being useful to treat the disease or condition being treated by the immune checkpoint modulation therapy, e.g., an anti-cancer agent, or an agent that ameliorates a symptom associated with the disease or condition being treated. The additional agent also can be an agent that imparts a beneficial attribute to the therapeutic composition (e.g., an agent that affects the viscosity of the composition). For example, in some embodiments, immune checkpoint modulation therapy is administered to a subject who has received, is receiving, and/or will receive therapy with another therapeutic agent or modality (e.g., with a chemotherapeutic agent, surgery, radiation, or a combination thereof).

Some embodiments of combination therapy modalities provided by the present disclosure provide, for example, administration of an immune checkpoint modulation therapy and additional agent(s) in a single pharmaceutical formulation. Some embodiments provide administration of an immune checkpoint modulation therapy and administration of an additional therapeutic agent in separate pharmaceutical formulations.

Examples of chemotherapeutic agents that can be used in combination with an immune checkpoint modulation therapy agent described herein include platinum compounds (e.g., cisplatin, carboplatin, and oxaliplatin), alkylating agents (e.g., cyclophosphamide, ifosfamide, chlorambucil, nitrogen mustard, thiotepa, melphalan, busulfan, procarbazine, streptozocin, temozolomide, dacarbazine, and bendamustine), antitumor antibiotics (e.g., daunorubicin, doxorubicin, idarubicin, epirubicin, mitoxantrone, bleomycin, mytomycin C, plicamycin, and dactinomycin), taxanes (e.g., paclitaxel and docetaxel), antimetabolites (e.g., 5-fluorouracil, cytarabine, premetrexed, thioguanine, floxuridine, capecitabine, and methotrexate), nucleoside analogues (e.g., fludarabine, clofarabine, cladribine, pentostatin, and nelarabine), topoisomerase inhibitors (e.g., topotecan and irinotecan), hypomethylating agents (e.g., azacitidine and decitabine), proteosome inhibitors (e.g., bortezomib), epipodophyllotoxins (e.g., etoposide and teniposide), DNA synthesis inhibitors (e.g., hydroxyurea), vinca alkaloids (e.g., vicristine, vindesine, vinorelbine, and vinblastine), tyrosine kinase inhibitors (e.g., imatinib, dasatinib, nilotinib, sorafenib, and sunitinib), nitrosoureas (e.g., carmustine, fotemustine, and lomustine), hexamethylmelamine, mitotane, angiogenesis inhibitors (e.g., thalidomide and lenalidomide), steroids (e.g., prednisone, dexamethasone, and prednisolone), hormonal agents (e.g., tamoxifen, raloxifene, leuprolide, bicaluatmide, granisetron, and flutamide), aromatase inhibitors (e.g., letrozole and anastrozole), arsenic trioxide, tretinoin, nonselective cyclooxygenase inhibitors (e.g., nonsteroidal anti-inflammatory agents, salicylates, aspirin, piroxicam, ibuprofen, indomethacin, naprosyn, diclofenac, tolmetin, ketoprofen, nabumetone, and oxaprozin), selective cyclooxygenase-2 (COX-2) inhibitors, or any combination thereof.

Examples of biological agents that can be used in the compositions and methods described herein include monoclonal antibodies (e.g., rituximab, cetuximab, panetumumab, tositumomab, trastuzumab, alemtuzumab, gemtuzumab ozogamicin, bevacizumab, catumaxomab, denosumab, obinutuzumab, ofatumumab, ramucirumab, pertuzumab, nivolumab, nimotuzumab, lambrolizumab, siltuximab, BMS-936559, RG7446/MPDL3280A, MEDI4736, or others known in the art), enzymes (e.g., L-asparaginase), cytokines (e.g., interferons and interleukins), growth factors (e.g., colony stimulating factors and erythropoietin), cancer vaccines, gene therapy vectors, or any combination thereof.

In some embodiments, an immune checkpoint modulation therapy is administered to a subject in need thereof in combination with another agent for the treatment of cancer, either in the same or in different pharmaceutical compositions. In some embodiments, the additional agent is an anticancer agent. In some embodiments, the additional agent affects (e.g., inhibits) histone modifications, such as histone acetylation or histone methylation. In certain embodiments, an additional anticancer agent is selected from the group consisting of chemotherapeutics (such as 2CdA, 5-FU, 6-Mercaptopurine, 6-TG, Abraxane™, Accutane®, Actinomycin-D, Adriamycin®, Alimta®, all-trans retinoic acid, amethopterin, Ara-C, Azacitadine, BCNU, Blenoxane®, Camptosar®, CeeNU®, Clofarabine, Clolar™, Cytoxan®, daunorubicin hydrochloride, DaunoXome®, Dacogen®, DIC, Ellence®, Eloxatin®, Emcyt®, etoposide phosphate, Fludara®, FUDR®, Gemzar®, Gleevec®, hexamethylmelamine, Hycamtin®, Hydrea®, Idamycin®, Ifex®, ixabepilone, Ixempra®, L-asparaginase, Leukeran®, liposomal Ara-C, L-PAM, Lysodren, Matulane®, mithracin, Mitomycin-C, Myleran®, Navelbine®, Neutrexin®, nilotinib, Nipent®, Nitrogen Mustard, Novantrone®, Oncaspar®, Panretin®, Paraplatin®, Platinol®, prolifeprospan 20 with carmustine implant, Sandostatin®, Targretin®, Tasigna®, Taxotere®, Temodar®, TESPA, Trisenox®, Valstar®, Velban®, Vidaza™, vincristine sulfate, VM 26, Xeloda® and Zanosar®); biologics (such as Alpha Interferon, Bacillus Calmette-Guerin, Bexxar®, Campath®, Ergamisol®, Erlotinib, Herceptin®, Interleukin-2, Iressa®, lenalidomide, Mylotarg®, Ontak®, Pegasys®, Revlimid®, Rituxan®, Tarceva™, Thalomid®, Velcade® and Zevalin™); small molecules (such as Tykerb®); corticosteroids (such as dexamethasone sodium phosphate, DeltaSone® and Delta-Cortef®); hormonal therapies (such as Arimidex®, Aromasin®, Casodex®, Cytadren®, Eligard®, Eulexin®, Evista®, Faslodex®, Femara®, Halotestin®, Megace®, Nilandron®, Nolvadex®, Plenaxis™ and Zoladex®); and radiopharmaceuticals (such as Iodotope®, Metastron®, Phosphocol® and Samarium SM-153).

The additional agents that can be used in combination with immune checkpoint modulation therapy as set forth above are for illustrative purposes and not intended to be limiting. The combinations embraced by this disclosure, include, without limitation, one or more immune checkpoint modulation therapy(s) as provided herein or otherwise known in the art, and at least one additional agent selected from the lists above or otherwise provided herein. Immune checkpoint modulation therapy(s) can also be used in combination with one or with more than one additional agent, e.g., with two, three, four, five, or six, or more, additional agents.

In some embodiments, therapy with a composition comprising a neoepitope can be used in combination with another therapeutic agent to treat diseases such as cancer. In some embodiments, therapy with a composition comprising a neoepitope, or a pharmaceutical composition comprising a neoepitope as described herein can optionally contain, and/or be administered in combination with, one or more additional therapeutic agents, such as a cancer therapeutic agent, e.g., a chemotherapeutic agent or a biological agent. An additional agent can be, for example, a therapeutic agent that is art-recognized as being useful to treat the disease or condition being treated by the composition comprising a neoepitope, e.g., an anti-cancer agent, or an agent that ameliorates a symptom associated with the disease or condition being treated. The additional agent also can be an agent that imparts a beneficial attribute to the therapeutic composition (e.g., an agent that affects the viscosity of the composition). For example, in some embodiments, therapy with a composition comprising a neoepitope is administered to a subject who has received, is receiving, and/or will receive therapy with another therapeutic agent or modality (e.g., with a chemotherapeutic agent, surgery, radiation, or a combination thereof). In some embodiments, therapy with a composition comprising a neoepitope can be used in combination immune checkpoint modulation therapy.

In some embodiments, treatment methods described herein are performed on subjects for which other treatments of the medical condition have failed or have had less success in treatment through other means, e.g., in subjects having a cancer refractory to standard-of-care treatment. Additionally, the treatment methods described herein can be performed in conjunction with one or more additional treatments of the medical condition, e.g., in addition to or in combination with standard-of-care treatment. For instance, the method can comprise administering a cancer regimen, e.g., nonmyeloablative chemotherapy, surgery, hormone therapy, and/or radiation, prior to, substantially simultaneously with, or after the administration of agents described herein, or composition thereof. In certain embodiments, a subject to which a therapy described herein is administered can also be treated with antibiotics and/or one or more additional pharmaceutical agents.

EXEMPLIFICATION

Example 1: Exome Analysis of Samples from Two Melanoma Patient Cohorts Treated with Ipilimumab Immune checkpoint inhibitors have shown exceptional promise in the treatment of several advanced malignancies. For example, treatment with ipilimumab, an anti-CTLA4 antibody, has increased survival rates for patients with melanoma.[1,2] Anti-PD1 blockade has shown therapeutic efficacy in cancers such as melanoma, non-small cell lung cancer, and renal cell cancer, amongst others.[3-5] Understanding the genetic determinants of response to immune checkpoint blockade is critical for determining which patients will benefit from immunotherapy and for design more effective treatment options.

We and others have previously shown that the genetic features of cancers can shape the susceptibility of tumors to immune checkpoint blockade therapy.[6-9] For example, neoantigen load, mutational load, and tumor clonality can affect the likelihood of response to anti-CTLA4 or anti-PD1.[6-19] Prior sequencing studies have suggested that lung cancer patients with elevated smoking-related mutagenesis were more likely to respond to anti-PD1 therapy.[7] However, it is unknown whether the presence of mutations in specific genes can influence response rates for immune checkpoint inhibitors in a manner analogous to how EGFR mutations predict response to erlotinib.

To address this issue in a rigorous manner, we analyzed the exomes of matched tumor and normal pairs from 174 melanoma patients treated with anti-CTLA4 therapy. These patients were from two independent cohorts; one from the United States generated by us (n=64, cohort 1) and a second from Germany (n=110 cohort 2).[6,9] These data, along with a recently published analysis of mutations in melanoma by the TCGA now enable a gene-centric approach to detect recurrently mutated genes that predict survival.[11]

A comprehensive analysis of recurrent mutations in these datasets was performed to determine association with overall survival after anti-CTLA4 therapy (see methods described in Example 2; Table 2).[11] Strikingly, we discovered that SERPINB3 was recurrently mutated in patients deriving clinical benefit from anti-CTLA4. These mutations were strongly associated with overall survival following therapy in both independently collected cohorts (FIG. 1a). We also found mutations in SERPINB4, a close human homologue of SERPINB3 with which it shares 92% protein sequence identity. Not surprisingly, SERPINB3 and SERPINB4 have overlapping functions and are involved in both oncogenesis and immunity.[14-16] We have therefore considered mutations in both genes together.

TABLE 2

Recurrently Mutated Genes in Melanoma as Identified by InVex.

| Gene |
|---|
| BRAF |
| NRAS |
| CDKN2A |
| TP53 |
| ARID2 |
| IDH1 |
| PPP6C |
| PTEN |
| DDX3X |
| RAC1 |
| MAP2K1 |
| NF1 |
| CASP8 |
| CTNNB1 |
| PCDHGA1 |
| SERPINB3 |
| IRF7 |
| HRAS |
| PTPN11 |

Figure 1B:
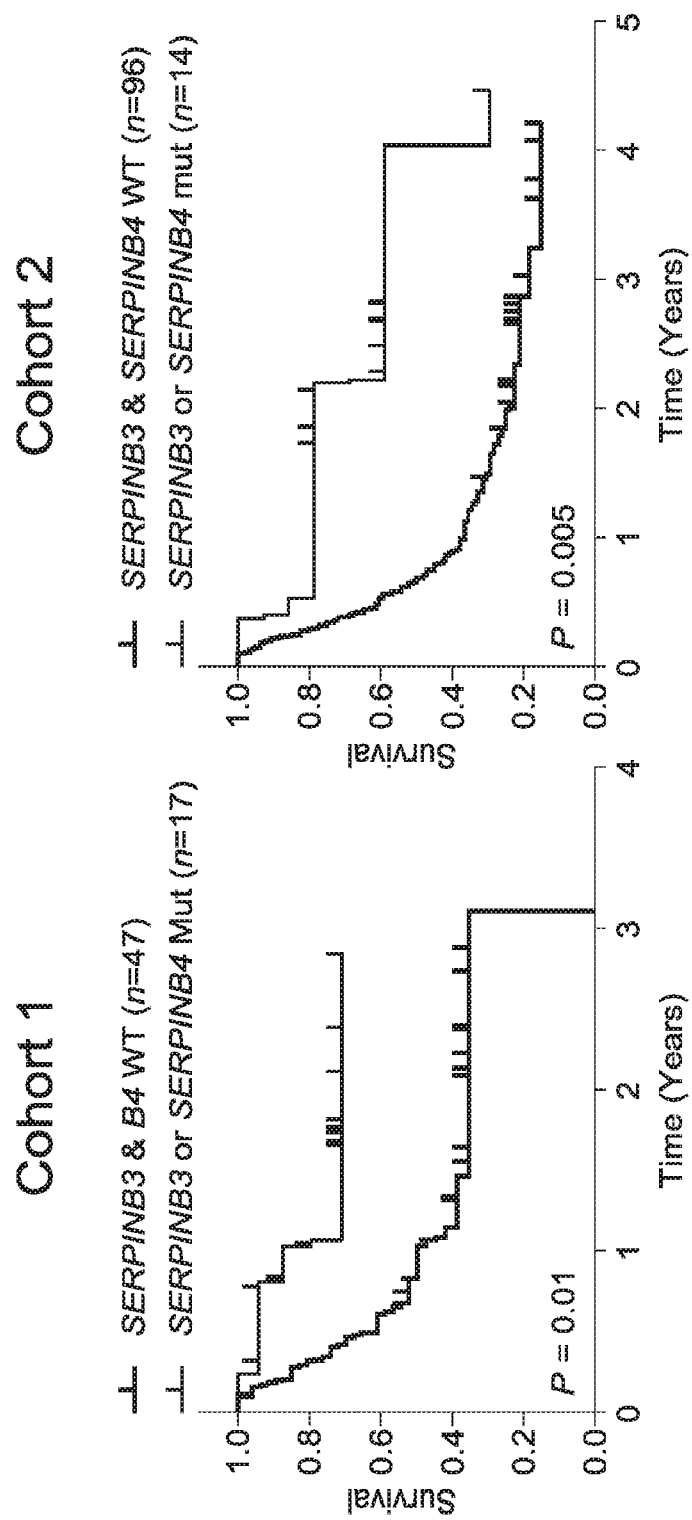
Figure 1C:
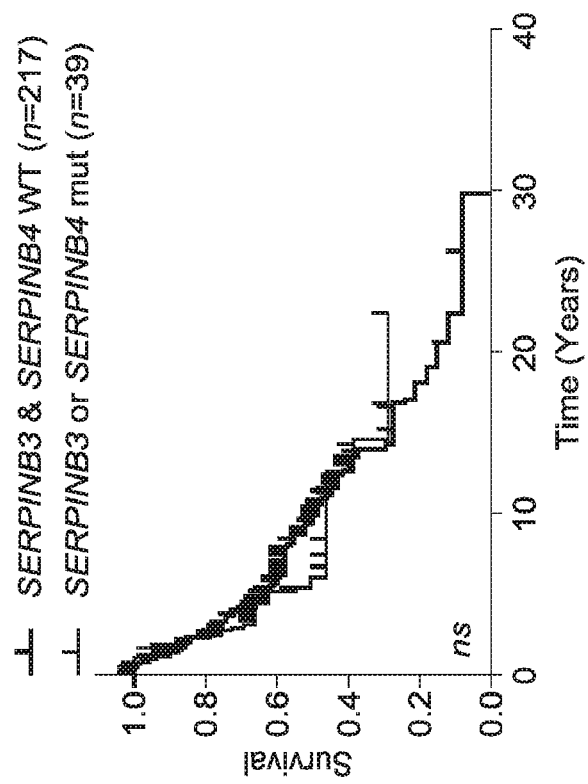
Figure 1D:
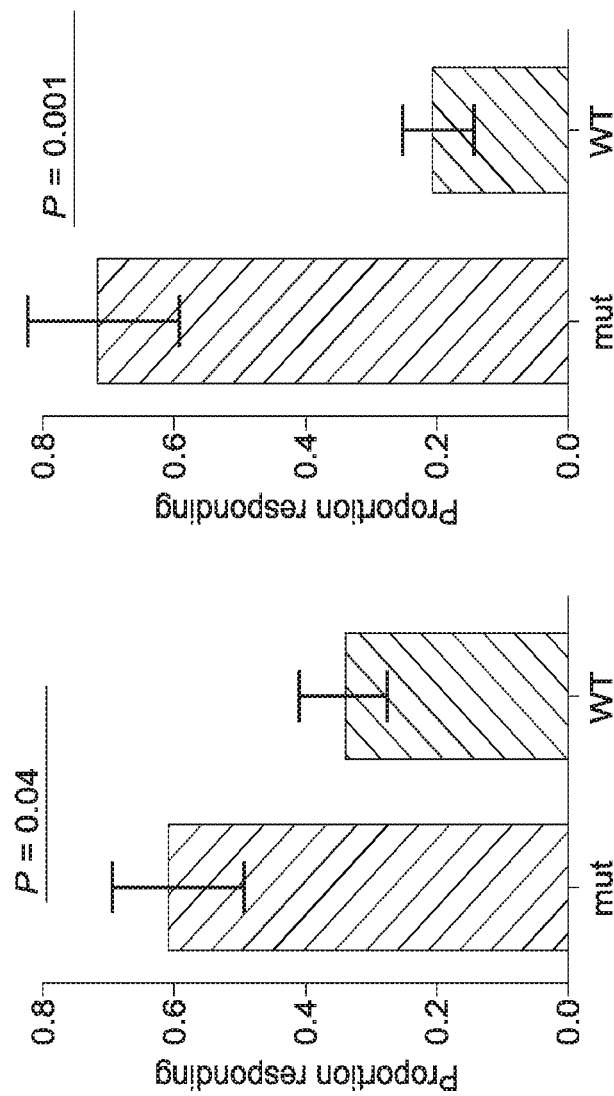
Figure 1E:
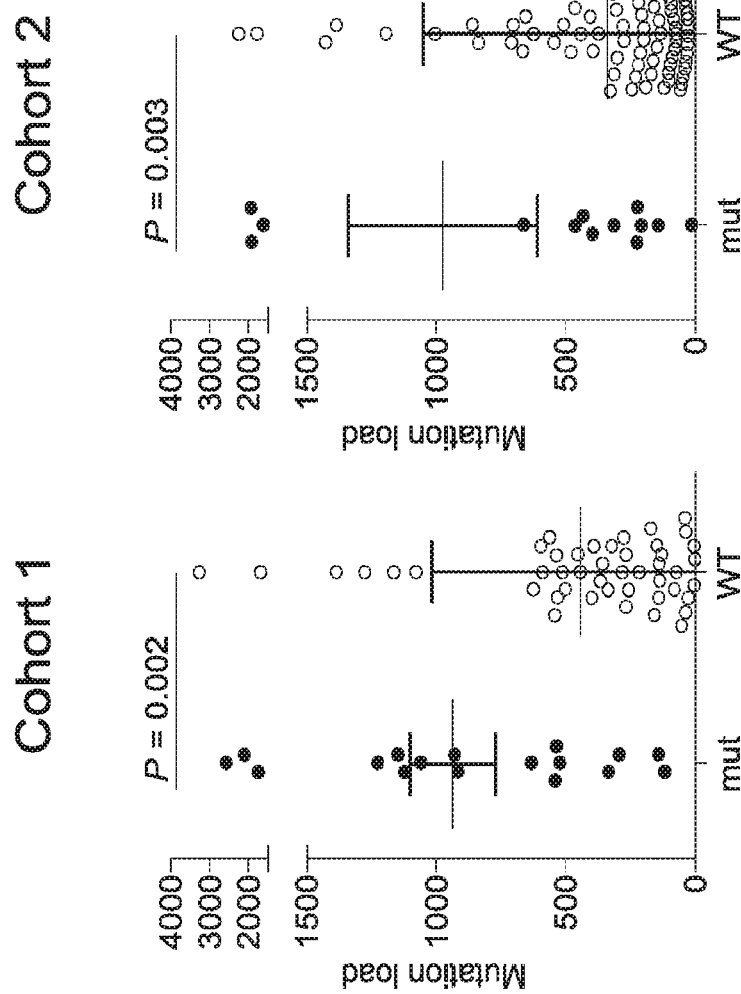
Figure 2A:
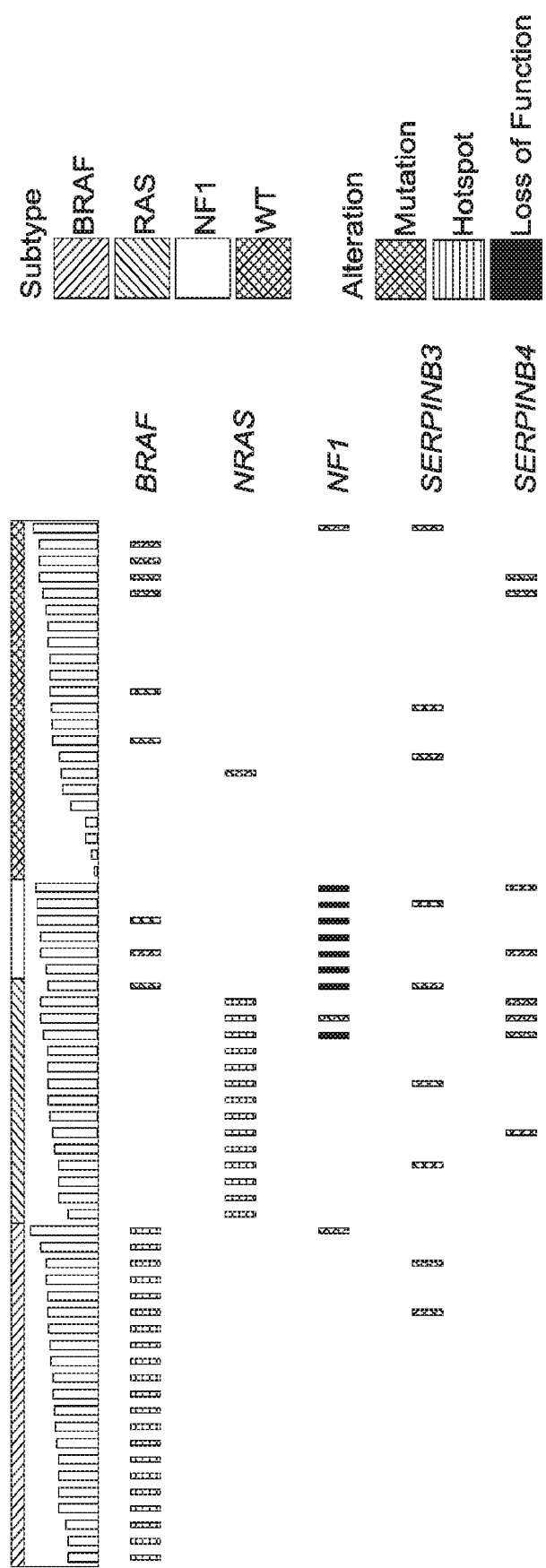
FIGS. 2a-2d show characteristics of mutations in SERPINB3 and SERPINB4.
Figure 2A:
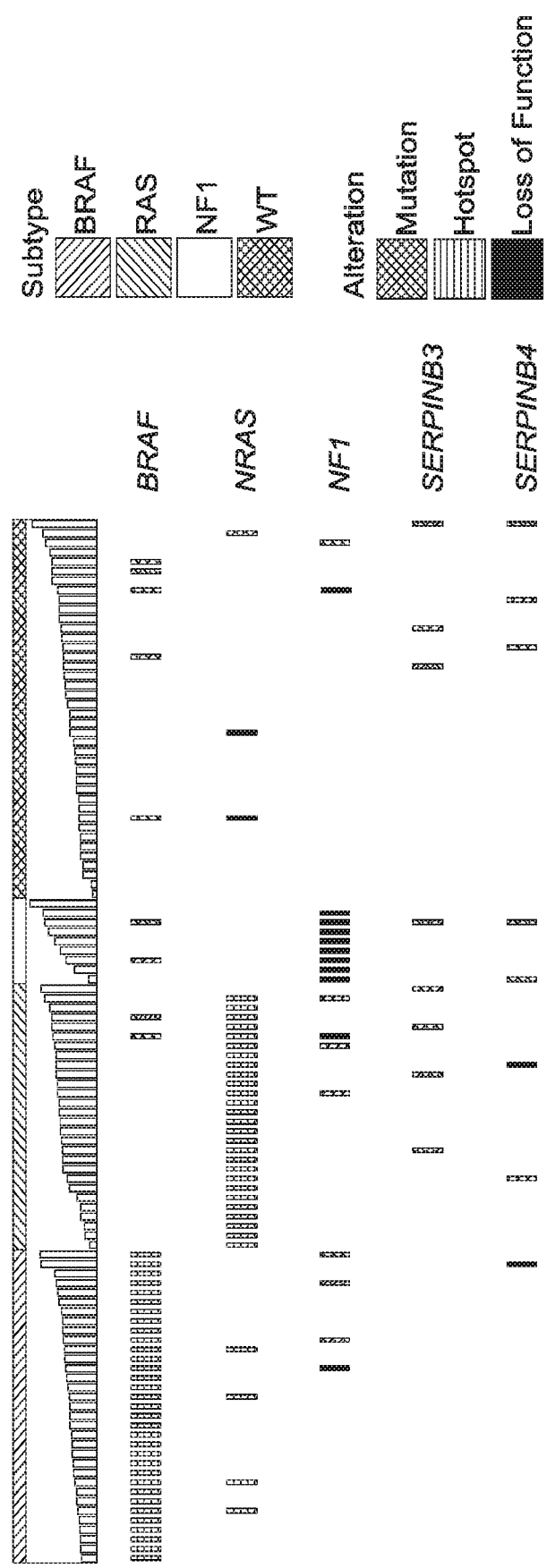

Mutations in either SERPINB3 or SERPINB4 (SERPINB3/B4) were associated with significantly longer survival following anti-CTLA4 treatment in both cohorts (FIG. 1b). Importantly, mutations in SERPINB3/B4 did not associate with survival in metastatic melanoma patients from the Cancer Genome Atlas Project (TCGA), suggesting that these mutations are predictive of response to immunotherapy and not simply prognostic (FIG. 1c). Patients with SERPINB3/B4 mutations were also significantly more likely to experience clinical benefit from anti-CTLA4 in both cohorts (FIG. 1d). Tumors with SERPINB3/B4 mutations were by no means limited to highly mutated tumors (FIG. 1e), and multivariate analysis revealed that SERPINB3/B4 mutations were associated with overall survival independent of mutation load (cohort 1: p=0.05; cohort 2: p=0.01; see methods described in Example 2; Table 3). Mutations occurred in all 4 subtypes of melanoma and appeared to be mutually exclusive of each other (FIG. 2a).

Figure 7:
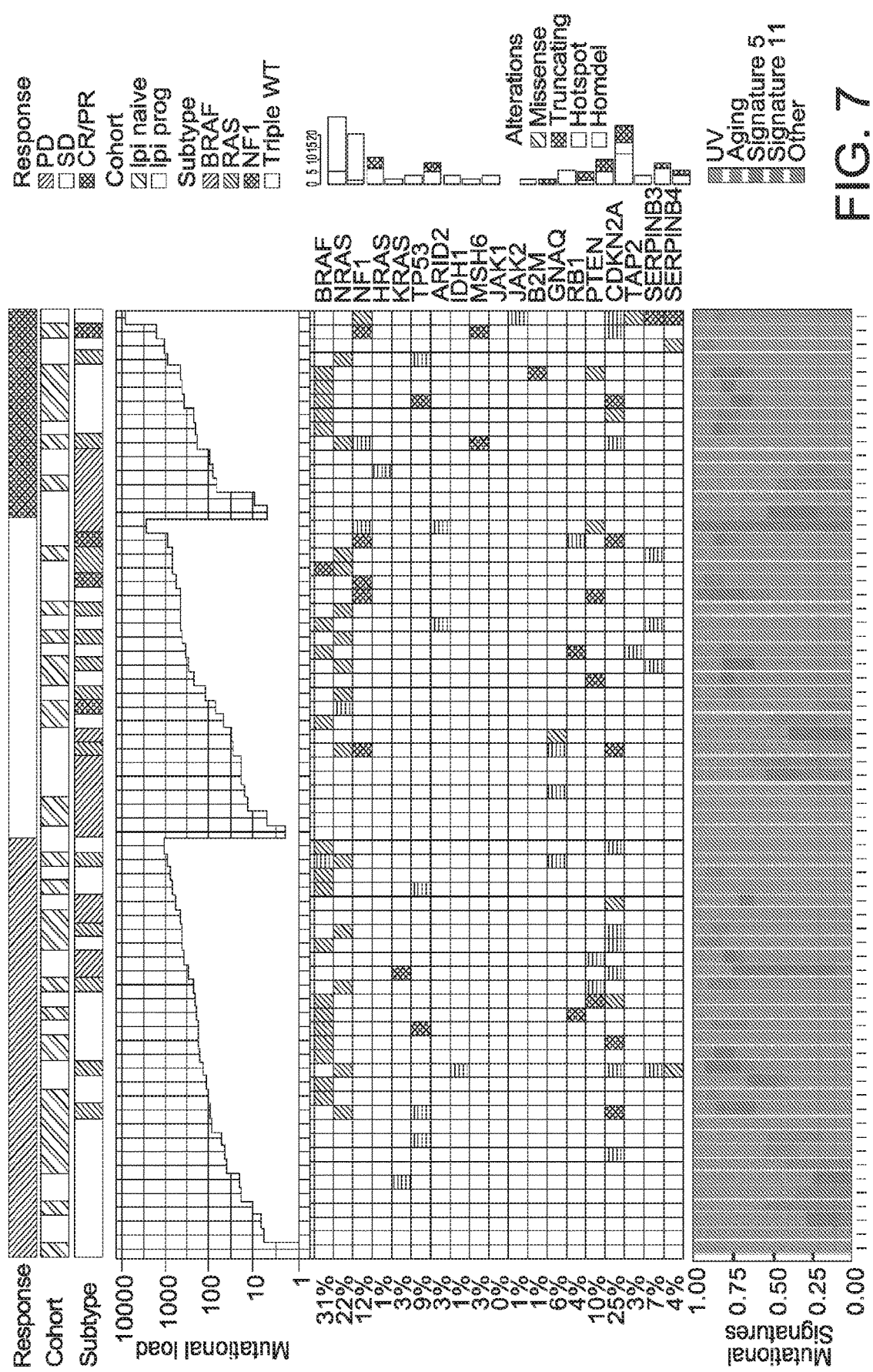
FIG. 7 further demonstrates clinical benefit or response of patients with SERPINB3 and SERPINB4 mutations. Baseline genomic characteristics of melanoma tumors from patients treated with immune checkpoint therapy is shown. An OncoPrint image of WES data for the cohort sorted by response group (Complete Response (CR)/Partial Response (PR), Stable Disease (SD), Progressive Disease (PD)) and treatment status (e.g. Ipi naïve—patients who had not received ipilimumab previously; ipi prog-patients who progressed on ipilimumab previously). The OncoPrint displays genes recurrently mutated in melanoma and genes that have been recently associated with response to therapy.

Additional studies further support the clinical benefit of immune checkpoint inhibitor treatment of patients with SERPINB3/4 mutations. FIG. 7 shows data from CA209-038 (NCT01621490; 2012-001840-23) in which 5 of 6 patients harboring SERPINB3/4 mutations show same response to treatment with immune checkpoint inhibitor treatment. The center panel of FIG. 7 is an Oncoprint which displays mutations that occur in patients in the cohort. Each row represents an individual gene and each colored box represents a mutation in the respective gene in an individual patient. The top panel displays the mutation load of each case. The bottom panel demonstrates what process created the mutations in each case. Five of six patients found to have SERPINB3/B4 mutations had disease control (CR/PR or stable disease [SD]) however this was not yet statistically significant, likely due to small numbers (p=0.21; Fisher's exact test).

TABLE 3

Multivariate Models of Overall Survival and SERPINB3/B4 mutation

| | Cohort 1 | | | Cohort 2 | | |
|---|---|---|---|---|---|---|
| Variable | HR | 95% CI | p-value | HR | 95% CI | p-value |
| SERPIN B3/B4 mutation | 0.34 | 0.11--0.98 | 0.047 | 0.32 | 0.13--0.76 | 0.010 |
| Mutation Load > Median | 0.56 | 0.27-1.17 | 0.122 | 0.97 | 0.62--1.52 | 0.883 |
| Stage M1a | 1.17 | 0.11--12.93 | 0.900 | 4.95 | 1.17--20.96 | 0.030 |
| Stage M1b | 2.15 | 0.26--17.98 | 0.480 | 3.48 | 0.95--12.74 | 0.060 |
| Stage M1c | 2.62 | 0.35--19.57 | 0.347 | 5.41 | 1.69--17.31 | 0.004 |

Figure 2B:
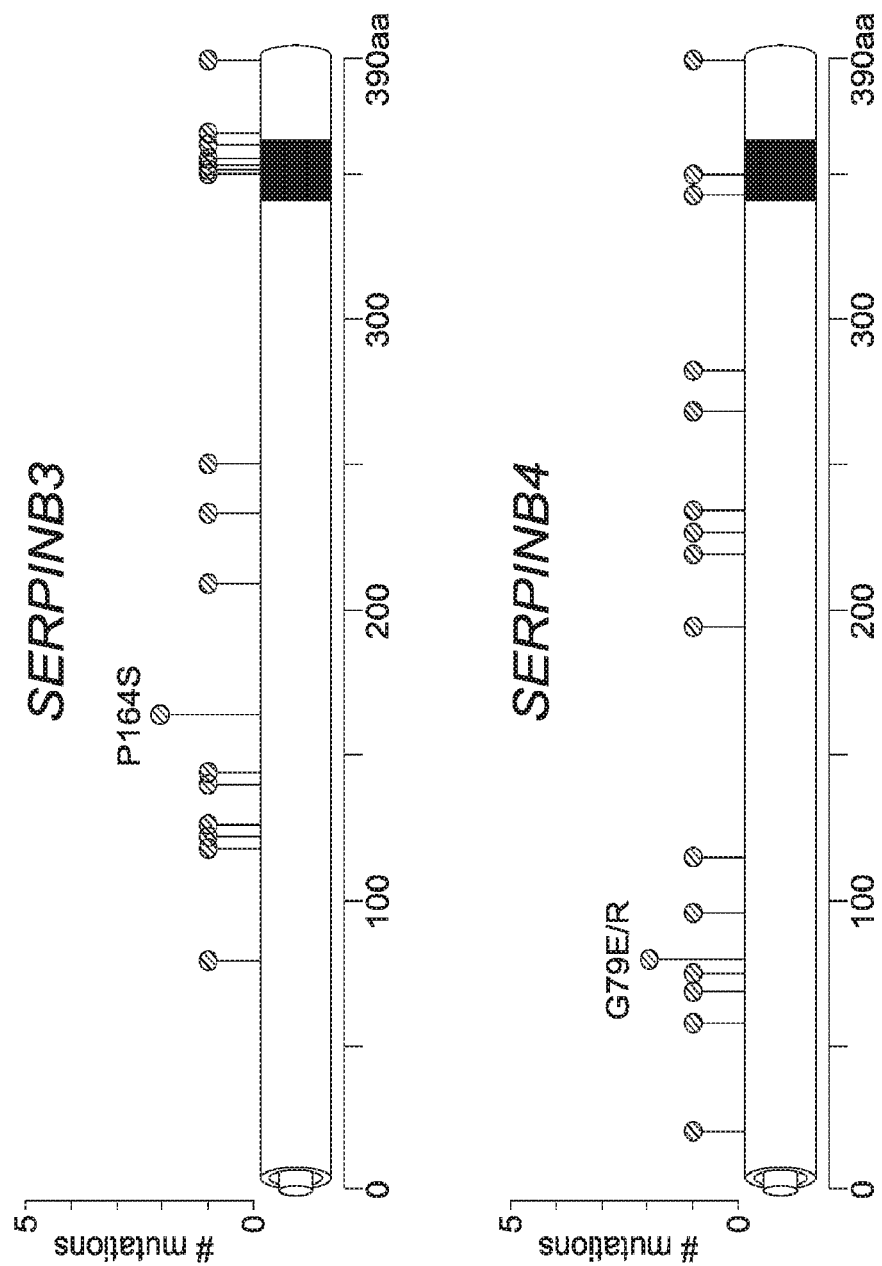
Figure 2D:
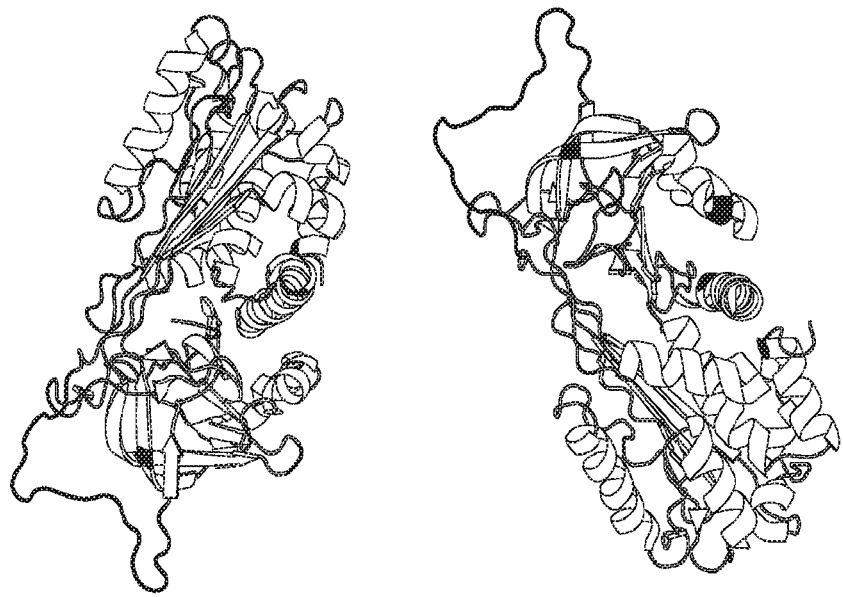
Figure 2C:
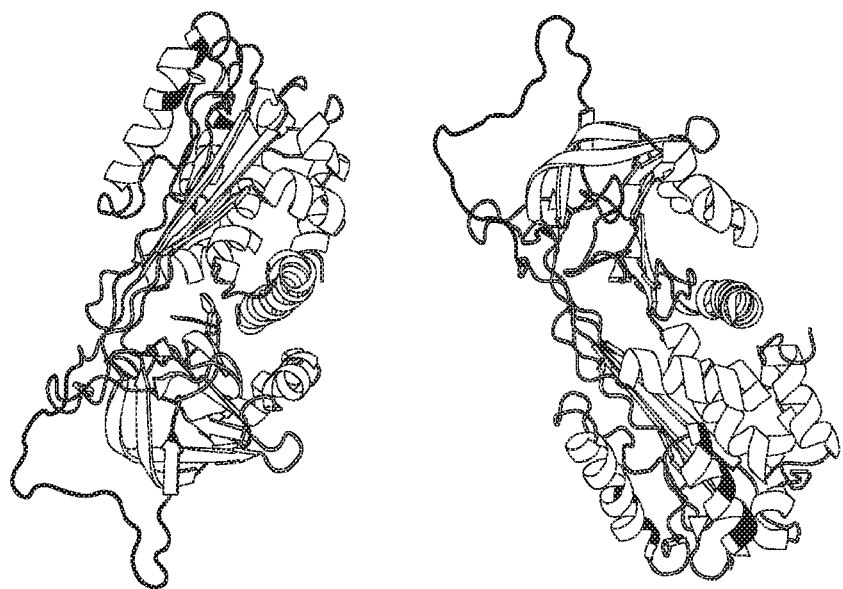
Figure 3A:
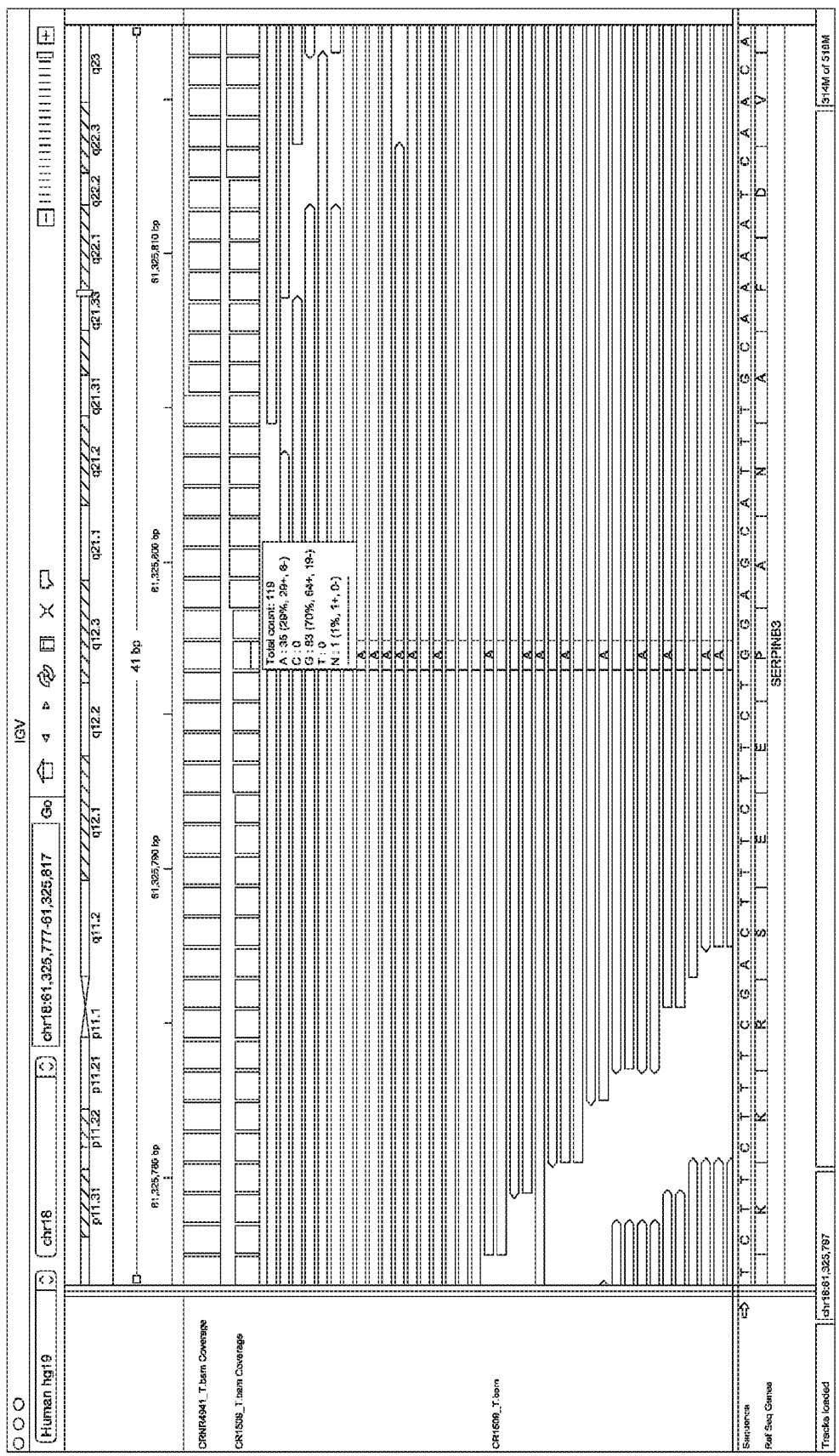
FIG. 3a-3c demonstrates further characteristics of mutations in SERPINB3 and SERPINB4 for individual patients. The left panels are sequences derived from tumors; the right panels are sequences derived from non-tumor tissue.
Figure 3A:
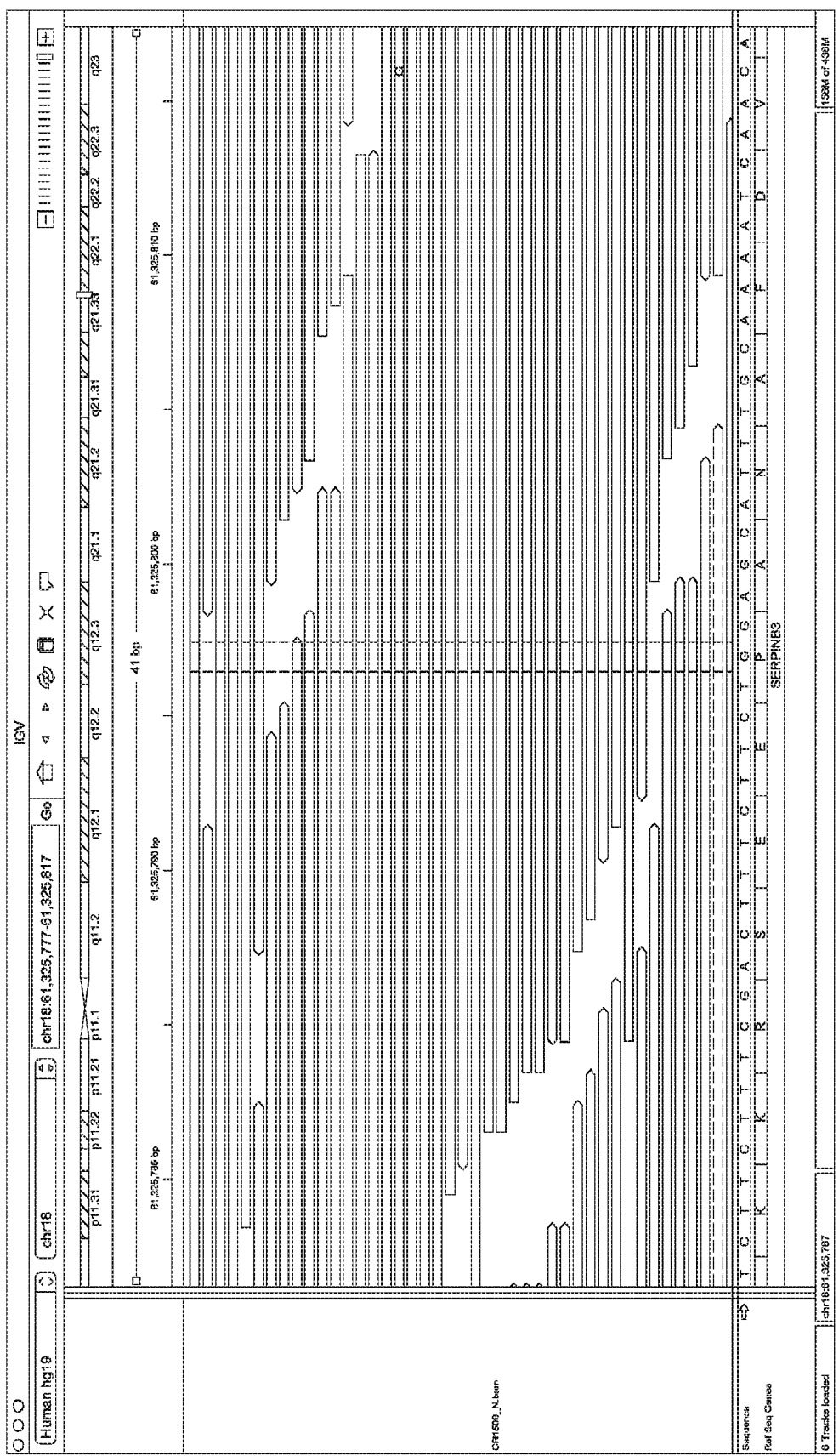
Figure 3B:
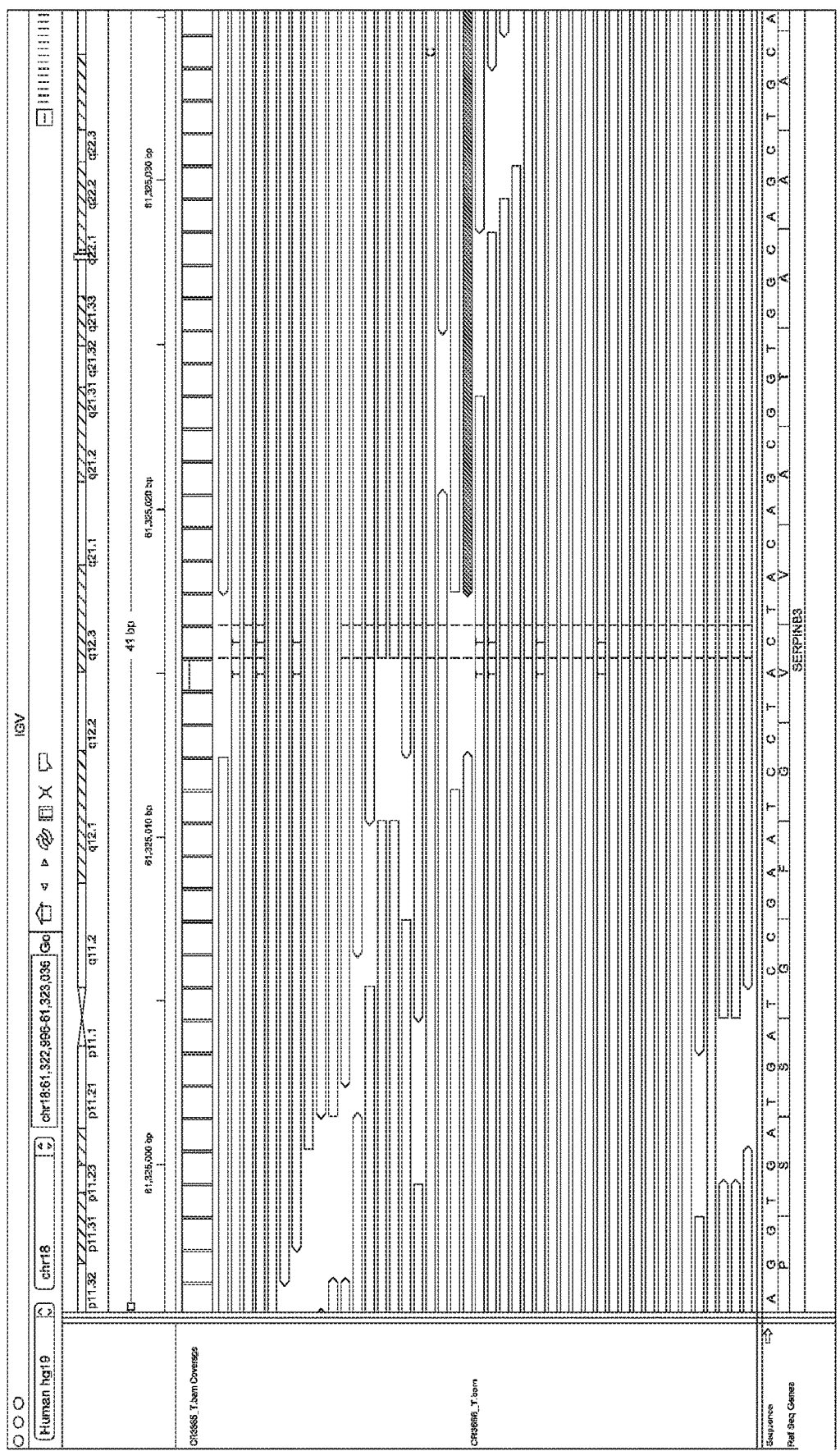
Figure 3B:
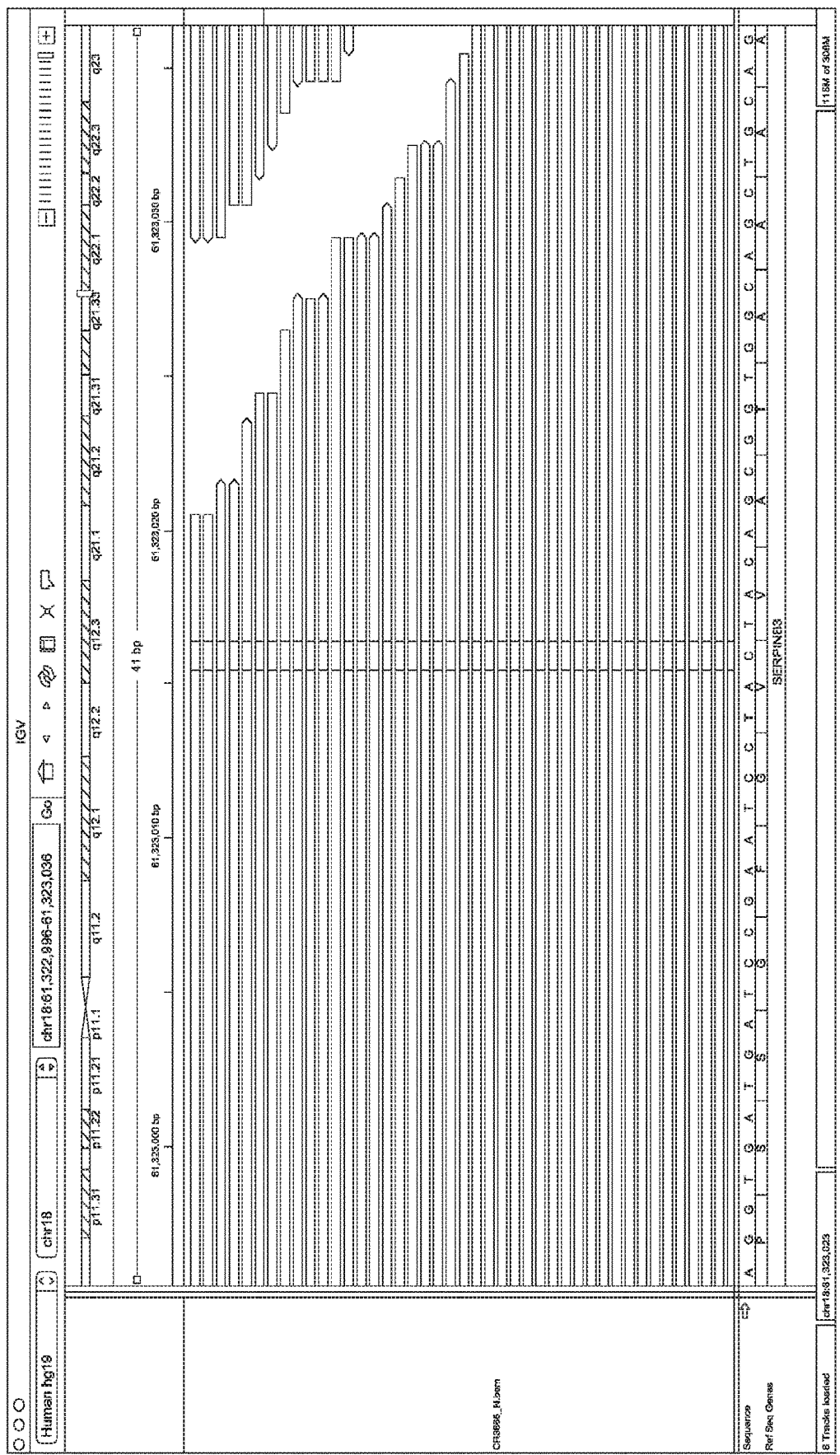
Figure 3C:
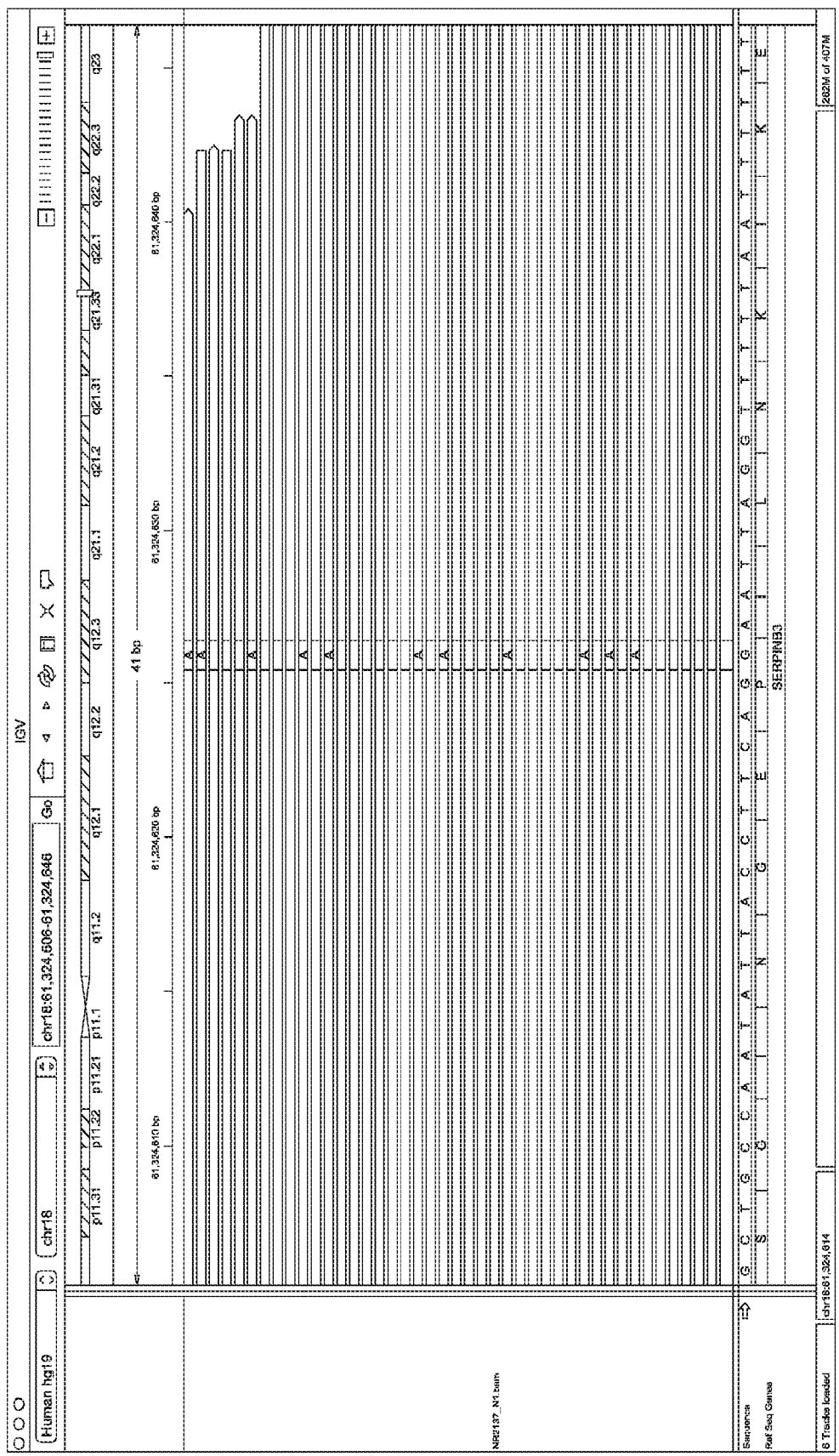
Figure 3C:
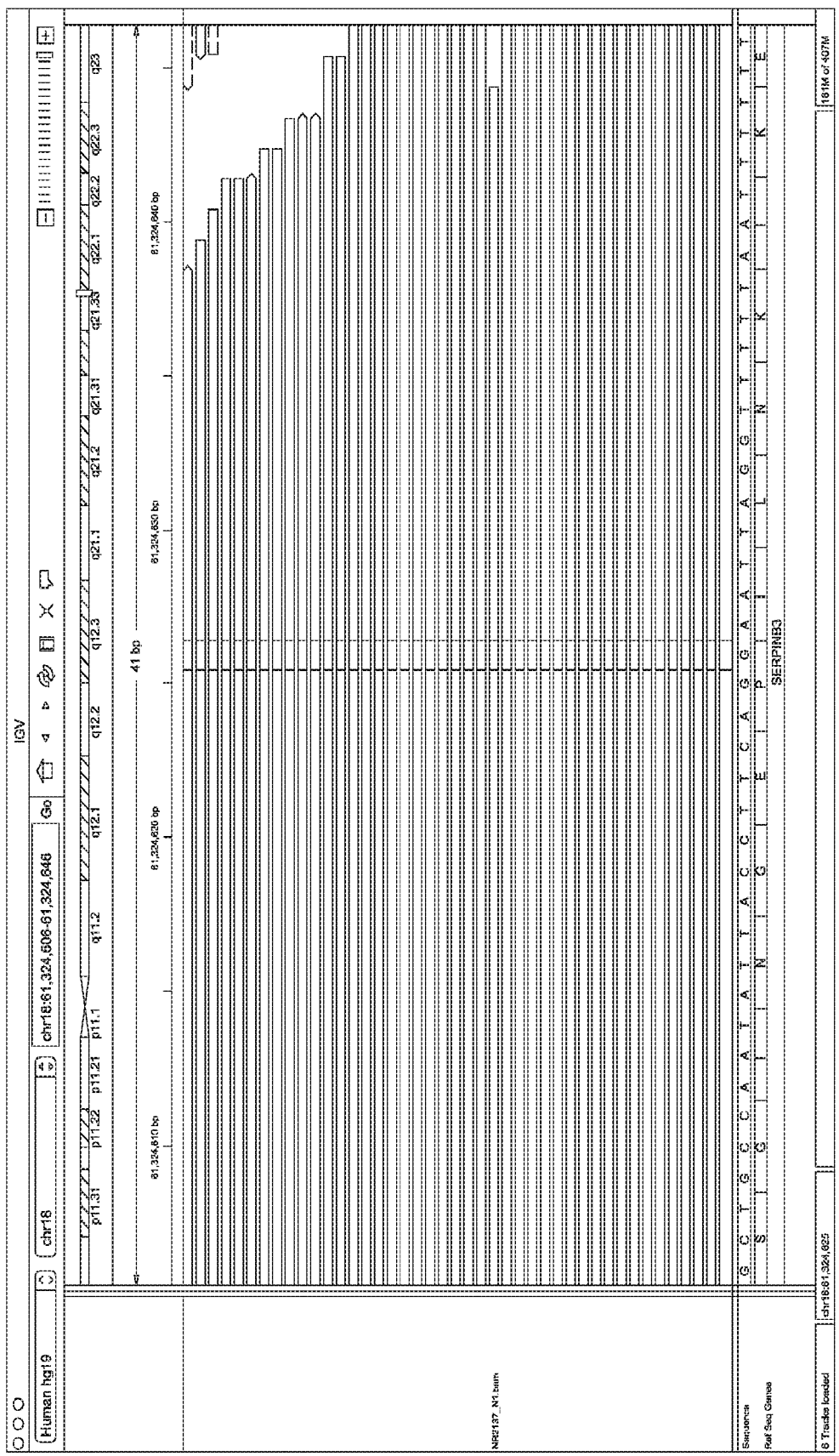
Figures 5A, 5B:
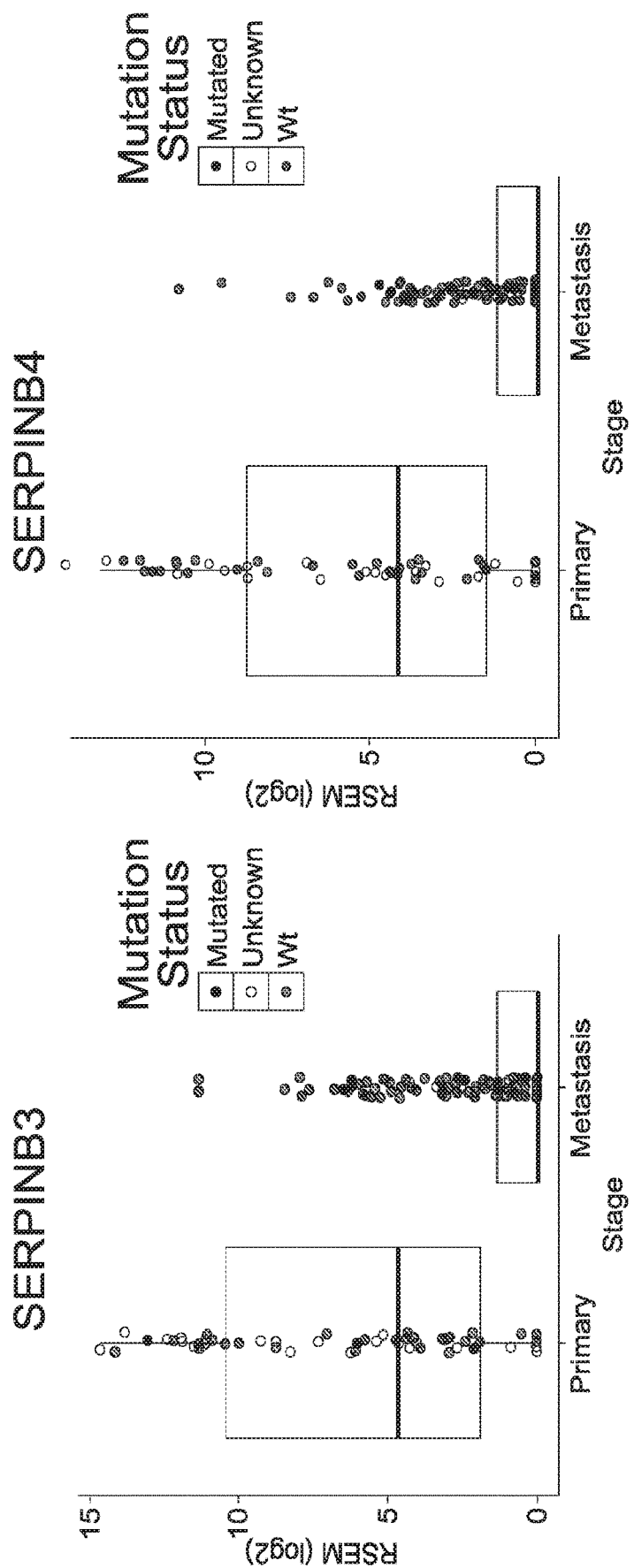
FIGS. 5a and 5b shows expression levels of mutated and non mutated SERPINB3 and SERPINB4, respectively, in primary and metastatic tumors.

The characteristics and locations of these mutations are described in FIG. 2b, FIGS. 5a and 5b, and Table 1. The missense mutations that occur throughout both genes may alter protein activity and in many cases are predicted to produce immunogenic neopeptides (Table 4 & 5). Indeed, visualization of mutations on the solved three-dimensional protein structure shows a cluster of mutations near the active site, the reactive center loop (RCL) domain (FIG. 2c,d).

Due to the pleiotropic functions of serpin proteins, a mechanistic link between mutations in genes encoding serpins and immunotherapy response is likely multifaceted and complex. The present disclosure, however, provides insight regarding which of the several aspects of serpin biology may be involved.

Interestingly, SERPINB3 is a human homologue of the chicken egg protein ovalbumin (OVA), a classic model antigen that contributes to egg allergies and atopic dermatitis in humans.[23] OVA and SERPINB3 share sequence similarity, including distinct regions functionally validated as epitopes of human OVA-reactive T cells.[24] The present disclosure notes that many of the observed SERPINB3/B4 mutations occur within these regions of homology (FIG. 4). However, these epitopes may or may not serve as direct targets for the adaptive immune system throughout the course of metastatic disease, and alternative mechanisms such as cross presentation and epitope spreading may be involved. Expression data from TCGA suggest SERPINB3/B4 are broadly expressed in primary tumors, but are significantly down-regulated in regional lymph nodes and metastatic sites, perhaps suggesting the occurrence of immuno-editing as tumors evolve or that silencing of these genes occur during metastasis (FIG. 5). As exemplified herein, SERPINB3/B4 mutations may exert an early immunogenic effect, thereby helping to initiate a broad immune response that can later be reinvigorated through checkpoint blockade.

Exome sequencing data for cohort 1 is available in dbGap at accession number phs001041.v1.p1, while cohort 2 is available with accession number phs000452.v2.p1

TABLE 4

Predicted class I neo-antigens in SERPINB3 and SERPINB4

| Dataset | Gene | Sample | Amino Acid Change | Mutated Peptide* | SEQ. ID. NO. | MHC Allele | Mutated IC50 | Wildtype IC50 |
|---|---|---|---|---|---|---|---|---|
| Cohort 1 | SERPINB3 | CRNR4941 | A122V | flqeyldVi | 1 | A0206 | 11 | 5 |

TABLE 4-continued

Predicted class I neo-antigens in SERPINB3 and SERPINB4

| Dataset | Gene | Sample | Amino Acid Change | Mutated Peptide* | SEQ. ID. NO. | MHC Allele | Mutated IC50 | Wildtype IC50 |
|---|---|---|---|---|---|---|---|---|
| Cohort 1 | SERPINB3 | CRNR4941 | A122V | yldVikkfy | 2 | C0501 | 45 | 17 |
| Cohort 1 | SERPINB3 | CR1509 | P140L | fanaLeesr | 3 | A3301 | 361 | 299 |
| Cohort 1 | SERPINB3 | PR4077 | H364Y | ptstneefY | 4 | A0101 | 19 | 13113 |
| Cohort 1 | SERPINB3 | PR4077 | H364Y | fYcnhpflf | 5 | C0602 | 113 | 14 |
| Cohort 1 | SERPINB3 | PR4077 | H364Y | fYcnhpflf | 6 | C0701 | 311 | 13 |
| Cohort 1 | SERPINB3 | PR4035 | G79E | yhvdrsEnv | 7 | C0602 | 29 | 81 |
| Cohort 1 | SERPINB3 | PR4035 | G79E | yhvdrsEnv | 8 | C1203 | 43 | 68 |
| Cohort 1 | SERPINB4 | CR6161 | M267I | kllewtslq | 9 | A0201 | 403 | 79 |
| Cohort 1 | SERPINB4 | CR6161 | M267I | lewtslqnm | 10 | B1801 | 362 | 74 |
| Cohort 1 | SERPINB4 | CR6161 | M267I | ltaekllew | 11 | B5701 | 24 | 19 |
| Cohort 1 | SERPINB4 | CR6161 | S218F | rqynFfnfa | 12 | A0201 | 216 | 831 |
| Cohort 1 | SERPINB4 | CR6161 | S218F | rqynFfnfa | 13 | C1203 | 348 | 963 |
| Cohort 1 | SERPINB4 | CR6161 | S218F | ynFfnfall | 14 | C1203 | 64 | 612 |
| Cohort 1 | SERPINB4 | S07357 | S95F | Ftdayelki | 15 | A0201 | 374 | 3822 |
| Cohort 1 | SERPINB4 | S07357 | S95F | Ftdayelki | 16 | C1203 | 113 | 4756 |
| Cohort 1 | SERPINB4 | NR9449 | D226N | lleNvqakv | 17 | A0201 | 249 | 77 |
| Cohort 1 | SERPINB4 | NR9449 | D226N | alleNvqak | 18 | A0301 | 89 | 218 |
| Cohort 2 | SERPINB3 | Pat124 | S389I | ilfygrfsTp | 19 | A0201 | 251 | 2277 |
| Cohort 2 | SERPINB3 | Pat79 | E118K | Kyldaikkf | 20 | A2301 | 23 | 60 |
| Cohort 2 | SERPINB3 | Pat79 | E118K | flqKyldai | 21 | A0201 | 12 | 5 |
| Cohort 2 | SERPINB3 | Pat79 | E118K | tylflqKyl | 22 | A2301 | 107 | 61 |
| Cohort 2 | SERPINB3 | Pat88 | E250K | smivllpnK | 23 | A0301 | 72 | 22038 |
| Cohort 2 | SERPINB4 | Pat117 | E68K | qvtenttKk | 24 | A1101 | 383 | 465 |

TABLE 4-continued

Predicted class I neo-antigens in SERPINB3 and SERPINB4

| Dataset | Gene | Sample | Amino Acid Change | Mutated Peptide* | SEQ. ID. NO. | MHC Allele | Mutated IC50 | Wildtype IC50 |
|---|---|---|---|---|---|---|---|---|
| Cohort 2 | SERPINB4 | Pat138 | V341M | Meaaaatav | 25 | B4402 | 134 | 930 |
| Cohort 2 | SERPINB4 | Pat71 | G79R | yhvdrsRnv | 26 | C1203 | 43 | 68 |

*Capital letter indicates position of mutated amino acid in 9-mer

TABLE 5

Predicted class II neoantigens in SERPINB3 and SERPINB4

| Dataset | Gene | Sample | Amino Acid Change | Mutated Peptide* | SEQ. ID. NO. | MHC Allele | Mutated IC50 | Wildtype IC50 |
|---|---|---|---|---|---|---|---|---|
| Cohort 1 | SERPINB3 | CRNR4941 | A122V | fgektylflqeyldV | 27 | HLA-DPA10103-DPB10201 | 0.3 | 0.5 |
| Cohort 1 | SERPINB3 | CRNR4941 | A122V | gektylflqeyldVi | 28 | HLA-DPA10103-DPB10201 | 0.12 | 0.17 |
| Cohort 1 | SERPINB3 | CRNR4941 | A122V | ektylflqeyldVik | 29 | HLA-DPA10103-DPB10201 | 0.09 | 0.15 |
| Cohort 1 | SERPINB3 | CRNR4941 | A122V | ktylflqeyldVikk | 30 | HLA-DPA10103-DPB10201 | 0.12 | 0.17 |
| Cohort 1 | SERPINB3 | CRNR4941 | A122V | tylflqeyldVikkf | 31 | HLA-DPA10103-DPB10201 | 0.17 | 0.3 |
| Cohort 1 | SERPINB3 | CRNR4941 | A122V | ylflqeyldVikkfy | 32 | HLA-DPA10103-DPB10201 | 0.6 | 0.8 |
| Cohort 1 | SERPINB3 | CRNR4941 | A122V | fgektylflqeyldV | 33 | HLA-DPA10103-DPB10202 | 0.25 | 0.5 |
| Cohort 1 | SERPINB3 | CRNR4941 | A122V | gektylflqeyldVi | 34 | HLA-DPA10103-DPB10202 | 0.08 | 0.15 |
| Cohort 1 | SERPINB3 | CRNR4941 | A122V | ektylflqeyldVik | 35 | HLA-DPA10103-DPB10202 | 0.07 | 0.12 |
| Cohort 1 | SERPINB3 | CRNR4941 | A122V | ktylflqeyldVikk | 36 | HLA-DPA10103-DPB10202 | 0.09 | 0.17 |
| Cohort 1 | SERPINB3 | CRNR4941 | A122V | tylflqeyldVikkf | 37 | HLA-DPA10103-DPB10202 | 0.12 | 0.25 |
| Cohort 1 | SERPINB3 | CRNR4941 | A122V | ylflqeyldVikkfy | 38 | HLA-DPA10103-DPB10202 | 0.4 | 0.7 |
| Cohort 1 | SERPINB3 | CRNR4941 | A122V | lfiqeyldVikkfyq | 39 | HLA-DPA10103-DPB10202 | 1.9 | 3.5 |
| Cohort 1 | SERPINB3 | CRNR4941 | A122V | fgektylflqeyldV | 40 | HLA-DQA10301-DQB10201 | 0.8 | 1.1 |
| Cohort 1 | SERPINB3 | CRNR4941 | A122V | gektylflqeyldVi | 41 | HLA-DQA10301-DQB10201 | 0.3 | 0.4 |
| Cohort 1 | SERPINB3 | CRNR4941 | A122V | ektylflqeyldVik | 42 | HLA-DQA10301-DQB10201 | 0.4 | 0.5 |
| Cohort 1 | SERPINB3 | CRNR4941 | A122V | ktylflqeyldVikk | 43 | HLA-DQA10301-DQB10201 | 0.6 | 0.8 |
| Cohort 1 | SERPINB3 | CRNR4941 | A122V | tylflqeyldVikkf | 44 | HLA-DQA10301-DQB10201 | 1.2 | 1.4 |
| Cohort 1 | SERPINB3 | CRNR4941 | A122V | fgektylflqeyldV | 45 | HLA-DQA10501-DQB10201 | 1.2 | 1.5 |

TABLE 5-continued

Predicted class II neoantigens in SERPINB3 and SERPINB4

| Dataset | Gene | Sample | Amino Acid Change | Mutated Peptide* | SEQ. ID. NO. | MHC Allele | Mutated IC50 | Wildtype IC50 |
|---|---|---|---|---|---|---|---|---|
| Cohort 1 | SERPINB3 | CRNR4941 | A122V | gektylflqeyldVi | 46 | HLA-DQA10501-DQB10201 | 0.6 | 0.7 |
| Cohort 1 | SERPINB3 | CRNR4941 | A122V | ektylflqeyldVik | 47 | HLA-DQA10501-DQB10201 | 0.6 | 0.7 |
| Cohort 1 | SERPINB3 | CRNR4941 | A122V | ktylflqeyldVikk | 48 | HLA-DQA10501-DQB10201 | 0.9 | 1 |
| Cohort 1 | SERPINB3 | CRNR4941 | A122V | tylflqeyldVikkf | 49 | HLA-DQA10501-DQB10201 | 1.6 | 1.7 |
| Cohort 1 | SERPINB3 | LSDNR1120 | G353R | egaeaaaatavvgfR | 50 | HLA-DQA10101-DQB10303 | 0.25 | 0.3 |
| Cohort 1 | SERPINB3 | LSDNR1120 | G353R | gaeaaaatavvgfRs | 51 | HLA-DQA10101-DQB10303 | 0.4 | 0.6 |
| Cohort 1 | SERPINB3 | LSDNR1120 | G353R | aeaaaatavvgfRss | 52 | HLA-DQA10101-DQB10303 | 0.7 | 1.1 |
| Cohort 1 | SERPINB3 | LSDNR1120 | G353R | eaaaatavvgfRssp | 53 | HLA-DQA10101-DQB10303 | 1.9 | 3.5 |
| Cohort 1 | SERPINB3 | CR22640 | S209F | kFigmmrqytsfhfa | 54 | DRB1_0701 | 1.9 | 3 |
| Cohort 1 | SERPINB3 | PR4077 | H364Y | neefYcnhpflffir | 55 | HLA-DPA10103-DPB10101 | 2 | 6.5 |
| Cohort 1 | SERPINB3 | PR4077 | H364Y | eefYcnhpflffirq | 56 | HLA-DPA10103-DPB10101 | 1.8 | 5.5 |
| Cohort 1 | SERPINB3 | PR4077 | H364Y | tneefYcnhpflffi | 57 | HLA-DPA10103-DPB10401 | 2 | 7.5 |
| Cohort 1 | SERPINB3 | PR4077 | H364Y | neefYcnhpflffir | 58 | HLA-DPA10103-DPB10401 | 1.3 | 4.5 |
| Cohort 1 | SERPINB3 | PR4077 | H364Y | eefYcnhpflffirq | 59 | HLA-DPA10103-DPB10401 | 1.2 | 4 |
| Cohort 1 | SERPINB3 | PR4077 | H364Y | efYcnhpflffirqn | 60 | HLA-DPA10103-DPB10401 | 1.5 | 4.5 |
| Cohort 1 | SERPINB3 | CR4880 | G351A | teegaeaaaatavvA | 61 | HLA-DQA10303-DQB10301 | 0.01 | 0.01 |
| Cohort 1 | SERPINB3 | CR4880 | G351A | eegaeaaaatavvAf | 62 | HLA-DQA10303-DQB10301 | 0.01 | 0.02 |
| Cohort 1 | SERPINB3 | CR4880 | G351A | egaeaaaatavvAfg | 63 | HLA-DQA10303-DQB10301 | 0.03 | 0.05 |
| Cohort 1 | SERPINB3 | CR4880 | G351A | gaeaaaatavvAfgs | 64 | HLA-DQA10303-DQB10301 | 0.06 | 0.17 |
| Cohort 1 | SERPINB3 | CR4880 | G351A | aeaaaatavvAfgss | 65 | HLA-DQA10303-DQB10301 | 0.17 | 0.6 |
| Cohort 1 | SERPINB3 | CR4880 | G351A | eaaaatavvAfgssp | 66 | HLA-DQA10303-DQB10301 | 0.6 | 1.8 |
| Cohort 1 | SERPINB3 | CR4880 | G351A | aaaatavvAfgsspt | 67 | HLA-DQA10303-DQB10301 | 1.2 | 4.5 |
| Cohort 1 | SERPINB3 | CR4880 | G351A | teegaeaaaatavvA | 68 | HLA-DQA10501-DQB10301 | 0.03 | 0.04 |
| Cohort 1 | SERPINB3 | CR4880 | G351A | eegaeaaaatavvAf | 69 | HLA-DQA10501-DQB10301 | 0.04 | 0.05 |

TABLE 5-continued

Predicted class II neoantigens in SERPINB3 and SERPINB4

| Dataset | Gene | Sample | Amino Acid Change | Mutated Peptide* | SEQ. ID. NO. | MHC Allele | Mutated IC50 | Wildtype IC50 |
|---|---|---|---|---|---|---|---|---|
| Cohort 1 | SERPINB3 | CR4880 | G351A | egaeaaaatavvAfg | 70 | HLA-DQA10501-DQB10301 | 0.06 | 0.1 |
| Cohort 1 | SERPINB3 | CR4880 | G351A | gaeaaaatavvAfgs | 71 | HLA-DQA10501-DQB10301 | 0.12 | 0.2 |
| Cohort 1 | SERPINB3 | CR4880 | G351A | aeaaaatavvAfgss | 72 | HLA-DQA10501-DQB10301 | 0.4 | 0.7 |
| Cohort 1 | SERPINB3 | CR4880 | G351A | eaaaatavvAfgssp | 73 | HLA-DQA10501-DQB10301 | 1 | 1.9 |
| Cohort 1 | SERPINB3 | CR4880 | G351A | aaaatavvAfgsspt | 74 | HLA-DQA10501-DQB10301 | 1.8 | 3.5 |
| Cohort 1 | SERPINB4 | CR6161 | S218F | vqmmrqynFfnfall | 75 | HLA-DPA10103-DPB10401 | 0.7 | 2.5 |
| Cohort 1 | SERPINB4 | CR6161 | S218F | qmmrqynFfnfalle | 76 | HLA-DPA10103-DPB10401 | 0.4 | 1.7 |
| Cohort 1 | SERPINB4 | CR6161 | S218F | mmrqynFfnfalled | 77 | HLA-DPA10103-DPB10401 | 0.25 | 1.5 |
| Cohort 1 | SERPINB4 | CR6161 | S218F | mrqynFfnfalledy | 78 | HLA-DPA10103-DPB10401 | 0.12 | 0.8 |
| Cohort 1 | SERPINB4 | CR6161 | S218F | rqynFfnfalledyq | 79 | HLA-DPA10103-DPB10401 | 0.12 | 0.9 |
| Cohort 1 | SERPINB4 | CR6161 | S218F | qynFfnfalledvqa | 80 | HLA-DPA10103-DPB10401 | 0.2 | 1.2 |
| Cohort 1 | SERPINB4 | CR6161 | S218F | ynFfnfalledvqak | 81 | HLA-DPA10103-DPB10401 | 0.4 | 1.9 |
| Cohort 1 | SERPINB4 | CR6161 | S218F | nFfnfalledvqakv | 82 | HLA-DPA10103-DPB10401 | 1 | 4.5 |
| Cohort 1 | SERPINB4 | CR6161 | S218F | qmmrqynFfnfalle | 83 | HLA-DPA10103-DPB110401 | 1 | 4.5 |
| Cohort 1 | SERPINB4 | CR6161 | S218F | mmrqynFfnfalled | 84 | HLA-DPA10103-DPB110401 | 0.7 | 4 |
| Cohort 1 | SERPINB4 | CR6161 | S218F | mrqynFfnfalledv | 85 | HLA-DPA10103-DPB110401 | 0.3 | 2.5 |
| Cohort 1 | SERPINB4 | CR6161 | S218F | rqynFfnfalledvq | 86 | HLA-DPA10103-DPB110401 | 0.3 | 2.5 |
| Cohort 1 | SERPINB4 | CR6161 | S218F | qynFfnfalledvqa | 87 | HLA-DPA10103-DPB110401 | 0.3 | 2.5 |
| Cohort 1 | SERPINB4 | CR6161 | S218F | ynFfnfalledvqak | 88 | HLA-DPA10103-DPB110401 | 0.5 | 2.5 |
| Cohort 1 | SERPINB4 | CR6161 | S218F | nFfnfalledvqakv | 89 | HLA-DPA10103-DPB110401 | 1.1 | 4 |
| Cohort 1 | SERPINB4 | NR9449 | D226N | qynsfnfalleNvqa | 90 | DRB1_0401 | 1.6 | 14 |
| Cohort 1 | SERPINB4 | NR9449 | D226N | ynsfnfalleNvqak | 91 | DRB1_0401 | 0.6 | 7 |
| Cohort 1 | SERPINB4 | NR9449 | D226N | nsfnfalleNvqakv | 92 | DRB1_0401 | 0.4 | 5 |
| Cohort 1 | SERPINB4 | NR9449 | D226N | sfnfalleNvqakyl | 93 | DRB1_0401 | 0.4 | 4.5 |
| Cohort 1 | SERPINB4 | NR9449 | D226N | fnfalleNvqakyle | 94 | DRB1_0401 | 0.5 | 5.5 |

TABLE 5-continued

Predicted class II neoantigens in SERPINB3 and SERPINB4

| Dataset | Gene | Sample | Amino Acid Change | Mutated Peptide* | SEQ. ID. NO. | MHC Allele | Mutated IC50 | Wildtype IC50 |
|---|---|---|---|---|---|---|---|---|
| Cohort 1 | SERPINB4 | NR9449 | D226N | nfalleNvqakylei | 95 | DRB1_0401 | 1.3 | 9.5 |
| Cohort 1 | SERPINB4 | NR9449 | D226N | mmrqynsfnfalleN | 96 | HLA-DPA10103-DPB10201 | 1.3 | 1.4 |
| Cohort 1 | SERPINB4 | NR9449 | D226N | mrqynsfnfalleNv | 97 | HLA-DPA10103-DPB10201 | 0.6 | 0.7 |
| Cohort 1 | SERPINB4 | NR9449 | D226N | rqynsfnfalleNvq | 98 | HLA-DPA10103-DPB10201 | 0.7 | 0.7 |
| Cohort 1 | SERPINB4 | NR9449 | D226N | qynsfnfalleNvqa | 99 | HLA-DPA10103-DPB10201 | 0.9 | 1 |
| Cohort 1 | SERPINB4 | NR9449 | D226N | ynsfnfalleNvqak | 100 | HLA-DPA10103-DPB10201 | 1.5 | 1.6 |
| Cohort 1 | SERPINB4 | NR9449 | D226N | mrqynsfnfalleNv | 101 | HLA-DPA10103-DPB10301 | 1.7 | 2.5 |
| Cohort 1 | SERPINB4 | NR9449 | D226N | rqynsfnfalleNvq | 102 | HLA-DPA10103-DPB10301 | 1.5 | 2.5 |
| Cohort 1 | SERPINB4 | NR9449 | D226N | qynsfnfalleNvqa | 103 | HLA-DPA10103-DPB10301 | 1.3 | 2.5 |
| Cohort 1 | SERPINB4 | NR9449 | D226N | ynsfnfalleNvqak | 104 | HLA-DPA10103-DPB10301 | 1.4 | 2.5 |
| Cohort 1 | SERPINB4 | NR9449 | D226N | nsfnfalleNvqakv | 105 | HLA-DPA10103-DPB10301 | 1.9 | 4 |
| Cohort 1 | SERPINB4 | CR04885 | E233K | fnfalledvqakvlK | 106 | HLA-DQA10201-DQB10202 | 1.2 | 1.1 |
| Cohort 1 | SERPINB4 | CR04885 | E233K | fnfalledvqakvlK | 107 | HLA-DQA10303-DQB10202 | 1.1 | 0.9 |
| Cohort 2 | SERPINB3 | Pat126 | F126C | tylflqeyldaikkC | 108 | HLA-DPA10103-DPB10401 | 0.5 | 0.4 |
| Cohort 2 | SERPINB3 | Pat126 | F126C | ylflqeyldaikkCy | 109 | HLA-DPA10103-DPB10401 | 1.2 | 0.9 |
| Cohort 2 | SERPINB3 | Pat126 | F126C | tylflqeyldaikkC | 110 | HLA-DQA10301-DQB10201 | 1.7 | 1.4 |
| Cohort 2 | SERPINB3 | Pat126 | F126C | tylflqeyldaikkC | 111 | HLA-DQA10501-DQB10201 | 2 | 1.7 |
| Cohort 2 | SERPINB3 | Pat138 | S355L | aeaaaatavvgfgsL | 112 | HLA-DQA10101-DQB10301 | 0.8 | 0.8 |
| Cohort 2 | SERPINB3 | Pat138 | S355L | aeaaaatavvgfgsL | 113 | HLA-DQA10505-DQB10301 | 0.7 | 0.7 |
| Cohort 2 | SERPINB3 | Pat138 | S355L | eaaaatavvgfgsLp | 114 | HLA-DQA10505-DQB10301 | 2 | 1.9 |
| Cohort 2 | SERPINB3 | Pat79 | E118K | anklfqektylflqK | 115 | HLA-DPA10103-DPB10401 | 1.6 | 1.9 |
| Cohort 2 | SERPINB3 | Pat79 | E118K | nklfqektylflqKy | 116 | HLA-DPA10103-DPB10401 | 1 | 1.4 |
| Cohort 2 | SERPINB3 | Pat79 | E118K | klfqektylflqKyl | 117 | HLA-DPA10103-DPB10401 | 0.7 | 0.9 |
| Cohort 2 | SERPINB3 | Pat79 | E118K | lfqektylflqKyld | 118 | HLA-DPA10103-DPB10401 | 0.9 | 0.7 |
| Cohort 2 | SERPINB3 | Pat79 | E118K | fqektylflqKylda | 119 | HLA-DPA10103-DPB10401 | 1 | 0.5 |

TABLE 5-continued

Predicted class II neoantigens in SERPINB3 and SERPINB4

| Dataset | Gene | Sample | Amino Acid Change | Mutated Peptide* | SEQ. ID. NO. | MHC Allele | Mutated IC50 | Wildtype IC50 |
|---|---|---|---|---|---|---|---|---|
| Cohort 2 | SERPINB3 | Pat79 | E118K | qektylflqKyldai | 120 | HLA-DPA10103-DPB10401 | 0.7 | 0.2 |
| Cohort 2 | SERPINB3 | Pat79 | E118K | ektylflqKyldaik | 121 | HLA-DPA10103-DPB10401 | 0.7 | 0.17 |
| Cohort 2 | SERPINB3 | Pat79 | E118K | ktylflqKyldaikk | 122 | HLA-DPA10103-DPB10401 | 1.1 | 0.25 |
| Cohort 2 | SERPINB3 | Pat79 | E118K | tylflqKyldaikkf | 123 | HLA-DPA10103-DPB10401 | 1.9 | 0.4 |
| Cohort 2 | SERPINB3 | Pat88 | E250K | lsmivllpnKidglq | 124 | DRB1_1501 | 1.9 | 16 |
| Cohort 2 | SERPINB4 | Path 1 | A348V | vteegveaaaatVvv | 125 | HLA-DQA10102-DQB10603 | 1.5 | 1.1 |
| Cohort 2 | SERPINB4 | Path 1 | A348V | teegveaaaatVvvv | 126 | HLA-DQA10102-DQB10603 | 1.3 | 0.7 |
| Cohort 2 | SERPINB4 | Path 1 | A348V | eegveaaaatVvvvv | 127 | HLA-DQA10102-DQB10603 | 1.7 | 0.7 |
| Cohort 2 | SERPINB4 | Path 1 | A348V | vteegveaaaatVvv | 128 | HLA-DQA10102-DQB10609 | 1.2 | 0.9 |
| Cohort 2 | SERPINB4 | Path 1 | A348V | teegveaaaatVvvv | 129 | HLA-DQA10102-DQB10609 | 0.8 | 0.5 |
| Cohort 2 | SERPINB4 | Path 1 | A348V | eegveaaaatVvvvv | 130 | HLA-DQA10102-DQB10609 | 1 | 0.5 |
| Cohort 2 | SERPINB4 | Path 1 | A348V | egveaaaatVvvvve | 131 | HLA-DQA10102-DQB10609 | 1.3 | 0.5 |
| Cohort 2 | SERPINB4 | Path 1 | A348V | gveaaaatVvvvvel | 132 | HLA-DQA10102-DQB10609 | 1.6 | 0.4 |
| Cohort 2 | SERPINB4 | Path 1 | A348V | vteegveaaaatVvv | 133 | HLA-DQA10103-DQB10603 | 2 | 1.4 |
| Cohort 2 | SERPINB4 | Path 1 | A348V | teegveaaaatVvvv | 134 | HLA-DQA10103-DQB10603 | 1.7 | 0.9 |
| Cohort 2 | SERPINB4 | Path 1 | A348V | vteegveaaaatVvv | 135 | HLA-DQA10103-DQB10609 | 1.6 | 1.2 |
| Cohort 2 | SERPINB4 | Path 1 | A348V | teegveaaaatVvvv | 136 | HLA-DQA10103-DQB10609 | 1.1 | 0.7 |
| Cohort 2 | SERPINB4 | Path 1 | A348V | eegveaaaatVvvvv | 137 | HLA-DQA10103-DQB10609 | 1.3 | 0.7 |
| Cohort 2 | SERPINB4 | Path 1 | A348V | egveaaaatVvvvve | 138 | HLA-DQA10103-DQB10609 | 1.4 | 0.6 |
| Cohort 2 | SERPINB4 | Path 1 | A348V | gveaaaatVvvvvel | 139 | HLA-DQA10103-DQB10609 | 1.7 | 0.5 |
| Cohort 2 | SERPINB4 | Pat138 | V341M | vevteegMeaaaata | 140 | HLA-DQA10101-DQB10301 | 0.5 | 0.5 |
| Cohort 2 | SERPINB4 | Pat138 | V341M | evteegMeaaaatav | 141 | HLA-DQA10101-DQB10301 | 0.07 | 0.07 |
| Cohort 2 | SERPINB4 | Pat138 | V341M | vteegMeaaaatavv | 142 | HLA-DQA10101-DQB10301 | 0.03 | 0.03 |
| Cohort 2 | SERPINB4 | Pat138 | V341M | teegMeaaaatavvv | 143 | HLA-DQA10101-DQB10301 | 0.01 | 0.01 |
| Cohort 2 | SERPINB4 | Pat138 | V341M | eegMeaaaatavvvv | 144 | HLA-DQA10101-DQB10301 | 0.02 | 0.01 |

TABLE 5-continued

Predicted class II neoantigens in SERPINB3 and SERPINB4

| Dataset | Gene | Sample | Amino Acid Change | Mutated Peptide* | SEQ. ID. NO. | MHC Allele | Mutated IC50 | Wildtype IC50 |
|---|---|---|---|---|---|---|---|---|
| Cohort 2 | SERPINB4 | Pat138 | V341M | egMeaaaatavvvve | 145 | HLA-DQA10101-DQB10301 | 0.04 | 0.04 |
| Cohort 2 | SERPINB4 | Pat138 | V341M | gMeaaaatavvvvel | 146 | HLA-DQA10101-DQB10301 | 0.08 | 0.07 |
| Cohort 2 | SERPINB4 | Pat138 | V341M | Meaaaatavvvvels | 147 | HLA-DQA10101-DQB10301 | 0.5 | 0.4 |
| Cohort 2 | SERPINB4 | Pat138 | V341M | vevteegMeaaaata | 148 | HLA-DQA10505-DQB10301 | 0.8 | 0.5 |
| Cohort 2 | SERPINB4 | Pat138 | V341M | evteegMeaaaatav | 149 | HLA-DQA10505-DQB10301 | 0.2 | 0.12 |
| Cohort 2 | SERPINB4 | Pat138 | V341M | vteegMeaaaatavv | 150 | HLA-DQA10505-DQB10301 | 0.1 | 0.05 |
| Cohort 2 | SERPINB4 | Pat138 | V341M | teegMeaaaatavvv | 151 | HLA-DQA10505-DQB10301 | 0.07 | 0.04 |
| Cohort 2 | SERPINB4 | Pat138 | V341M | eegMeaaaatavvvv | 152 | HLA-DQA10505-DQB10301 | 0.07 | 0.04 |
| Cohort 2 | SERPINB4 | Pat138 | V341M | egMeaaaatavvvve | 153 | HLA-DQA10505-DQB10301 | 0.1 | 0.06 |
| Cohort 2 | SERPINB4 | Pat138 | V341M | gMeaaaatavvvvel | 154 | HLA-DQA10505-DQB10301 | 0.2 | 0.12 |
| Cohort 2 | SERPINB4 | Pat138 | V341M | Meaaaatavvvvels | 155 | HLA-DQA10505-DQB10301 | 0.7 | 0.5 |
| Cohort 2 | SERPINB4 | Pat159 | R20K | eantkfmfdlfqqfK | 156 | HLA-DPA10103-DPB10201 | 0.02 | 0.02 |
| Cohort 2 | SERPINB4 | Pat159 | R20K | antkfmfdlfqqfKk | 157 | HLA-DPA10103-DPB10201 | 0.01 | 0.01 |
| Cohort 2 | SERPINB4 | Pat159 | R20K | ntkfmfdlfqqfKks | 158 | HLA-DPA10103-DPB10201 | 0.02 | 0.01 |
| Cohort 2 | SERPINB4 | Pat159 | R20K | tkfmfdlfqqfKksk | 159 | HLA-DPA10103-DPB10201 | 0.03 | 0.01 |
| Cohort 2 | SERPINB4 | Pat159 | R20K | kfmfdlfqqfKkske | 160 | HLA-DPA10103-DPB10201 | 0.1 | 0.08 |
| Cohort 2 | SERPINB4 | Pat159 | R20K | fmfdlfqqfKksken | 161 | HLA-DPA10103-DPB10201 | 1 | 0.7 |
| Cohort 2 | SERPINB4 | Pat159 | R20K | eantkfmfdlfqqfK | 162 | HLA-DPA10103-DPB10402 | 0.03 | 0.03 |
| Cohort 2 | SERPINB4 | Pat159 | R20K | antkfmfdlfqqfKk | 163 | HLA-DPA10103-DPB10402 | 0.01 | 0.01 |
| Cohort 2 | SERPINB4 | Pat159 | R20K | ntkfmfdlfqqfKks | 164 | HLA-DPA10103-DPB10402 | 0.01 | 0.01 |
| Cohort 2 | SERPINB4 | Pat159 | R20K | tkfmfdlfqqfKksk | 165 | HLA-DPA10103-DPB10402 | 0.01 | 0.01 |
| Cohort 2 | SERPINB4 | Pat159 | R20K | kfmfdlfqqfKkske | 166 | HLA-DPA10103-DPB10402 | 0.07 | 0.06 |
| Cohort 2 | SERPINB4 | Pat159 | R20K | fmfdlfqqfKksken | 167 | HLA-DPA10103-DPB10402 | 0.6 | 0.4 |

*Capital letter indicates position of mutated amino acid in 15-mer

Example 2: Materials and Methods for Performing Experiments Described Herein

Mutational Analysis and Whole-Exome Sequencing

Details of the anti-CTLA4 treated patient cohorts are previously described.[25,26] Whole-exome sequencing for cohort 1 and cohort 2 had been previously completed with mean depths of coverage of 103 and 183.7 respectively.[25,26] Analysis was performed as previously described by DePristo et. al.[27] Briefly, paired-end reads in FASTQ format were aligned to the reference human genome GRCh37 using Burrows-Wheeler Aligner (BWA v0.7.10).[28] Subsequently, local re-alignment was performed using the Genome Analysis Toolkit (GATK) version 3.2.2[29] Duplicate reads were removed using Picard version 1.119. Somatic single nucleotide variants (SNVs) were identified using a combination of four mutation callers, namely Mutect 1.1.4, Varscan 2.3.7, Somatic Sniper 1.0.4, and Strelka 1.0.13.[30-33] Sequence data from both cohorts were analyzed in the same manner. SNVs with an allele read count of less than 5 or with a normal coverage of less than 7 were removed. Small indels were called using GATK 3.2.2.

Statistics and Survival Analysis

Overall survival information and classification of patients into those with durable clinical benefit and those with minimal benefit were obtained from the original publications.[25,26] Survival analysis was performed with the Kaplan-Meier method with differences in survival being determined with the log-rank test. Multivariate survival analysis was performed using a Cox proportional hazards model. Differences in the distribution of quantitative variables between groups were determined with the Wilcox rank-sum test, unless otherwise indicated. Difference in proportions between groups were determined with Fisher's exact test, unless otherwise indicated. All statistical analyses were performed in the R statistical environment (v3.2).

Association of Recurrent Mutations with Survival

Since our initial report on anti-CTLA4 therapy in melanoma, the TCGA published a comprehensive genomic analysis of melanoma.[34] We analyzed the 19 recurrently mutated genes in melanoma identified by InVex and described by the TCGA (Supplemental Table 1).[34] All 19 genes were tested for association with overall survival using the chi-square test statistic from the survival package in R and a permutation procedure (Strona et. al.[35,36]). The overall procedure follows the concept described by Kim et al.[37]: We created N=10000 permutations of the binary mutation matrix (genes×samples), keeping row- and column sums constant, thereby accounting for potential confounding factors such as mutation load. In each iteration, we recorded the chi-square test statistic for association between permuted mutations and overall survival for all genes. An empiric p-value was derived for each recurrently mutated gene by comparing observed test statistics to the distribution of simulated test statistics. The association of SERPINB3 with OS was significant after Bonferroni correction for multiple testing at P=0.037 (uncorrected p-value=0.005). No other genes were significant.

We subsequently verified that SERPINB3 was also associated with overall survival in an independently collected group of patients, cohort 2 (from Germany) (p=0.05; FIG. 1a). As SERPINB3/B4 are close homologues, we grouped mutations in these genes together (see main text). Multivariate analysis correcting for M-stage and mutation load demonstrated that SERPINB3/B4 mutations were associated with overall survival in cohort 1 (HR=0.34, 95% CI=0.11-0.98, p=0.05) and cohort 2 (HR=0.32, 95% CI=0.13-0.76, p=0.01) (Supplemental Table 2).

Alignment of Ovalbumin and SERPINB3

Clustal Omega was used to align ovalbumin and SERPINB3. Presented epitopes for SERPINB3 were determined from the literature.[38] Immunogenic epitopes from ovalbumin were also determined from the literature.[39] The immune epitope database was accessed on 21 Mar. 2016, and was used to identify all relevant epitopes.

Computational Neoantigen Prediction

Class I HLA typing was performed manually for the Cohort I and for Cohort II was computed with polysolver from the exome data by the original authors. Each non-synonymous SNV was translated into a 17-mer peptide sequence, centered on the mutated amino acid. This 17-mer was then used to create 9-mers via a sliding window approach for determination of MHC-Class I binding.[4] netMHC version 3.4 was used to determine the binding strength of mutated peptides to patient specific HLA alleles.[41] All peptides with a binding score of IC50<500 nM were considered as putative class I neoantigens. For class II antigens, a 29-mer peptide sequence was created and a 15-mer sliding window approach was utilized. Class II HLA typing was determined with SOAP-HLA on both cohorts from the exome data. netMHCpan version 3.1 was used to determine the affinity of mutated peptides to patient specific HLA alleles, and those with a rank less than 2 percent, were considered putative Class II neoantigens.[42]

REFERENCES

1. Hodi, F. S. et al. Improved survival with ipilimumab in patients with metastatic melanoma. N Engl J Med 363, 711-23 (2010).
2. Robert, C. et al. Ipilimumab plus dacarbazine for previously untreated metastatic melanoma. N. Engl J Med 364, 2517-26 (2011).
3. Brahmer, J. et al. Nivolumab versus Docetaxel in Advanced Squamous-Cell Non-Small-Cell Lung Cancer. N Engl J Med 373, 123-35 (2015).
4. Motzer, R. J. et al. Nivolumab versus Everolimus in Advanced Renal-Cell Carcinoma. N Engl J Med 373, 1803-13 (2015).
5. Robert, C. et al. Nivolumab in previously untreated melanoma without BRAF mutation. N Engl J Med 372, 320-30 (2015).
6. Snyder, A. et al. Genetic basis for clinical response to CTLA-4 blockade in melanoma. N Engl J Med 371, 2189-99 (2014).
7. Rizvi, N. A. et al. Cancer immunology. Mutational landscape determines sensitivity to PD-1 blockade in non-small cell lung cancer. Science 348, 124-8 (2015).
8. Le, D. T. et al. PD-1 Blockade in Tumors with Mismatch-Repair Deficiency. N Engl J Med 372, 2509-20 (2015).
9. Van Allen, E. M. et al. Genomic correlates of response to CTLA-4 blockade in metastatic melanoma. Science 350, 207-11 (2015).
10. McGranahan, N. et al. Clonal neoantigens elicit T cell immunoreactivity and sensitivity to immune checkpoint blockade. Science (2016).
11. Cancer Genome Atlas, N. Genomic Classification of Cutaneous Melanoma. Cell 161, 1681-96 (2015).
12. Vidalino, L. et al. SERPINB3, apoptosis and autoimmunity. Autoimmun Rev 9, 108-12 (2009).
13. Gatto, M. et al. Serpins, immunity and autoimmunity: old molecules, new functions. Clin Rev Allergy Immunol 45, 267-80 (2013).

14. Sivaprasad, U. et al. SERPINB3/B4 contributes to early inflammation and barrier dysfunction in an experimental murine model of atopic dermatitis. J Invest Dermatol 135, 160-9 (2015).
15. Schneider, S. S. et al. A serine proteinase inhibitor locus at 18q21.3 contains a tandem duplication of the human squamous cell carcinoma antigen gene. Proc Natl Acad Sci USA 92, 3147-51 (1995).
16. Catanzaro, J. M. et al. Oncogenic Ras induces inflammatory cytokine production by upregulating the squamous cell carcinoma antigens SerpinB3/B4. Nat Commun 5, 3729 (2014).
17. Guan, J., Gupta, R. & Filipp, F. V. Cancer systems biology of TCGA SKCM: efficient detection of genomic drivers in melanoma. Sci Rep 5, 7857 (2015).
18. Katagiri, C., Nakanishi, J., Kadoya, K. & Hibino, T. Serpin squamous cell carcinoma antigen inhibits UV-induced apoptosis via suppression of c-JUN NH2-terminal kinase. J Cell Biol 172, 983-90 (2006).
19. El-Rachkidy, R. G., Young, H. S., Griffiths, C. E. & Camp, R. D. Humoral autoimmune responses to the squamous cell carcinoma antigen protein family in psoriasis. J Invest Dermatol 128, 2219-24 (2008).
20. Lysvand, H., Hagen, L., Klubicka, L., Slupphaug, G. & Iversen, O. J. Psoriasis pathogenesis—Pso p27 is generated from SCCA1 with chymase. Biochim Biophys Acta 1842, 734-8 (2014).
21. Munz, C. Antigen Processing for MHC Class II Presentation via Autophagy. Front Immunol 3, 9 (2012).
22. Schumacher, T. et al. A vaccine targeting mutant IDH1 induces antitumour immunity. Nature 512, 324-7 (2014).
23. Mine, Y. & Yang, M. Recent advances in the understanding of egg allergens: basic, industrial, and clinical perspectives. J Agric Food Chem 56, 4874-900 (2008).
24. Holen, E. & Elsayed, S. Specific T cell lines for ovalbumin, ovomucoid, lysozyme and two OA synthetic epitopes, generated from egg allergic patients' PBMC. Clin Exp Allergy 26, 1080-8 (1996).
25. Snyder, A. et al. N Engl J Med 371, 2189-99 (2014).
26. Van Allen, E. M. et al. Science 350, 207-11 (2015).
27. DePristo, M. A. et al. Nat Genet 43, 491-8 (2011).
28. Li, H. & Durbin, R. Bioinformatics 25, 1754-60 (2009).
29. McKenna, A. et al. Genome Res 20, 1297-303 (2010).
30. Cibulskis, K. et al. Nat Biotechnol 31, 213-9 (2013).
31. Koboldt, D. C. et al. Genome Res 22, 568-76 (2012).
32. Larson, D. E. et al. Bioinformatics 28, 311-7 (2012).
33. Saunders, C. T. et al. Bioinformatics 28, 1811-7 (2012).
34. Cancer Genome Atlas, N. Cell 161, 1681-96 (2015).
35. Strona, G., Nappo, D., Boccacci, F., Fattorini, S. & San-Miguel-Ayanz, J. Nat Commun 5, 4114 (2014).
36. Gotelli, N. J. & Ellison, A. M. EcoSimR 1.00.
37. Kim, J. et al. Nat Genet (2016).
38. Schellens, I. M. et al. PLoS One 10, e0136417 (2015).
39. Holen, E. & Elsayed, S. Clin Exp Allergy 26, 1080-8 (1996).
40. Snyder, A. & Chan, T. A. Curr Opin Genet Dev 30, 7-16 (2015).
41. Nielsen, M. et al. Protein Sci 12, 1007-17 (2003).
42. Andreatta, M. et al. Immunogenetics 67, 641-50 (2015).
43. Heit et al. Hum Genomics. 2013; 7(1): 22.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

---

We claim:

1. A method of treating cancer in a subject in need thereof comprising:
   administering a CTLA4 inhibitor to the subject, wherein the subject comprises cancer cells that include a mutation in SERPINB3 or SERPINB4.

2. The method of claim 1, wherein the cancer is or comprises a melanoma.

3. The method of claim 1, wherein the CTLA4 inhibitor is or comprises an anti-CTLA4 antibody agent.

4. The method of claim 3, wherein the anti-CTLA4 antibody agent is ipilimumab.

5. The method of claim 3, wherein the anti-CTLA4 antibody agent is tremelimumab.

6. A method for selecting cancer patients for treatment with a CTLA4 inhibitor comprising:
   identifying cancer patients comprising cancer cells that carry a SERPINB3 or SERPINB4 gene mutation, and
   administering a CTLA4 inhibitor to cancer patients comprising cancer cells that carry a SERPINB3 or SERPINB4 gene mutation.

7. The method of claim 1, wherein the patient has received or is receiving one or more other therapeutic agents.

* * * * *